US007232906B2

(12) United States Patent
Zhang et al.

(10) Patent No.: US 7,232,906 B2
(45) Date of Patent: Jun. 19, 2007

(54) SUBSTITUTED PYRROLINES AS KINASE INHIBITORS

(75) Inventors: Han Cheng Zhang, Lansdale, PA (US); Bruce E. Maryanoff, Forest Grove, PA (US); David F. McComsey, Warminster, PA (US); Kimberly White, North Wales, PA (US); Hong Ye, Lansdale, PA (US); Leonard R. Hecker, Harleysville, PA (US); Bruce Conway, Doylestown, PA (US); Keith Demarest, Flemington, NJ (US)

(73) Assignee: Janssen Pharmaceutica N.V., Beerse (BG)

( * ) Notice: Subject to any disclaimer, the term of this patent is extended or adjusted under 35 U.S.C. 154(b) by 271 days.

(21) Appl. No.: 10/454,561

(22) Filed: Jun. 4, 2003

(65) Prior Publication Data

US 2004/0054180 A1    Mar. 18, 2004

Related U.S. Application Data

(60) Provisional application No. 60/386,002, filed on Jun. 5, 2002.

(51) Int. Cl.
   *C07D 239/24*   (2006.01)
   *C07D 209/02*   (2006.01)
(52) U.S. Cl. ...................... 544/333; 546/144; 546/167; 548/455; 548/465
(58) Field of Classification Search ................ 546/144; 546/167; 548/455, 465
   See application file for complete search history.

(56) References Cited

U.S. PATENT DOCUMENTS

| | | | |
|---|---|---|---|
| 5,057,614 A | 10/1991 | Davis et al. | |
| 5,624,949 A | 4/1997 | Heath, Jr. et al. | |
| 5,721,245 A | 2/1998 | Davis et al. | |
| 6,037,475 A | 3/2000 | Faul et al. | |
| 6,479,490 B2 * | 11/2002 | Gong et al. | ............... 514/235.5 |
| 6,849,643 B2 | 2/2005 | Zhang | |
| 6,987,110 B2 | 1/2006 | Zhang | |
| 7,125,878 B2 | 10/2006 | Zhang | |
| 2004/0192718 A1 | 9/2004 | Zhang | |
| 2004/0259928 A1 | 12/2004 | Zhang | |
| 2005/0004201 A1 | 1/2005 | Zhang | |
| 2005/0004202 A1 | 1/2005 | Zhang | |
| 2006/0205762 A1 | 9/2006 | Zhang | |
| 2006/0205763 A1 | 9/2006 | Zhang | |

FOREIGN PATENT DOCUMENTS

| | | |
|---|---|---|
| EP | 1057484 | 12/2000 |
| EP | 1120414 A1 | 8/2001 |
| WO | WO 91/13071 A1 | 9/1991 |
| WO | WO 9517182 | 6/1995 |
| WO | WO 9811102 | 3/1998 |
| WO | WO 00/06564 A1 | 2/2000 |
| WO | WO 00/21927 A2 | 4/2000 |
| WO | WO 02/10158 A2 | 2/2002 |
| WO | WO 02/38561 A1 | 5/2002 |
| WO | WO 0246183 A | 6/2002 |

OTHER PUBLICATIONS

PCT Search Report dated Oct. 8, 2003 for PCT/US03/17569.
Davis, P.D. et al.: "Inhibitors of Protein Kinase C1.2,3-Bisarytmaleimides" Journal of Medicinal Chemistry, American Chemical Society. Washington, D.C., U.S. vol. 35, No. 1, 1992, pp. 177-184.
Zhu G et al: "Synthesis of Quinolinly/Isoquinolinyl(a)pyrrolo(3,4-c) Carbazoles as Cyclin D1/CDK4 Inhibitors" Bioorganic & Medicinal Chemistry Letters, Oxford, GB, vol. 13, Apr. 1, 2003, pp. 1231-1235 XP002255246.
International J. Pharm, 1986, 33, 201-217.
J. Pharm. Sci., Jan. 1977, 66(1), p. 1.
P. Xia, et al., J. Clin. Invest., 1996, 98, 2018.
H. Ishii, et al., J. Mol. Med., 1998, 76, 21.
Inoguchi, et al., Proc. Natl. Acad. Sci. USA, 1992, 89, 11059-11065.
Bastyr III, E.J. and Lu, J., Diabetes, 1993, 42, (Suppl. 1) 97A.
Hsieh, et al., Proc. Natl. Acad. Sci USA, 1991, 88, 9315-9319.
Hsieh, et al., J. Biol. Chem., 1993, 268, 15118-15126.
Murray, et al., J. Biol. Chem, 1993, 268, 15847-15853.
Bilder, G.E., et al., J. Pharmacol. Exp. Ther., 1990, 252, 526-530.
Matsumoto, H. and Sasaki, Y., Biochem. Biophys. Res. Commun., 1989, 158, 105-109.
Yan, S-F, et al., J. Biol. Chem., 2000, 275, 16, 11921-11928.
Ren, S., et al., Am. J. Physiol., 2000, 278 (4, Pt. 1), E656-E-662.
Muid, R.E., et al., FEBS Lett., 1990, 293, 169-172.
Sonoki, H. et al., Kokyu-To Junkan, 1989, 37, 669-674.
Kobayashi, et al., Amer. Phys. Soc., 1994, H1214-H1220.
Toullec, D., et al., J. Biol. Chem., 1991, 266, 15771-15781.
Karasik, A., et al., J. Biol. Chem., 1990, 265, 10226-10231.
Chen, K.S., et al., Trans. Assoc. Am. Physicians, 1991, 104, 206-212.
Chin, J.E., et a., J. Biol. Chem., 1993, 268, 6338-6347.
Lee, T-S., et al., J. Clin. Invest., 1989, 83, 90-94.
Lee, T-S., et al., Proc. Natl. Acad. Sci. USA, 1989, 86, 5141-5145.
Craven, P.A. and Derubertis, F.R., J. Clin. Invest., 1989, 87, 1667-1675.
Wolf, B.A., et al., J. Clin. Invest., 1991, 87, 31-38.
Tesfamariam,B., et al., J. Clin. Invest., 1991, 87, 1643-1648.
Ishii, H., et al., Science, 1996, 272, 728-731.
X. Gu, et al., Circ. Res., 1994, 75, 926.
R. H. Strasser, et al., Circulation, 1996, 94, 1551.
H. Wakasaki, et al., Proc. Natl. Acad. Sci. USA, 1997, 94, 9320.
Twoemy, B., et al., Biochem. Biophys. Res. Commun., 1990, 171, 1087-1092.
Mulqueen, J.M., et al., Agents Actions, 1992, 37, 85-89.
Nechushtan, H., et al., Blood, Mar. 2000, 95, 5, 1752-1757.
Ren, S., et al., Am. J. Physiol., 2000, 278, (4, Pt. 1), E656-E-662.
Nagpala, P.G., et al., J. Cell Physiol., 1996, 2, 249-55.
Dekker, L.V., et al., Biochem. J., 2000, 347, 285-289.
Slater. M.J., et al., Biorg. & Med. Chem., 1999, 7, 1067-1074.
Rabbi, M.F., et al., Virology, Jun. 5, 1998, 245, 2, 257-69.

(Continued)

*Primary Examiner*—Kamal A. Saeed

(57) ABSTRACT

The present invention is directed to novel substituted pyrroline compounds useful as kinase or dual-kinase inhibitors, methods for producing such compounds and methods for treating or ameliorating a kinase or dual-kinase mediated disorder.

31 Claims, No Drawings

OTHER PUBLICATIONS

Leitges. M., et al., Science (Wash., D.C.), 1996, 273, 5276, 788-789.
Horn, F., et al., J. Invest. Dermatol., 1987, 88, 220-222.
Raynaud, F. and Evain-Brion, D., Br. J. Dermatol., 1991, 124, 542-546.
Hegemann, L., et al., Arch. Dermatol. Res., 1991, 283, 456-460.
Bollag, W.B. et al., J. Invest. Dermatol., 1993, 100, 240-246.
Rotenberg, S.A. and Weinstein, I.B., Biochem. Mol. Aspects Sel. Cancer, 1991, 1, 25-73.
Ahmad, et al., Molecular Pharmacology, 1993, 43, 858-862.
Meyer, T., et al., Int. J. Cancer, 1989, 43, 851-856.
Akinagaka, S., et al., Cancer Res., 1991, 51, 4888-4892.
Sauma, S., et al., Cell Growth Differ., 1996, 7, 5, 587-94.
Konig, A., et al., Blood, 1997, 90, 10, Suppl. 1 Pt. 2.
Danso, D., et al., Proc. Am. Assoc. Cancer Res., 1997, 38, 88 Meet., 92.
Harrington, E.O., et al., J. Biol. Chem., 1997, 272, 11, 7390-7397.
Begemamm, M., et al., Anticancer Res. (Greece), Jul.-Aug. 1998, 18, 4A, 2275-82.
Teicher, B.A., et al., Proc. Am. Assoc. Cancer Res., 1998, 39, 89 Meet., 384.
Teicher, B.A. et al., Clinical Cancer Research, Mar. 2001, 7, 634-640.
Huang, K.P., Trends Neurosci., 1989, 12, 425-432.
Shimohama, S., et al., Neurology, 1993, 43, 1407-1413.
Hara, H., et al., J. Cereb. Blood Flow Metab., 1990, 10, 646-653.
Shibata, S., et al., Brain Res., 1992, 594, 290-294.
Beldhuis, H.J.A., et al., Neuroscience, 1993, 55, 4, 965-73.
Miletic, V., et al., Neurosci. Lett., 2000, 288, 3, 199-202.
Chen, C., et al., Science (Wash., D.C.), 1997, 278, 5336, 279-283.
Embi, et al., Eur. J. Biochem, 1980, 107, 519-527.
Cross, et al., Biochemical Journal, 1994, 303, 21-26.
Villar-Palasi C. and Larner J., Biochim. Biophys. Acta, 1960, 39, 171-173.
Parker, P.J., et al., Eur J. Biochem, 1983, 130, 227-234.
Cohen, P., Biochem. Soc. Trans., 1993, 21, 555-567.
Srivastava, A.K. and Pandey S.K., Mol. and Cellular Biochem., 1998, 182, 135-141.
Chen, et al., Diabetes, 1994, 43, 1234-1241.
Eldar-Finkelman, et al., PNAS, 1996, 93, 10228-10233.
Eldar-Finkelman and Krebs, PNAS, 1997, 94, 9660-9664.
Eldar-Finkelman, et al., Diabetes, 1999, 48, 1662-1666.
Gat, et al., Cell, 1998, 95, 605-614.
Hoeflich, K.P., et al., Nature, 2000, 406, 86-90.
Pap and Cooper, J. Biol. Chem., 1998, 273, 19929-19932.
D'Mello, et al., Exp. Cell Res., 1994, 211, 332-338.
Nonaka and Chuang, Neuroreport, 1998, 9(9), 2081-2084.
Hong, J. et al., J. Biol. Chem. 1997, 272(40), 25326-32.
Ikeda, et al., EMBO J., 1998, 17, 1371-1384.
Eastman, Grosschedl, Curr. Opin. Cell Biol., 1999, 11, 233.
Cotter, D., et al., Neuroreport, 1998, 9, 1379-1383.
Lijam, N., et al., Cell, 1997, 90, 895-905.
Manji, et al., J. Clin. Psychiatry, 1990, 60, (Suppl 2) 27-39.
U.S. Appl. No. 11/528,092, filed Sep. 27, 2006, Zhang.

* cited by examiner

SUBSTITUTED PYRROLINES AS KINASE INHIBITORS

FIELD OF THE INVENTION

This application claims benefit of provisional patent application 60/386,002 filed on Jun. 5, 2002, which is hereby incorporated by reference herein.

This invention is directed to certain novel compounds, methods for producing them and methods for treating or ameliorating a kinase or dual-kinase mediated disorder. More particularly, this invention is directed to substituted pyrroline compounds useful as selective kinase or dual-kinase inhibitors, methods for producing such compounds and methods for treating or ameliorating a kinase or dual-kinase mediated disorder.

BACKGROUND OF THE INVENTION

U.S. Pat. No. 5,057,614 to Davis, et. al., describes substituted pyrrole compounds of formula I as therapeutically active substances for the use in control or prevention of inflammatory, immunological, bronchopulmonary and cardiovascular disorders:

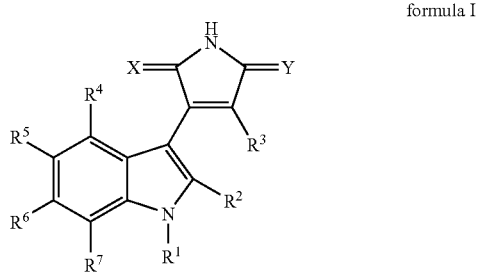

formula I wherein $R^1$ signifies hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula:

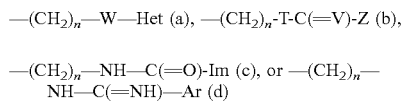

in which Het signifies a heterocyclyl group, W signifies NH, S or a bond, T signifies NH or S, V signifies O, S, NH, $NNO_2$, NCN or $CHNO_2$, Z signifies alkylthio, amino, monoalkylamino or dialkylamino, Im signifies 1-imidazolyl, Ar signifies aryl, and n stands for 2–6; $R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl; $R^3$ signifies a carbocyclic or heterocyclic aromatic group; $R^4$, $R^5$, $R^6$ and $R^7$ each independently signify hydrogen, halogen, hydroxy, alkoxy, aryloxy, haloalkyl, nitro, amino, acylamino, monoalkylamino, dialkylamino, alkylthio, alkylsulphinyl or alkylsulphonyl; and one of X and Y signifies O and the other signifies O, S, (H,OH) or (H,H); with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; as well as pharmaceutically acceptable salts of acidic compounds of formula I with bases and of basic compounds of formula I with acids; wherein the $R^3$ carbocyclic aromatic group is defined as a monocyclic or polycyclic group, preferably a monocyclic or bicyclic group such as phenyl or naphthyl which can be unsubstituted or substituted with 1 or more, preferably 1 to 3, substituents selected from halogen, unsubstituted $C_{1-7}$alkyl, hydroxy, unsubstituted $C_{1-7}$alkoxy, (halo)$_{1-3}$($C_{1-7}$) alkyl, nitro, amino, acylamino, monoalkylamino, dialkylamino, alkylthio, alkylsulphinyl or alkylsulfonyl; wherein the $R^3$ carbocyclic aromatic group is selected from phenyl, 2-, 3- or 4-chlorophenyl, 3-bromophenyl, 2- or 3-methylphenyl, 2,5-dimethylphenyl, 4-methoxyphenyl, 2- or 3-trifluoromethylphenyl, 2-, 3- or 4-nitrophenyl, 3- or 4-aminophenyl, 4-methylthiophenyl, 4-methylsulphinylphenyl, 4-methylsulphonylphenyl or 1- or 2-naphthyl; wherein the $R^3$ heterocyclic aromatic group is defined as a 5- or 6-membered heterocyclic aromatic group optionally fused with a benzene ring and substituted or unsubstituted with 1 or more, preferably 1 to 3, substituents selected from halogen, ($C_{1-7}$)alkyl, hydroxy, ($C_{1-7}$)alkoxy, ($C_{1-7}$)alkyl-halo, nitro, amino, —NH—C(O)—($C_{1-7}$)alkyl, —NH($C_{1-7}$alkyl), —N($C_{1-7}$alkyl)$_2$, —S—($C_{1-7}$)alkyl, —C(SO)—($C_{1-7}$)alkyl or —SO$_2$—($C_{1-7}$)alkyl; wherein the $R^3$ heterocyclic aromatic group is 2- or 3-thienyl, 3-benzothienyl, 1-methyl-2-pyrrolyl, 1-benzimidazolyl, 3-indolyl, 1- or 2-methyl-3-indolyl, 1-methoxymethyl-3-indolyl, 1-(1-methoxyethyl)-3-indolyl, 1-(2-hydroxypropyl)-3-indolyl, 1-(4-hydroxybutyl)-3-indolyl, 1-[1-(2-hydroxyethylthio)ethyl]-3-indolyl, 1-[1-(2-mercaptoethylthio)ethyl]-3-indolyl, 1-(1-phenylthioethyl)-3-indolyl, 1-[1-(carboxymethylthio)ethyl]-3-indolyl or 1-benzyl-3-indolyl; and, when the $R^3$ heterocyclic aromatic group is 3-indolyl, the 3-indolyl nitrogen atom is substituted with a substituent selected from hydrogen, $C_{1-7}$alkyl, aryl (wherein aryl is phenyl unsubstituted or substituted with 1 or more, preferably 1 to 3, substituents selected from halogen, unsubstituted $C_{1-7}$alkyl, hydroxy, unsubstituted $C_{1-7}$alkoxy, (halo)$_{1-3}$($C_{1-7}$)alkyl, nitro, amino, acylamino, monoalkylamino, dialkylamino, alkylthio, alkylsulphinyl or alkylsulfonyl), —($C_{1-7}$)alkyl-aryl (wherein aryl is phenyl unsubstituted or substituted with 1 or more, preferably 1 to 3, substituents selected from halogen, unsubstituted $C_{1-7}$alkyl, hydroxy, unsubstituted $C_{1-7}$alkoxy, (halo)$_{1-3}$($C_{1-7}$)alkyl, nitro, amino, acylamino, monoalkylamino, dialkylamino, alkylthio, alkylsulphinyl or alkylsulfonyl), —($C_{1-7}$)alkyl($C_{1-7}$)alkoxy, —($C_{1-7}$)alkyl-hydroxy, —($C_{1-7}$)alkyl-(halo)$_{1-3}$, —($C_{1-7}$)alkyl-NH$_2$, —($C_{1-7}$)alkyl-NH($C_{1-7}$alkyl), —($C_{1-7}$)alkyl-N($C_{1-7}$alkyl)$_2$, —($C_{1-7}$)alkyl-N$^+$($C_{1-7}$alkyl)$_3$, —($C_{1-7}$)alkyl-NH($C_{1-7}$alkyl)NH$_2$, —($C_{1-7}$)alkyl-N$_3$, —$C_{1-7}$alkyl-NH—C(O)—($C_{1-7}$)alkyl, —$C_{1-7}$alkyl-S—C(O)—($C_{1-7}$)alkyl, —$C_{1-7}$alkyl-NH—SO$_2$—($C_{1-7}$)alkyl, —$C_{1-7}$alkyl-NH—SO$_2$-aryl (wherein aryl is phenyl unsubstituted or substituted with 1 or more, preferably 1 to 3, substituents selected from halogen, unsubstituted $C_{1-7}$alkyl, hydroxy, unsubstituted $C_{1-7}$alkoxy, (halo)$_{1-3}$($C_{1-7}$)alkyl, nitro, amino, acylamino, monoalkylamino, dialkylamino, alkylthio, alkylsulphinyl or alkylsulfonyl), —(C$_{1-7}$)alkyl-SH, —(C$_{1-7}$)alkyl-S—(C$_{1-7}$)alkyl, —(C$_{1-7}$)alkyl-C(SO)—(C$_{1-7}$)alkyl, —(C$_{1-7}$)alkyl-SO$_2$—(C$_{1-7}$)alkyl, —(C$_{1-7}$)alkyl-O—SO$_2$—(C$_{1-7}$)alkyl, —(C$_{1-7}$)alkyl-O—C(O)—(C$_{1-7}$)alkyl, —(C$_{1-7}$)alkyl-C(N), —(C$_{1-7}$)alkyl-C(NH)—NH$_2$, glucopyranosyl, —(C$_{1-7}$)alkyl-CO$_2$H, —(C$_{1-7}$) alkyl-C(O)—O—(C$_{1-7}$)alkyl, —(C$_{1-7}$)alkyl-C(O)—NH$_2$, —(C$_{1-7}$)alkyl-S—(C$_{1-7}$)alkyl-OH, —(C$_{1-7}$)alkyl-S—(C$_{1-7}$)alkyl-SH, —C$_{1-7}$alkyl-S-aryl (wherein aryl is phenyl unsubstituted or substituted with 1 or more, preferably 1 to 3, substituents selected from halogen, unsubstituted C$_{1-7}$alkyl, hydroxy, unsubstituted C$_{1-7}$alkoxy, (halo)$_{1-3}$(C$_{1-7}$)alkyl, nitro, amino, acylamino, monoalkylamino, dialkylamino, alkylthio, alkylsulphinyl or alkylsulfonyl), —(C$_{1-7}$)alkyl-S—(C$_{1-7}$)alkyl-CO$_2$H, —(CH$_2$)$_{2-6}$-W-Het (wherein W is selected from NH, S or a bond; wherein Het is a saturated, partially saturated or aromatic 5- or 6-membered heterocyclic group optionally fused with a benzene ring and substituted or unsubstituted with 1 or more, preferably 1 to 3, substituents selected from halogen, (C$_{1-7}$)alkyl, hydroxy, (C$_{1-7}$)alkoxy, (C$_{1-7}$)alkyl-halo, nitro, amino, —NH—C(O)—(C$_{1-7}$)alkyl, —(C$_{1-7}$)alkyl-NH(C$_{1-7}$alkyl), —(C$_{1-7}$)alkyl-N(C$_{1-7}$alkyl)$_2$, —S—(C$_{1-7}$)alkyl, —C(SO)—(C$_{1-7}$)alkyl or —SO$_2$—(C$_{1-7}$)alkyl; wherein when Het is an aromatic nitrogen-containing heterocyclic group, a nitrogen atom may be substituted with an oxide group; and, wherein Het is selected from imidazolyl, imidazolinyl, thiazolinyl, pyridyl or pyrimidinyl), —(CH$_2$)$_{2-6}$-T-C(V)-Z (wherein T is selected from NH or S; V is selected from O, S, NH, NNO$_2$, NCN or CHNO$_2$; and, Z is selected from —S—(C$_{1-7}$)alkyl, NH$_2$, NH(C$_{1-7}$alkyl) or N(C$_{1-7}$alkyl)$_2$), —(CH$_2$)$_{2-6}$—NH—C(O)-1-imidazolyl or —(CH$_2$)$_{2-6}$—NH—C(=NH)-aryl (wherein aryl is phenyl unsubstituted or substituted with 1 or more, preferably 1 to 3, substituents selected from halogen, unsubstituted C$_{1-7}$alkyl, hydroxy, unsubstituted C$_{1-7}$alkoxy, (halo)$_{1-3}$ (C$_{1-7}$)alkyl, nitro, amino, acylamino, monoalkylamino, dialkylamino, alkylthio, alkylsulphinyl or alkylsulfonyl).

U.S. Pat. No. 6,037,475 to Faul, et. al., describes a method of making an N-substituted indolylmaleimide of formula I as therapeutically active substances for the use in control or prevention of inflammatory, immunological, bronchopulmonary and cardiovascular disorders:

formula I

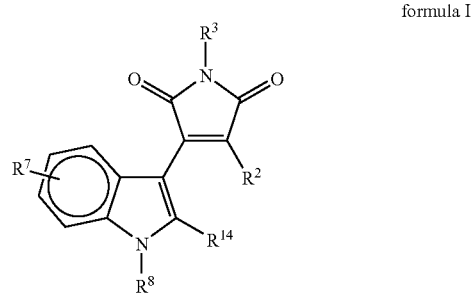

using an organometallic reagent and an optionally substituted activated organometallic-3-indole maleimide in the presence of a palladium transition metal catalyst wherein R$^2$ is selected from a leaving group and an optionally substituted indol-3-yl, R$^3$ is selected from hydrogen and a protecting group, R$^7$'s are hydrogen or up to four optional substituents independently selected from halo, alkyl, hydroxy, alkoxy, haloalkyl, nitro, —NHCO(alkyl), or —NR$^9$R$^{10}$; where R$^9$ and R$^{10}$ are independently hydrogen, or methyl, R$^8$ is hydrogen or an optional substituent selected from, alkyl, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group, an alkylglycose residue, or a group of the formula:

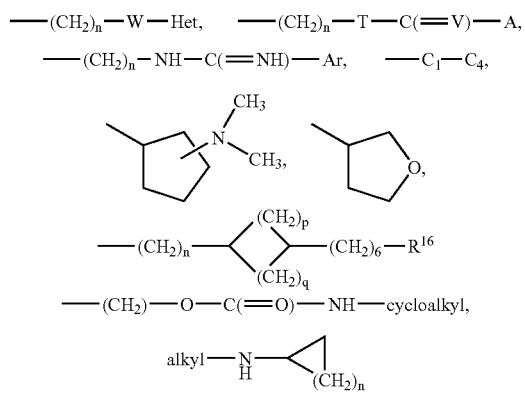

in which Het signifies a heterocyclyl group, W signifies NH, S or a bond, T signifies NH or S, V signifies O, S, NH or NCN, A signifies alkylthio, amino, monoalkylamino or dialkylamino, and Ar signifies aryl; R$^{16}$ is hydrogen, alkyl, haloalkyl, acetyl, aryl, —CH(aryl)$_2$, amino, monoalkylamino, dialkylamino, guanidino, —C(=N(alkoxy-carbonyl))-NH-(alkoxycarbonyl), amidino, hydroxy, carboxy, alkoxycarbonyl or heterocyclyl; R$^{14}$ is hydrogen or an optionally substituted alkyl; or R$^8$ and R$^{14}$ are linked together through a group of the formula (—(CH$_2$)$_r$—X—(CH$_2$)—) where X is —(C(—(CH$_2$)$_6$—R$^{17}$)(—(CH$_2$)$_6$—R$^{18}$))— where R$^{17}$ and R$^{18}$ are independently hydroxy, carboxy, acyloxy, amino, monoalkylamino, dialkylamino, trialkylamino, azido, acylamino, cyano, amidino or aminocarbonyl, and n is 1, 2, 3, 4, 5 or 6, p an q are 1, 2, 3 or 4, r is 1, 2 or 3, s is 0, 1, 2 or 3, t is 1 or 2, and u is 0 or 1.

U.S. Pat. No. 5,721,245 to Davis, et. al., describes substituted 4-[3-indolyl]-1H-pyrrolone compounds of formula I:

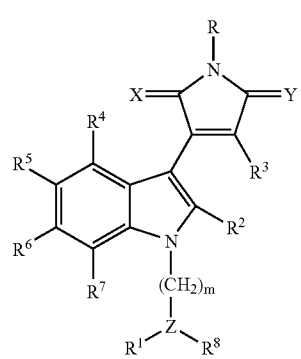

wherein R is hydrogen or hydroxy, R$^1$ and R$^2$ taken together are a group of the formula —(CH$_2$)$_n$— and R$^7$ is hydrogen or R$^1$ and R$^7$ taken together are a group of the formula —(CH$_2$)$_n$— and R$^2$ is hydrogen; R$^3$ is an aryl or aromatic heterocyclic group; R$^4$, R$^5$ and R$^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula $-(CH_2)_p-R^9$ or $-(CH_2)_q-R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, alkoxycarbonylamino, aminoacylamino, aminocarbonylamino, isothiocyanato, alkylcarbonyloxy, alkylsulfonyloxy or arylsulfonyloxy, a 5- or 6-membered saturated nitrogen-containing heterocycle attached via the nitrogen atom or a group of the formula -U-C(V)-W; U is S or NH; V is NH, $NNO_2$, NCN, $CHNO_2$; W is amino, monoalkylamino or dialkylamino; one of X and Y is O and the other is O or (H,H); Z is CH or N; m, p and q are, independently, an integer from 0 to 5, and n is an integer from 1 to 5, with the proviso that q and m are, independently, 2 to 5 when Z is N; as well as pharmaceutically acceptable salts of acidic compounds of formula I with bases and of basic compounds of formula I with acids, as therapeutically active substances for use in control or prevention of inflammatory, immunological, bronchopulmonary and cardiovascular disorders.

U.S. Pat. No. 5,624,949 to Heath, Jr., et. al., describes bis-indolemaleimide derivatives of the formula:

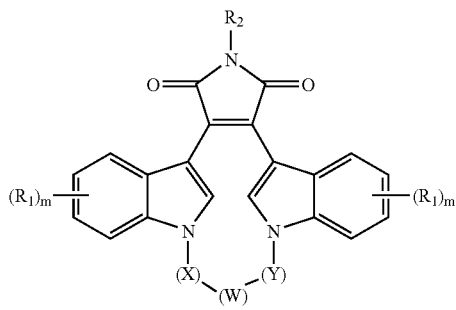

wherein W is $-O-$, $-S-$, $-SO-$, $-SO_2-$, $-CO-$, $C_2-C_6$ alkylene, substituted alkylene, $C_2-C_6$ alkenylene, -aryl-, -aryl($CH_2$)$_m$O—, -heterocycle-, -heterocycle-($CH_2$)$_m$O—, -fused bicyclic-, -fused bicyclic-($CH_2$)$_m$O—, $-NR_3-$, $-NOR_3-$, $-CONH-$ or $-NHCO-$; X and Y are independently $C_1-C_4$ alkylene, substituted alkylene, or together, X, Y and W combine to form $(CH_2)_n$-AA-; $R_1$ is independently hydrogen, halo, $C_1-C_4$ alkyl, hydroxy, $C_1-C_4$ alkoxy, haloalkyl, nitro, $NR_4R_5$ or $-NHCO(C_1-C_4)$alkyl; $R_2$ is hydrogen, $CH_3CO-$, $NH_2$ or hydroxy; $R_3$ is hydrogen, $(CH_2)_m$aryl, $C_1-C_4$ alkyl, $-COO(C_1-C_4$ alkyl), $-CONR_4R_5$, $-C(C=NH)NH_2$, $-SO(C_1-C_4$ alkyl), $-SO_2(NR_4R_5)$ or $-SO_2(C_1-C_4$ alkyl); $R_4$ and $R_5$ are independently hydrogen, $C_1-C_4$ alkyl, phenyl, benzyl, or combine to the nitrogen to which they are bonded to form a saturated or unsaturated 5 or 6 member ring; AA is an amino acid residue; m is independently 0, 1, 2 or 3; and n is independently 2, 3, 4 or 5 as protein kinase C (PKC) inhibitors and as selective PKCβ-I and PKCβ-II inhibitors.

Patent application WO 00/06564 discloses disubstituted maleimide compounds of Formula (I):

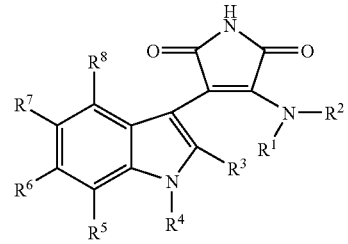

wherein $R^1$ represents hydrogen or alkyl; $R^2$ represents aryl, cycloalkyl or a heterocycle; $R^3$, $R^5$, $R^6$, $R^7$ and $R^8$ represent each hydrogen, halogen, hydroxy, amino, alkyl or alkoxy; and $R^4$ is W, or $R^4$ and $R^3$ or $R^4$ and $R^5$ may form together a ring substituted by W thereon; wherein W represents $-(CH_2)_l-(Y)_m-(CH_2)_n$-Z as PKCβ inhibitors.

Patent application WO 00/21927 describes 3-amino-4-arymaleimide compounds having formula (I):

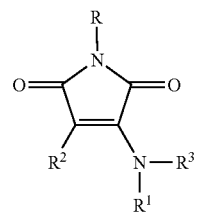

or a pharmaceutically acceptable derivative thereof, wherein: R is hydrogen, alkyl, aryl or aralkyl; $R^1$ is hydrogen, alkyl, aralkyl, hydroxyalkyl or alkoxyalkyl; $R^2$ is substituted or unsubstituted aryl or substituted or unsubstituted heterocyclyl; $R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocyclic ring and a method for the treatment of conditions associated with a need for inhibition of GSK-3, such as diabetes, dementias such as Alzheimer's disease and manic depression.

The substituted pyrroline compounds of the present invention have not been heretofore disclosed.

Accordingly, it is an object of the present invention to provide substituted pyrroline compounds useful as a kinase or dual-kinase inhibitor (in particular, a kinase selected from protein kinase C or glycogen synthase kinase-3; and, more particularly, a kinase selected from protein kinase C α, protein kinase C β-II, protein kinase C γ or glycogen synthase kinase-3β), methods for their production and methods for treating or ameliorating a kinase or dual-kinase mediated disorder.

SUMMARY OF THE INVENTION

The present invention is directed to substituted pyrroline compounds of Formula (I)

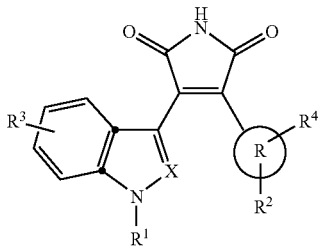

Formula (I)

wherein

R is selected from phenyl, naphthyl, furyl, thienyl, pyridinyl, pyrimidinyl, benzothienyl, quinolinyl or isoquinolinyl;

$R^1$ is selected from hydrogen, —$C_{1-8}$alkyl-$R^5$, —$C_{2-8}$alkenyl-$R^5$, —$C_{2-8}$alkynyl-$R^5$, -aryl-$R^6$ or -heteroaryl-$R^6$; wherein a heteroaryl ring carbon atom forms the point of attachment to the indole nitrogen atom;

$R^5$ is 1 to 2 substituents independently selected from hydrogen, —O—($C_{1-8}$)alkyl, —O—($C_{1-8}$)alkyl-OH, —O—($C_{1-8}$)alkyl-O—($C_{1-8}$)alkyl, —O—($C_{1-8}$)alkyl-NH$_2$, —O—($C_{1-8}$)alkyl-NH($C_{1-8}$alkyl), —O—($C_{1-8}$)alkyl-N($C_{1-8}$alkyl)$_2$, —O—($C_{1-8}$)alkyl-S—($C_{1-8}$)alkyl, —O—($C_{1-8}$)alkyl-SO$_2$—($C_{1-8}$)alkyl, —O—($C_{1-8}$)alkyl-SO$_2$—NH$_2$, —O—($C_{1-8}$)alkyl-SO$_2$—NH($C_{1-8}$ alkyl), —O—($C_{1-8}$)alkyl-SO$_2$—N($C_{1-8}$alkyl)$_2$, —O—C(O)H, —O—C(O)—($C_{1-8}$)alkyl, —O—C(O)—NH$_2$, —O—C(O)—NH($C_{1-8}$alkyl), —O—C(O)—N($C_{1-8}$alkyl)$_2$, —O—($C_{1-8}$)alkyl-C(O)H, —O—($C_{1-8}$)alkyl-C(O)—($C_{1-8}$)alkyl, —O—($C_{1-8}$)alkyl-CO$_2$H, —O—($C_{1-8}$)alkyl-C(O)—O—($C_{1-8}$)alkyl, —O—($C_{1-8}$)alkyl-C(O)—NH$_2$, —O—($C_{1-8}$)alkyl-C(O)—NH($C_{1-8}$alkyl), —O—($C_{1-8}$)alkyl-C(O)—N($C_{1-8}$alkyl)$_2$, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH($C_{1-8}$alkyl), —C(O)—N($C_{1-8}$alkyl)$_2$, —SH, —S—($C_{1-8}$)alkyl, —S—($C_{1-8}$)alkyl-S—($C_{1-8}$)alkyl, —S—($C_{1-8}$)alkyl-O—($C_{1-8}$)alkyl, —S—($C_{1-8}$)alkyl-O—($C_{1-8}$)alkyl-OH, —S—($C_{1-8}$)alkyl-O—($C_{1-8}$)alkyl-NH$_2$, —S—($C_{1-8}$)alkyl-O—($C_{1-8}$) alkyl-NH($C_{1-8}$alkyl), —S—($C_{1-8}$)alkyl-O—($C_{1-8}$)alkyl-N($C_{1-8}$alkyl)$_2$, —S—($C_{1-8}$)alkyl-NH($C_{1-8}$ alkyl), —SO$_2$—($C_{1-18}$)alkyl, —SO$_2$—NH$_2$, —SO$_2$—NH($C_{1-8}$ alkyl), —SO$_2$—N($C_{1-8}$alkyl)$_2$, —N—$R^7$, —($C_{1-4}$)alkyl-N—$R^7$, cyano, (halo)$_{1-3}$, hydroxy, nitro, oxo, -cycloalkyl-$R^6$, —($C_{1-4}$)alkyl-cycloalkyl-$R^6$, -heterocyclyl-$R^6$, —($C_{1-4}$)alkyl-heterocyclyl-$R^6$, -aryl-$R^6$, —($C_{1-4}$)alkyl-aryl-$R^6$, -heteroaryl-$R^6$ or —($C_{1-4}$)alkyl-heteroaryl-$R^6$;

$R^6$ is 1 to 4 substituents attached to a carbon or nitrogen atom independently selected from hydrogen, —$C_{1-8}$ alkyl, —($C_{1-8}$)alkyl-(halo)$_{1-3}$ or —($C_{1-8}$)alkyl-OH;
with the proviso that, when $R^6$ is attached to a carbon atom, $R^6$ is further selected from —$C_{1-8}$alkoxy, —C(O)NH$_2$, —NH$_2$, —NH($C_{1-8}$alkyl), —N($C_{1-8}$alkyl)$_2$, cyano, halo, —($C_{1-8}$)alkoxy-(halo)$_{1-3}$, hydroxy or nitro;

$R^7$ is 2 substituents independently selected from hydrogen, —$C_{1-8}$alkyl, —$C_{2-8}$alkenyl, —$C_{2-8}$alkynyl, —($C_{1-8}$) alkyl-OH, —($C_{1-8}$)alkyl-O—($C_{1-8}$)alkyl, —($C_{1-8}$)alkyl-NH$_2$, —($C_{1-8}$)alkyl-NH($C_{1-8}$alkyl), —($C_{1-8}$)alkyl-N($C_{1-8}$alkyl)$_2$, —($C_{1-8}$)alkyl-S—($C_{1-8}$) alkyl, —C(O)—($C_{1-8}$)alkyl, —C(O)—O—($C_{1-8}$)alkyl, —C(O)—NH$_2$, —C(O)—NH($C_{1-8}$alkyl), —C(O)—N($C_{1-8}$alkyl)$_2$, —SO$_2$—($C_{1-8}$)alkyl, —SO$_2$—NH$_2$, —SO$_2$—NH($C_{1-8}$alkyl), —SO$_2$—N($C_{1-8}$alkyl)$_2$, —C(N)—NH$_2$, -cycloalkyl-$R^8$, —($C_{1-8}$)alkyl-heterocyclyl-$R^8$, -aryl-$R^8$, —($C_{1-8}$)alkyl-aryl-$R^8$ or —($C_{1-8}$)alkyl-heteroaryl-$R^8$;

$R^8$ is 1 to 4 substituents attached to a carbon or nitrogen atom independently selected from hydrogen, —$C_{1-8}$ alkyl, —($C_{1-8}$)alkyl-(halo)$_{1-3}$ or —($C_{1-8}$)alkyl-OH;
with the proviso that, when $R^8$ is attached to a carbon atom, $R^8$ is further selected from —$C_{1-8}$alkoxy, —NH$_2$, —NH($C_{1-8}$alkyl), —N($C_{1-8}$alkyl)$_2$, cyano, halo, —($C_{1-8}$) alkoxy-(halo)$_{1-3}$, hydroxy or nitro;

$R^2$ is one substituent attached to a carbon atom selected from hydrogen, —$C_{1-8}$alkyl-$R^5$, —$C_{2-8}$alkenyl-$R^5$, —$C_{2-8}$alkynyl-$R^5$, —C(O)H, —C(O)—($C_{1-8}$)alkyl-$R^9$, —C(O)—NH$_2$, —C(O)—NH($C_{1-8}$alkyl-$R^9$), —C(O)—N($C_{1-8}$alkyl-$R^9$)$_2$, —C(O)—N H(aryl-$R^8$), —C(O)-cycloalkyl-$R^8$, —C(O)-heterocyclyl-$R^8$, —C(O)-aryl-$R^8$, —C(O)-heteroaryl-$R^8$, —CO$_2$H, —C(O)—O—($C_{1-8}$)alkyl-$R^9$, —C(O)—O-aryl-$R^8$, —SO$_2$—($C_{1-8}$)alkyl-$R^9$, —SO$_2$-aryl-$R^8$, -cycloalkyl-$R^6$, -aryl-$R^6$, —($C_{1-8}$)alkyl-N—$R^7$ —$C_{1-8}$alkoxy-$R^5$, —N—$R^7$, cyano, halogen, hydroxy, nitro, oxo (wherein oxo is attached to a saturated carbon atom), -heterocyclyl-$R^6$ or -heteroaryl-$R^6$;

$R^9$ is 1 to 2 substituents independently selected from hydrogen, —$C_{1-8}$alkoxy, —NH$_2$, —NH($C_{1-8}$alkyl), —N($C_{1-8}$alkyl)$_2$, cyano, (halo)$_{1-3}$, hydroxy or nitro;

$R^3$ is 1 to 4 substituents attached to a carbon atom independently selected from hydrogen, —$C_{1-8}$alkyl-$R^{10}$, —$C_{2-8}$alkenyl-$R^{10}$, —$C_{2-8}$alkynyl-$R^{10}$, —$C_{1-8}$ alkoxy-$R^{10}$, —C(O)H, —C(O)—($C_{1-8}$)alkyl-$R^9$, —C(O)—NH$_2$, —C(O)—NH($C_{1-8}$alkyl-$R^9$), —C(O)—N($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-8}$)alkyl-$R^9$, —C(O)—O-aryl-$R^8$, —SO$_2$—($C_{1-8}$) alkyl-$R^9$, —SO$_2$-aryl-$R^8$, —N—$R^7$, —($C_{1-8}$)alkyl-N—$R^7$, cyano, halogen, hydroxy, nitro, -cycloalkyl-$R^8$, -heterocyclyl-$R^8$, -aryl-$R^8$ or -heteroaryl-$R^8$;

$R^4$ is 1 to 4 substituents attached to a carbon atom independently selected from hydrogen, —$C_{1-8}$alkyl-$R^{10}$, —$C_{2-8}$alkenyl-$R^{10}$, —$C_{2-8}$alkynyl-$R^{10}$, —$C_{1-8}$ alkoxy-$R^{10}$, —C(O)H, —C(O)—($C_{1-8}$)alkyl-$R^9$, —C(O)—NH$_2$, —C(O)—NH($C_{1-8}$alkyl-$R^9$), —C(O)—N($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-8}$)alkyl-$R^9$, —C(O)—O-aryl-$R^8$, —SH, —S—($C_{1-8}$) alkyl-$R^{10}$, —SO$_2$—($C_{1-8}$)alkyl-$R^9$, —SO$_2$-aryl-$R^8$, —SO$_2$—NH$_2$, —SO$_2$—NH($C_{1-8}$alkyl-$R^9$) —SO$_2$—N($C_{1-8}$alkyl-$R^9$)$_2$, —N—$R^7$, —($C_{1-8}$) alkyl-N—$R^7$, cyano, halogen, hydroxy, nitro, -cycloalkyl-$R^8$, -heterocyclyl-$R^8$, -aryl-$R^8$ or -heteroaryl-$R^8$;

$R^{10}$ is 1 to 2 substituents independently selected from hydrogen, —NH$_2$, —NH($C_{1-8}$alkyl), —N($C_{1-8}$alkyl)$_2$, cyano, (halo)$_{1-3}$, hydroxy, nitro or oxo;

X is selected from N or CR$^{11}$; and, $R^{11}$ is selected from hydrogen, —$C_{1-8}$alkyl-$R^{10}$, —$C_{2-8}$ alkenyl-$R^{10}$, —$C_{2-8}$alkynyl-$R^{10}$, —$C_{1-8}$alkoxy-$R^{10}$, -aryl-$R^8$, -heteroaryl-$R^8$ or halogen;

with the provisio that when X is CH and R is phenyl, naphthyl, primidinyl or quinolinyl; $R^1$ is —$C_{1-8}$alkyl-$R^5$, —$C_{2-8}$alkenyl-$R^5$, —$C_{2-8}$alkynyl-$R^5$ or -naphthyl-$R^6$, -heteroaryl-$R^6$; wherein a heteroaryl ring carbon atom forms the point of attachment to the indole nitrogen atom; wherein $R^5$ for the —$C_{1-8}$alkyl-$R^5$ is not H, OH, NH$_2$, NHC$_{1-4}$alkyl, or N(di-$C_{1-4}$alkyl)$_2$ and pharmaceutically acceptable salts thereof.

The present invention is directed to substituted pyrroline compounds useful as a selective kinase or dual-kinase inhibitor; in particular, a kinase selected from protein kinase C or glycogen synthase kinase-3; and, more particularly, a kinase selected from protein kinase C α, protein kinase C β-II, protein kinase C γ or glycogen synthase kinase-3β.

The present invention is also directed to methods for producing the instant substituted pyrroline compounds and pharmaceutical compositions and medicaments thereof.

The present invention is further directed to methods for treating or ameliorating a kinase or dual-kinase mediated disorder.

DETAILED DESCRIPTION OF THE INVENTION

Aspects of the present invention include compounds of Formula (I) wherein R is selected from phenyl, naphthyl, thienyl or benzothienyl.

Aspects of the present invention include compounds of Formula (I) wherein $R^1$ is selected from hydrogen, —$C_{1-6}$alkyl-$R^5$, —$C_{2-6}$alkenyl-$R^5$, —$C_{2-6}$alkynyl-$R^5$, -aryl-$R^6$, heterocyclyl-$R^6$ or -heteroaryl-$R^6$; wherein a heteroaryl ring carbon atom forms the point of attachment to the indole nitrogen atom.

Another aspect of the present invention includes compounds of Formula (I) wherein $R^1$ is selected from hydrogen, —$C_{1-4}$alkyl-$R^5$, —$C_{2-4}$alkenyl-$R^5$, —$C_{2-6}$alkynyl-$R^5$, -phenyl-$R^6$, -naphthyl-$R^6$, -pyridinyl-$R^6$, -pyrimidinyl-$R^6$, -quinolinyl-$R^6$ or -benzothienyl-$R^6$; wherein a pyridinyl, pyrimidinyl, quinolinyl or benzothienyl ring carbon atom forms the point of attachment to the indole nitrogen atom.

Aspects of the present invention include compounds of Formula (I) wherein $R^5$ is 1 to 2 substituents independently selected from hydrogen, —O—($C_{1-4}$)alkyl, —O—($C_{1-4}$) alkyl-OH, —O—($C_{1-4}$)alkyl-O—($C_{1-4}$)alkyl, —O—($C_{1-4}$) alkyl-$NH_2$, —O—($C_{1-4}$)alkyl-NH($C_{1-4}$alkyl), —O—($C_{1-4}$) alkyl-N($C_{1-4}$alkyl)$_2$, —O—($C_{1-4}$)alkyl-S—($C_{1-4}$)alkyl, —O—($C_{1-4}$)alkyl-$SO_2$—($C_{1-4}$)alkyl, —O—($C_{1-4}$)alkyl-$SO_2$—$NH_2$, —O—($C_{1-4}$)alkyl-$SO_2$—NH($C_{1-4}$alkyl), —O—($C_{1-4}$)alkyl-$SO_2$—N($C_{1-4}$alkyl)$_2$, —O—C(O)H, —O—C(O)—($C_{1-4}$)alkyl, —O—C(O)—$NH_2$, —O—C(O)—NH($C_{1-4}$alkyl), —O—C(O)—N($C_{1-4}$alkyl)$_2$, —O—($C_{1-4}$)alkyl-C(O)H, —O—($C_{1-4}$)alkyl-C(O)—($C_{1-4}$)alkyl, —O—($C_{1-4}$)alkyl-$CO_2$H, —O—($C_{1-4}$)alkyl-C(O)—O—($C_{1-4}$) alkyl, —O—($C_{1-4}$)alkyl-C(O)—$NH_2$, —O—($C_{1-4}$) alkyl-C(O)—NH($C_{1-4}$alkyl), —O—($C_{1-4}$)alkyl-C(O)—N($C_{1-4}$ alkyl)$_2$, —C(O)H, —C(O)—($C_{1-4}$)alkyl, —$CO_2$H, —C(O)—O—($C_{1-4}$)alkyl, —C(O)—$NH_2$, —C(NH)—$NH_2$, —C(O)—NH($C_{1-4}$alkyl), —C(O)—N($C_{1-4}$alkyl)$_2$, —SH, —S—($C_{1-4}$)alkyl, —S—($C_{1-4}$)alkyl-S—($C_{1-4}$)alkyl, —S—($C_{1-4}$)alkyl-O—($C_{1-4}$)alkyl, —S—($C_{1-4}$)alkyl-O—($C_{1-4}$) alkyl-OH, —S—($C_{1-4}$)alkyl-O—($C_{1-4}$)alkyl-$NH_2$, —S—($C_{1-4}$)alkyl-O—($C_{1-4}$)alkyl-NH($C_{1-4}$alkyl), —S—($C_{1-4}$) alkyl-O—($C_{1-4}$)alkyl-N($C_{1-4}$alkyl)$_2$, —S—($C_{1-4}$)alkyl-NH ($C_{1-4}$alkyl), —$SO_2$—($C_{1-4}$)alkyl, —$SO_2$—$NH_2$, —$SO_2$—NH($C_{1-4}$alkyl), —$SO_2$—N($C_{1-4}$alkyl)$_2$, —N—$R^7$, —($C_{1-4}$) alkyl-N—$R^7$, cyano, (halo)$_{1-3}$, hydroxy, nitro, oxo, -cycloalkyl-$R^6$, —($C_{1-4}$)alkyl-cycloalkyl-$R^6$, -heterocyclyl-$R^6$, —($C_{1-4}$)alkyl-heterocyclyl-$R^6$, -aryl-$R^6$, —($C_{1-4}$)alkyl-aryl-$R^6$, -heteroaryl-$R^6$ or —($C_{1-4}$)alkyl-heteroaryl-$R^6$.

Another aspect of the present invention includes compounds of Formula (I) wherein $R^5$ is 1 to 2 substituents independently selected from hydrogen, —O—($C_{1-4}$)alkyl, —C(O)H, —N—$R^7$, —($C_{1-4}$)alkyl-N—$R^7$, hydroxy, -heterocyclyl-$R^6$ or —($C_{1-4}$)alkyl-heterocyclyl-$R^6$.

A further aspect of the present invention includes compounds of Formula (I) wherein $R^5$ is 1 to 2 substituents independently selected from hydrogen, —O—($C_{1-4}$)alkyl, —C(O)H, —N—$R^7$, —($C_{1-4}$)alkyl-N—$R^7$, hydroxy, -pyrrolidinyl-$R^6$, -morpholinyl-$R^6$, -thiazolidinyl-$R^6$, —($C_{1-4}$) alkyl-piperidinyl-$R^6$ or -piperazinyl-$R^6$.

Aspects of the present invention include compounds of Formula (I) wherein $R^6$ is 1 to 4 substituents attached to a carbon or nitrogen atom independently selected from hydrogen, —$C_{1-4}$alkyl, —($C_{1-4}$)alkyl-(halo)$_{1-3}$ or —($C_{1-4}$)alkyl-OH;
with the proviso that, when $R^6$ is attached to a carbon atom, $R^6$ is further selected from —$C_{1-4}$alkoxy, —C(O)$NH_2$, —$NH_2$, —NH($C_{1-4}$alkyl), —N($C_{1-4}$alkyl)$_2$, cyano, halo, —($C_{1-4}$)alkoxy-(halo)$_{1-3}$, hydroxy or nitro.

Another aspect of the present invention includes compounds of Formula (I) wherein $R^6$ is 1 to 4 substituents attached to a carbon or nitrogen atom independently selected from hydrogen or —$C_{1-4}$alkyl; with the proviso that, when $R^6$ is attached to a carbon atom, $R^6$ is further selected from halo.

Aspects of the present invention include compounds of Formula (I) wherein $R^7$ is 2 substituents independently selected from hydrogen, —$C_{1-6}$alkyl, —$C_{2-6}$alkenyl, —$C_{2-6}$ alkynyl, —($C_{1-4}$)alkyl-OH, —($C_{1-4}$)alkyl-O—($C_{1-4}$)alkyl, —($C_{1-4}$)alkyl-$NH_2$, —($C_{1-4}$)alkyl-NH($C_{1-6}$alkyl), —($C_{1-4}$) alkyl-N($C_{1-6}$alkyl)$_2$, —($C_{1-4}$)alkyl-S—($C_{1-4}$)alkyl, —C(O)-($C_{1-4}$)alkyl, —C(O)—O—($C_{1-4}$)alkyl, —C(O)—$NH_2$, —C(O)—NH($C_{1-6}$alkyl), —C(O)—N($C_{1-6}$alkyl)$_2$, —$SO_2$—($C_{1-4}$)alkyl, —$SO_2$—$NH_2$, —$SO_2$—NH($C_{1-6}$alkyl), —$SO_2$—N($C_{1-6}$alkyl)$_2$, —C(N)—$NH_2$, -cycloalkyl-$R^8$, —($C_{1-4}$)alkyl-heterocyclyl-$R^8$, -aryl-$R^8$, —($C_{1-4}$)alkyl-aryl-$R^8$ or —($C_{1-4}$)alkyl-heteroaryl-$R^8$.

Another aspect of the present invention includes compounds of Formula (I) wherein $R^7$ is 2 substituents independently selected from hydrogen, —$C_{1-6}$alkyl, —$C_{2-6}$alkenyl, —$C_{2-6}$alkynyl, —($C_{1-4}$)alkyl-OH, —($C_{1-4}$)alkyl-N($C_{1-6}$ alkyl)$_2$ or —($C_{1-4}$)alkyl-heteroaryl-$R^8$.

A further aspect of the present invention includes compounds of Formula (I) wherein $R^7$ is 2 substituents independently selected from hydrogen, —$C_{1-6}$alkyl, —$C_{2-6}$alkenyl, —$C_{2-6}$alkynyl, —($C_{1-4}$)alkyl-OH, —($C_{1-4}$)alkyl-N($C_{1-6}$ alkyl)$_2$ or —($C_{1-4}$)alkyl-furyl-$R^8$.

Aspects of the present invention include compounds of Formula (I) wherein $R^8$ is 1 to 4 substituents attached to a carbon or nitrogen atom independently selected from hydrogen, —$C_{1-4}$alkyl, —($C_{1-4}$)alkyl-(halo)$_{1-3}$ or —($C_{1-4}$)alkyl-OH;
with the proviso that, when $R^8$ is attached to a carbon atom, $R^8$ is further selected from —$C_{1-4}$alkoxy, —$NH_2$, —NH($C_{1-4}$alkyl), —N($C_{1-4}$alkyl)$_2$, cyano, halo, —($C_{1-4}$) alkoxy-(halo)$_{1-3}$, hydroxy or nitro.

Another aspect of the present invention includes compounds of Formula (I) wherein $R^8$ is 1 to 4 substituents attached to a carbon or nitrogen atom independently selected from hydrogen or —$C_{1-4}$alkyl.

Aspects of the present invention include compounds of Formula (I) wherein $R^2$ is one substituent attached to a carbon or nitrogen atom selected from hydrogen, —$C_{1-4}$ alkyl-$R^5$, —$C_{2-4}$alkenyl-$R^5$, —$C_{2-4}$alkynyl-$R^5$, —C(O)H, —C(O)—($C_{1-4}$)alkyl-$R^9$, —C(O)—$NH_2$, —C(O)—NH ($C_{1-4}$ alkyl-$R^9$), —C(O)—N($C_{1-4}$alkyl-$R^9$)$_2$, —C(O)—NH (aryl-$R^8$), —C(O)-cycloalkyl-$R^8$, —C(O)-heterocyclyl-$R^8$, —C(O)-aryl-$R^8$, —C(O)-heteroaryl-$R^8$, —$CO_2$H, —C(O)—O—($C_{1-4}$)alkyl-$R^9$, —C(O)—O-aryl-$R^8$, —$SO_2$—($C_{1-4}$)alkyl-$R^9$, —$SO_2$-aryl-$R^8$, -cycloalkyl-$R^6$, -aryl-$R^8$ or —($C_{1-4}$)alkyl-N—$R^7$;
with the proviso that, when $R^2$ is attached to a carbon atom, R is further selected from —$C_{1-4}$alkoxy-$R^5$, —N—$R^7$, cyano, halogen, hydroxy, nitro, oxo (wherein oxo is attached to a saturated carbon atom), -heterocyclyl-$R^6$ or -heteroaryl-$R^6$.

Another aspect of the present invention includes compounds of Formula (I) wherein $R^2$ is one substituent attached to a carbon or nitrogen atom selected from hydrogen or —$C_{1-4}$alkyl-$R^5$; with the proviso that, when $R^2$ is attached to a carbon atom, $R^2$ is further selected from —$C_{1-4}$alkoxy-$R^5$, halogen or hydroxy.

A further aspect of the present invention includes compounds of Formula (I) wherein $R^2$ is one substituent attached to a carbon or nitrogen atom selected from hydrogen or —$C_{1-4}$alkyl-$R^5$; with the proviso that, when $R^2$ is attached to a carbon atom, $R^2$ is further selected from —$C_{1-4}$alkoxy-$R^5$, bromine, iodine or hydroxy.

Aspects of the present invention include compounds of Formula (I) wherein $R^9$ is 1 to 2 substituents independently selected from hydrogen, —$C_{1-4}$alkoxy, —$NH_2$, —$NH(C_{1-4}$alkyl), —$N(C_{1-4}$alkyl$)_2$, cyano, (halo)$_{1-3}$, hydroxy or nitro.

Another aspect of the present invention includes compounds of Formula (I) wherein $R^9$ is hydrogen.

Aspects of the present invention include compounds of Formula (I) wherein $R^3$ is 1 to 4 substituents attached to a carbon atom independently selected from hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$)alkyl-$R^9$, —C(O)—$NH_2$, —C(O)—NH($C_{1-4}$alkyl-$R^9$), —C(O)—N($C_{1-4}$alkyl-$R^9)_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O—($C_{1-4}$)alkyl-$R^9$, —C(O)—O-aryl-$R^8$, —$SO_2$—($C_{1-4}$)alkyl-$R^9$, —$SO_2$-aryl-$R^8$, —N—$R^7$, —($C_{1-4}$)alkyl-N—$R^7$, cyano, halogen, hydroxy, nitro, -cycloalkyl-$R^8$, -heterocyclyl-$R^8$, -aryl-$R^8$ or -heteroaryl-$R^8$.

Another aspect of the present invention includes compounds of Formula (I) wherein $R^3$ is 1 to 4 substituents attached to a carbon atom independently selected from hydrogen or halogen.

A further aspect of the present invention includes compounds of Formula (I) wherein $R^3$ is hydrogen.

Aspects of the present invention include compounds of Formula (I) wherein $R^4$ is 1 to 4 substituents attached to a carbon atom independently selected from hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$)alkyl-$R^9$, —C(O)—$NH_2$, —C(O)—NH($C_{1-4}$alkyl-$R^9$), —C(O)—N($C_{1-4}$alkyl-$R^9)_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O-($C_{1-4}$)alkyl-$R^9$, —C(O)—O-aryl-$R^8$, —SH, —S—($C_{14}$)alkyl-$R^{10}$, —$SO_2$—($C_{1-4}$)alkyl-$R^9$, —$SO_2$-aryl-$R^8$, —$SO_2$—$NH_2$, —$SO_2$—NH($C_{1-4}$alkyl-$R^9$), —$SO_2$—N($C_{1-4}$alkyl-$R^9)_2$, —N—$R^7$, —($C_{1-4}$)alkyl-N—$R^7$, cyano, halogen, hydroxy, nitro, -cycloalkyl-$R^8$, -heterocyclyl-$R^8$, -aryl-$R^8$ or -heteroaryl-$R^8$.

Another aspect of the present invention includes compounds of Formula (T) wherein $R^4$ is 1 to 4 substituents attached to a carbon atom independently selected from hydrogen, —$C_{1-4}$alkyl-$R^{10}$ or halogen.

A further aspect of the present invention includes compounds of Formula (T) wherein $R^4$ is 1 to 4 substituents attached to a carbon atom independently selected from hydrogen, —$C_{1-4}$alkyl-$R^{10}$ or chlorine.

Aspects of the present invention include compounds of Formula (I) wherein $R^{10}$ is 1 to 2 substituents independently selected from hydrogen, —$NH_2$, —NH($C_{1-4}$alkyl), —N($C_{1-4}$alkyl$)_2$, cyano, (halo)$_{1-3}$, hydroxy, nitro or oxo.

Another aspect of the present invention includes compounds of Formula (I) wherein $R^{10}$ is hydrogen.

Aspects of the present invention include compounds of Formula (I) wherein $R^{11}$ is selected from hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, -aryl-$R^8$, -heteroaryl-$R^8$ or halogen.

Another aspect of the present invention includes compounds of Formula (I) wherein $R^{11}$ is hydrogen.

In yet another aspect of the present invention when X is CH and R is phenyl, naphthyl, primidinyl or quinolinyl; $R^1$ is —$C_{1-8}$alkyl-$R^5$, —$C_{2-8}$alkenyl-$R^5$, —$C_{2-8}$alkynyl-$R^5$, -napthyl-$R^6$ or -heteroaryl-$R^6$; wherein a heteroaryl ring carbon atom forms the point of attachment to the indole nitrogen atom; wherein $R^5$ for the —$C_{1-8}$alkyl-$R^5$ is substituted with H, OH, $NH_2$, $NHC_{1-8}$alkyl, or N(di-$C_{1-8}$alkyl$)_2$. Preferably when X is CH and R is phenyl, naphthyl, primidinyl or quinolinyl; $R^1$ is —$C_{1-8}$alkyl-$NR^7$, —$C_{2-8}$alkenyl-$R^5$, —$C_{2-8}$alkynyl-$R^5$, -napthyl-$R^6$ or -heteroaryl-$R^6$; wherein a heteroaryl ring carbon atom forms the point of attachment to the indole nitrogen atom; wherein both $R^7$ substituents of —$C_{1-8}$alkyl-$NR^7$ are not H, —$C_{1-18}$ alkyl or a combination thereof. Most preferably when X is CH and R is phenyl, naphthyl, primidinyl or quinolinyl; $R^1$ is —$C_{2-8}$alkenyl-$R^5$, —$C_{2-8}$alkynyl-$R^5$ or -heteroaryl-$R^6$, wherein a heteroaryl ring carbon atom forms the point of attachment to the indole nitrogen atom.

Exemplified compounds of Formula (I) include compounds selected from Formula (Ia):

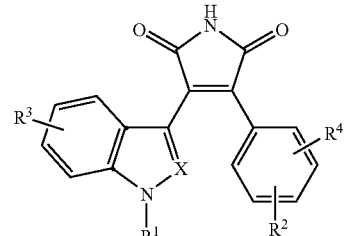

Formula (Ia)

wherein $R^1$, $R^2$, $R^4$ and X are dependently selected from

| Cpd | $R^1$ | $R^2$ | $R^3$ | $R^4$ | X |
|---|---|---|---|---|---|
| 1 | —CH=$CH_2$ | 4-(—O—$CH_2$CH(OH)$CH_2$-1-piperidinyl) | H | H | CH; |
| 2 | —CH=$CH_2$ | 3-(—O—$CH_2$CH(OH)$CH_2$—N($CH_3)_2$) | H | H | CH; |
| 3 | —CH=$CH_2$ | 4-(—O—$CH_2$CH(OH)$CH_2$—N($CH_3)_2$) | H | H | CH; |
| 4 | —CH=$CH_2$ | 2-(—O—$CH_2$CH(OH)$CH_2$—N($CH_3)_2$) | H | H | CH; |
| 7 | —$CH_2$CH(—O$CH_2CH_3)_2$ | 2-(—O$CH_3$) | H | H | CH; |
| 8 | —$CH_2$C(O)H | 2-(—O$CH_3$) | H | H | CH; |

-continued

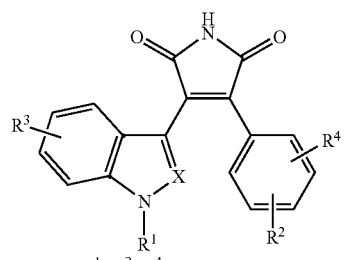

Formula (Ia)

wherein $R^1$, $R^2$, $R^4$ and X are dependently selected from

| Cpd | $R^1$ | $R^2$ | $R^3$ | $R^4$ | X |
|---|---|---|---|---|---|
| 9 | —(CH$_2$)$_2$—N(CH$_3$)((CH$_2$)$_2$—OH) | 2-(—OCH$_3$) | H | H | CH; |
| 10 | H | 4-(—O—CH$_2$CH$_2$—NHCH$_3$) | H | H | CH; |
| 11 | —(CH$_2$)$_3$—N(CH$_3$)(CH$_2$C≡CH) | 3-Br | H | H | CH; |
| 13 | 5-hexyn-1-yl | 3-Br | H | H | CH; |
| 14 | —(CH$_2$)$_3$—NH(CH$_3$) | 3-Br | H | H | CH; |
| 19 | —(CH$_2$)$_3$—N(CH$_3$)$_2$ | 4-(—O—CH$_2$CH(OH)CH$_2$—N(CH$_3$)$_2$) | H | H | CH; |
| 20 | —(CH$_2$)$_3$—N(CH$_3$)$_2$ | 2-(—O—CH$_2$CH(OH)CH$_2$—N(CH$_3$)$_2$) | H | H | CH; |
| 21 | —(CH$_2$)$_2$—OH | 2-(—O—CH$_2$CH(OH)CH$_2$—N(CH$_3$)$_2$) | H | H | CH; |
| 22 | —(CH$_2$)$_3$—N(CH$_3$)(3-butyn-1-yl) | 3-Br | H | H | CH; |
| 23 | —(CH$_2$)$_3$—N(CH$_3$)(3-butyn-1-yl) | 2-I | H | H | CH; |
| 24 | H | -5-(—O—(CH$_2$)$_3$—N(CH$_3$)$_2$) | H | 2-Br | CH; |
| 25 | Ph | -5-(—O—(CH$_2$)$_3$—N(CH$_3$)$_2$) | H | 2-Br | CH; |
| 26 | 4-pyrimidinyl | 2-(—OCH$_3$) | H | H | CH; |
| 27 | 3-pyridinyl | 2-(—OCH$_3$) | H | H | CH; |
| 28 | 3-pyridinyl | 2-OH | H | H | CH; |
| 29 | 3-pyridinyl | 4-OH | H | H | CH; |
| 53 | —(CH$_2$)$_3$—OH | H | H | H | N; |
| 54 | —(CH$_2$)$_3$—OH | 2-O—CH$_3$ | H | H | N; |
| 55 | tetrahydropyran-4-yl | 2-O—CH$_3$ | H | H | CH; |
| 56 | 5-carboxypyridin-3-yl | 2-O—CH$_3$ | 5-Cl | H | CH; |
| 57 | 5-methoxycarbonylpyridin-3-yl | 2-O—CH$_3$ | 5-Cl | H | CH; |
| 58 | 5-carbamoylpyridin-3-yl | 2-O—CH$_3$ | 5-Cl | H; | CH; | and pharmaceutically acceptable salts thereof.

Exemplified compounds of Formula (I) include compounds selected Formula (Ib):

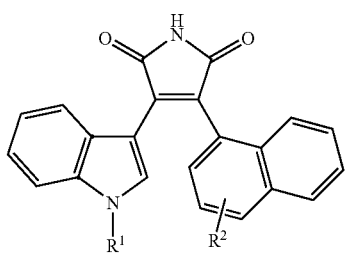

Formula (Ib)

wherein $R^1$ and $R^2$ are dependently selected from

| Cpd | $R^1$ | $R^2$ |
|---|---|---|
| 5 | —CH=CH$_2$ | 2-OH; |
| 6 | —CH=CH$_2$ | 2-(—O—CH$_2$CH(OH)CH$_2$—N(CH$_3$)$_2$); |
| 12 | —(CH$_2$)$_3$—N(CH$_3$)$_2$ | H; |
| 15 | H | 2-(—O—CH$_2$CH(OH)CH$_2$—N(CH$_3$)$_2$); |
| 16 | —(CH$_2$)$_2$—N(CH$_2$CH$_3$)$_2$ | H; |
| 17 | —(CH$_2$)$_2$—N(CH$_3$)(2-butyn-1-yl) | H; |
| 18 | —(CH$_2$)$_2$—N(CH$_3$)(3-butyn-1-yl) | H; |
| 30 | 5-pyrimidinyl | H; | and pharmaceutically acceptable salts thereof.

Exemplified compounds of Formula (I) include compounds selected from Formula (Ic):

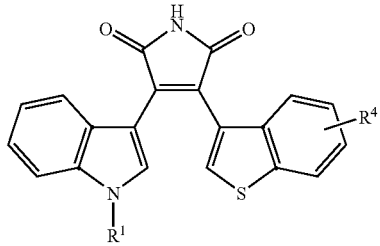

Formula (Ic)

wherein R¹ and R⁴ are dependently selected from

| Cpd | R¹ | R⁴ |
|---|---|---|
| 31 | —(CH$_2$)$_3$—N(CH$_3$)$_2$ | 5-Cl; |
| 32 | —(CH$_2$)$_3$—N(CH$_3$)$_2$ | H; |
| 33 | —(CH$_2$)$_2$—N(CH$_3$)(CH$_2$C≡CH) | 5-Cl; |
| 34 | —(CH$_2$)$_2$—N(CH$_3$)(2-butyn-1-yl) | 5-Cl; |
| 35 | —(CH$_2$)$_2$—N(CH$_3$)(3-butyn-1-yl) | 5-Cl; |
| 36 | —CH$_2$CH(—O—CH$_2$CH$_3$)$_2$ | 5-Cl; |
| 37 | —CH$_2$C(O)H | 5-Cl; |
| 38 | —(CH$_2$)$_2$—N(CH$_3$)$_2$ | 5-Cl; |
| 39 | —(CH$_2$)$_2$—N(CH$_3$)((CH$_2$)$_2$—N(CH$_3$)$_2$) | 5-Cl; |
| 40 | —(CH$_2$)$_3$-1-(4-(CH$_3$)-piperazinyl) | 5-Cl; |
| 41 | —(CH$_2$)$_2$—N(CH$_3$)((CH$_2$)$_2$—OH) | 5-Cl; |
| 42 | —(CH$_2$)$_2$-4-morpholinyl | 5-Cl; |
| 43 | —(CH$_2$)$_2$-1-pyrrolidinyl | 5-Cl; |
| 44 | —(CH$_2$)$_2$—N(CH$_2$CH$_3$)$_2$ | 5-Cl; |
| 45 | —(CH$_2$)$_2$—N(CH$_3$)(CH$_2$-2-furyl) | 5-Cl; |
| 46 | —(CH$_2$)$_2$-1-thiazolidinyl | 5-Cl; |
| 47 | —(CH$_2$)$_3$—N(CH$_3$)(CH$_2$CH=CH$_2$) | 5-Cl; |
| 48 | —(CH$_2$)$_3$—OH | 5-Cl; |
| 49 | —(CH$_2$)$_3$—N(CH$_3$)$_2$ | 2,5-Cl$_2$; |
| 50 | —(CH$_2$)$_3$—N(CH$_3$)(CH$_2$CH=CH$_2$) | 2,5-Cl$_2$; |
| 51 | (5-Br)-2-pyridinyl | 5-Cl; | and pharmaceutically acceptable salts thereof.

Exemplified compounds of Formula (I) include compounds selected from Formula (Id):

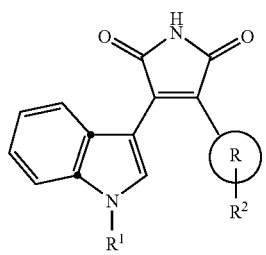

Formula (Id)

wherein R, R¹ and R² are dependently selected from

| Cpd | R | R¹ | R² |
|---|---|---|---|
| 52 | 2-thienyl | 3-pyridinyl | H; | and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (Ref. International J. Pharm. 1986, 33, 201–217; J. Pharm. Sci., 1977, January, 66(1), p 1) include pharmaceutically acceptable acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isothionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their pharmaceutically acceptable salts. Organic or inorganic acids also include, and are not limited to, hydroiodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M.

Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched chain consisting solely of 2–8 hydrogen substituted carbon atoms that contains at least one double bond. The term "alkynyl" refers to a partially unsaturated straight or branched chain consisting solely of 2–8 hydrogen substituted carbon atoms that contains at least one triple bond. The term "alkoxy" refers to —O-alkyl, where alkyl is as defined supra. The term "alkyl-OH" refers to radicals wherein the alkyl chain terminates with a hydroxy radical, where alkyl is as previously defined. The term "oxo" refers to a =O radical optionally attached within the alkyl chain. Unless specifically indicated otherwise, alkyl, alkenyl and alkynyl chains may be optionally substituted within the alkyl chain or on a terminal carbon atom.

The term "cycloalkyl" refers to a saturated or partially unsaturated monocyclic alkyl ring consisting of 3–8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclopentenyl (containing one double bond), cyclopentynyl (containing one triple bond), cyclohexyl, cyclohexenyl (containing at least one double bond), cyclohexynyl (containing at least one triple bond), cycloheptenyl (containing at least one double bond) or cycloheptynyl (containing at least one triple bond).

The term "heterocyclyl" as used herein refers to an unsubstituted or substituted stable three to seven membered monocyclic saturated or partially unsaturated ring system which consists of carbon atoms and from one to three heteroatoms selected from N, O or S, or a stable eight to eleven membered bicyclic saturated or partially saturated ring system which consists of carbon atoms and from one to four heteroatoms selected from N, O, or S. In either the monocyclic or bicyclic rings the nitrogen or sulfur heteroatoms may optionally be oxidized, and the nitrogen heteroatom may optionally be quaternized. Preferred are saturated or partially unsaturated rings having five or six members of which at least one member is a N, O or S atom and which optionally contains one additional N, O or S atoms; saturated or partially unsaturated bicyclic rings having nine or ten members of which at least one member is a N, O or S atom and which optionally contains one or two additional N, O or S atoms; wherein said nine or ten membered bicyclic rings may have one aromatic ring and one nonaromatic ring. In another embodiment of this invention the previously defined heterocyclyl have as the additional heteroatom N, wherein at most two nitrogens atoms are adjacent. Examples include, and are not limited to, pyrrolinyl, pyrrolidinyl, 1,3-dioxolanyl, imidazolinyl, imidazolidinyl, pyrazolinyl, pyrazolidinyl, thiazolidinyl, piperidinyl, morpholinyl or piperazinyl.

The term "aryl" refers to an aromatic monocyclic ring containing carbon and hydrogen, such as a carbon ring containing 6 carbon atom with hydrogen atoms substituted thereon, an aromatic bicyclic ring system containing 10 carbon atoms with hydrogen substituted thereon or an aromatic tricyclic ring system containing 14 carbon atoms with hydrogen atoms substituted thereon. Also included within the scope of the definition of aryl are bicyclic and tricyclic ring systems (containing carbon and hydrogen) wherein only one of the rings is aromatic such as tetrahydronaphthalene and indane. The hydrogen atoms on the monocyclic, bicyclic and tricyclic rings may be replaced with other groups or subsitutents as indicated. Examples include, and are not limited to, phenyl, naphthalenyl or anthracenyl.

The term "heteroaryl" as used herein represents an unsubstituted or substituted stable five or six membered monocyclic heteroaromatic ring system or an unsubstituted or substituted stable nine or ten membered bicyclic heteroaromatic ring system and unsubstituted or substituted stable twelve to fourteen membered tricyclic ring systems which consists of carbon atoms and from one to four heteroatoms selected from N, O or S, and wherein the nitrogen heteroatom of any of these heteroaryls may optionally be oxidized, or may optionally be quaternized. Preferred heteroaryl are aromatic monocyclic rings containing five members of which at least one member is a N, O or S atom and which optionally contains one, two or three additional N atoms; an aromatic monocyclic ring having six members of which one, two or three members are a N atoms; an aromatic bicyclic ring having nine members of which at least one member is a N, O or S atom and which optionally contains one, two or three additional N atoms; an aromatic bicyclic ring having ten members of which of which one, two, three or four members are N atoms; or, an aromatic tricyclic ring system containing 13 members of which at least one member is a N, O or S atom and which optionally contains one, two or three additional N atoms. In another embodiment of this invention, the previously defined heteroaryls have as the additional heteroatom N, wherein at most four nitrogens atoms are adjacent. Examples include, and are not limited to, furyl, thienyl, pyrrolyl, oxazolyl, thiazolyl, imidazolyl, triazolyl, tetrazolyl, pyrazolyl, isoxazolyl, isothiazolyl, pyridinyl, pyridazinyl, pyrimidinyl, pyrazinyl, indolyl, indazolyl, benzo(b)thienyl, quinolinyl, isoquinolinyl or quinazolinyl.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

Under standard nomenclature rules used throughout this disclosure, the terminal portion of the designated side chain is described first followed by the adjacent functionality toward the point of attachment. Thus, for example, a "phenyl$C_{1-6}$alkylamido$C_{1-6}$alkyl" substituent refers to a group of the formula:

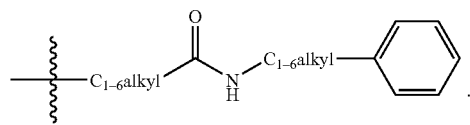

A substituent's point of attachment may also be indicated by a dashed line to indicate the point(s) of attachment, followed by the adjacent functionality and ending with the terminal functionality such as, for example, —($C_{1-6}$)alkyl-NH—($C_{1-6}$)alkyl-phenyl.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An aspect of the invention is a pharmaceutical composition comprising a pharmaceutically acceptable carrier and any of the compounds described above. Illustrative of the invention is a pharmaceutical composition made by mixing any of the compounds described above and a pharmaceutically acceptable carrier. Another illustration of the invention is a process for making a pharmaceutical composition comprising mixing any of the compounds described above and a pharmaceutically acceptable carrier. Further illustrative of the present invention are pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase or dual-kinase inhibitors useful in a method for treating or ameliorating a kinase or dual-kinase mediated disorder. In particular, the kinase is selected from protein kinase C or glycogen synthase kinase-3. More particularly, the kinase is selected from protein kinase C α, protein kinase C β-II, protein kinase C γ or glycogen synthase kinase-3β.

Protein Kinase C Isoforms

Protein kinase C is known to play a key role in intracellular signal transduction (cell-cell signaling), gene expression and in the control of cell differentiation and growth. The PKC family is composed of twelve isoforms that are further classified into 3 subfamilies: the calcium dependent classical PKC isoforms alpha (α), beta-I (β-I), beta-II (β-II) and gamma (γ); the calcium independent PKC isoforms delta (δ), epsilon (ε), eta (η), theta (θ) and mu (μ); and, the a typical PKC isoforms zeta (ζ), lambda (λ) and iota (ι).

Certain disease states tend to be associated with elevation of particular PKC isoforms. The PKC isoforms exhibit distinct tissue distribution, subcellular localization and activation-dependent cofactors. For example, the α and β isoforms of PKC are selectively induced in vascular cells stimulated with agonists such as vascular endothelial growth factor (VEGF) (P. Xia, et al., *J. Clin. Invest.*, 1996, 98, 2018) and have been implicated in cellular growth, differentiation, and vascular permeability (H. Ishii, et al., *J. Mol. Med.*, 1998, 76, 21). The elevated blood glucose levels found in diabetes leads to an isoform-specific elevation of the β-II isoform in vascular tissues (Inoguchi, et al., *Proc. Natl. Acad. Sci. USA*, 1992, 89, 11059–11065). A diabetes-linked elevation of the β isoform in human platelets has been correlated with their altered response to agonists (Bastyr III, E. J. and Lu, J., *Diabetes*, 1993, 42, (Suppl. 1) 97A). The human vitamin D receptor has been shown to be selectively phosphorylated by PKCβ. This phosphorylation has been linked to alterations in the functioning of the receptor (Hsieh, et al., *Proc. Natl. Acad. Sci. USA*, 1991, 88, 9315–9319; Hsieh, et al., *J. Biol. Chem.*, 1993, 268, 15118–15126). In addition, the work has shown that the β-II isoform is responsible for erythroleukemia cell proliferation while the α isoform is involved in megakaryocyte differentiation in these same cells (Murray, et al., *J. Biol. Chem.*, 1993, 268, 15847–15853).

Cardiovascular Diseases

PKC activity plays an important role in cardiovascular diseases. Increased PKC activity in the vasculature has been shown to cause increased vasoconstriction and hypertension (Bilder, G. E., et al., *J. Pharmacol. Exp. Ther.*, 1990, 252, 526–530). PKC inhibitors block agonist-induced smooth muscle cell proliferation (Matsumoto, H. and Sasaki, Y., *Biochem. Biophys. Res. Commun.*, 1989, 158, 105–109). PKC β triggers events leading to induction of Egr-1 (Early Growth Factor-1) and tissue factor under hypoxic conditions (as part of the oxygen deprivation-mediated pathway for triggering procoagulant events) (Yan, S-F, et al., *J. Biol. Chem.*, 2000, 275, 16, 11921–11928). PKC β is suggested as a mediator for production of PAI-1 (Plaminogen Activator Inhibitor-1) and is implicated in the development of thrombosis and atherosclerosis (Ren, S, et al., *Am. J. Physiol.*, 2000, 278, (4, Pt. 1), E656–E662). PKC inhibitors are useful in treating cardiovascular ischemia and improving cardiac function following ischemia (Muid, R. E., et al., *FEBS Lett.*, 1990, 293,169–172; Sonoki, H. et al., *Kokyu-To Junkan*, 1989, 37, 669–674). Elevated PKC levels have been correlated with an increased platelet function response to agonists (Bastyr III, E. J. and Lu, J., *Diabetes*, 1993, 42, (Suppl. 1) 97A). PKC has been implicated in the biochemical pathway in the platelet-activating factor (PAF) modulation of microvascular permeability (Kobayashi, et al., *Amer. Phys. Soc.*, 1994, H1214–H1220). PKC inhibitors affect agonist-induced aggregation in platelets (Toullec, D., et al., *J. Biol. Chem.*, 1991, 266, 15771–15781). Accordingly, PKC inhibitors may be indicated for use in treating cardiovascular disease, ischemia, thrombotic conditions, atherosclerosis and restenosis.

Diabetes

Excessive activity of PKC has been linked to insulin signaling defects and therefore to the insulin resistance seen in Type II diabetes (Karasik, A., et al., *J. Biol. Chem.*, 1990, 265, 10226–10231; Chen, K. S., et al., *Trans. Assoc. Am. Physicians*, 1991, 104, 206–212; Chin, J. E., et al., *J. Biol. Chem.*, 1993, 268, 6338–6347).

Diabetes-Associated Disorders

Studies have demonstrated an increase in PKC activity in tissues known to be susceptible to diabetic complications when exposed to hyperglycemic conditions (Lee, T-S., et al., *J. Clin. Invest.*, 1989, 83, 90–94; Lee, T-S., et al., *Proc. Natl. Acad. Sci. USA*, 1989, 86, 5141–5145; Craven, P. A. and DeRubertis, F. R., *J. Clin. Invest.*, 1989, 87, 1667–1675; Wolf, B. A., et al., *J. Clin. Invest.*, 1991, 87, 31–38; Tesfamariam, B., et al., *J. Clin. Invest.*, 1991, 87, 1643–1648). For example, activation of the PKC-β-II isoform plays an important role in diabetic vascular complications such as retinopathy (Ishii, H., et al., *Science*, 1996, 272, 728–731) and PKCβ has been implicated in development of the cardiac hypertrophy associated with heart failure (X. Gu, et al., *Circ. Res.*, 1994, 75, 926; R. H. Strasser, et al., *Circulation*, 1996, 94, 1551). Overexpression of cardiac PKCβII in transgenic mice caused cardiomyopathy involving hypertrophy, fibrosis and decreased left ventricular function (H. Wakasaki, et al., *Proc. Natl. Acad. Sci. USA*, 1997, 94, 9320).

Inflammatory Diseases

PKC inhibitors block inflammatory responses such as the neutrophil oxidative burst, CD3 down-regulation in T-lymphocytes and phorbol-induced paw edema (Twoemy, B., et al., *Biochem. Biophys. Res. Commun.*, 1990, 171, 1087–1092; Mulqueen, M. J., et al. *Agents Actions*, 1992, 37, 85–89). PKC β, has an essential role in the degranulation of bone marrow-derived mast cells, thus affecting cell capacity to produce IL-6 (Interleukin-6) (Nechushtan, H., et al., *Blood*, 2000 (March), 95, 5, 1752–1757). PKC plays a role in enhanced ASM (Airway Smooth Muscle) cell growth in rat models of two potential risks for asthma: hyperresponsiveness to contractile agonists and to growth stimuli (Ren, S, et al., *Am. J. Physiol.*, 2000, 278, (4, Pt. 1), E656–E662). PKC β-1 overexpression augments an increase in endothelial permeability, suggesting an important function in the regulation of the endothelial barrier (Nagpala, P. G., et al., *J. Cell Physiol.*, 1996, 2, 249–55). PKC β mediates activation of neutrophil NADPH oxidase by PMA and by stimulation of Fcγ receptors in neutrophils (Dekker, L. V., et al., *Biochem. J.*, 2000, 347, 285–289). Thus, PKC inhibitors may be indicated for use in treating inflammation and asthma.

Immunological Disorders

PKC may be useful in treating or ameliorating certain immunological disorders. While one study suggests that HCMV (Human Cytomegalovirus) inhibition is not correlated with PKC inhibition (Slater, M. J., et al., *Biorg. & Med. Chem.*, 1999, 7, 1067–1074), another study showed that the PKC signal transduction pathway synergistically interacted with the cAMP-dependent PKA pathway to activate or increase HIV-1 transcription and viral replication and was abrogated with a PKC inhibitor (Rabbi, M. F., et al., *Virology*, 1998 (June 5), 245, 2, 257–69). Therefore, an immunological disorder may be treated or ameliorated as a function of the affected underlying pathway's response to up- or down-regulation of PKC.

PKC β deficiency also results in an immunodeficiency characterized by impaired humoral immune responses and a reduced B cell response, similar to X-linked immunodeficiency in mice, playing an important role in antigen receptor-mediated signal transduction (Leitges, M., et al., *Science* (Wash., D.C.), 1996, 273, 5276, 788–789). Accordingly, transplant tissue rejection may be ameliorated or prevented by suppressing the immune response using a PKC β inhibitor.

Dermatological Disorders

Abnormal activity of PKC has been linked to dermatological disorders characterized by abnormal proliferation of keratinocytes, such as psoriasis (Horn, F., et al., *J. Invest. Dermatol.*, 1987, 88, 220–222; Raynaud, F. and Evain-Brion, D., *Br. J. Dermatol.*, 1991, 124, 542–546). PKC inhibitors have been shown to inhibit keratinocyte proliferation in a dose-dependent manner (Hegemann, L., et al., *Arch. Dermatol. Res.*, 1991, 283, 456–460; Bollag, W. B., et al., *J. Invest. Dermatol.*, 1993, 100, 240–246).

Oncological Disorders

PKC activity has been associated with cell growth, tumor promotion and cancer (Rotenberg, S. A. and Weinstein, I. B., *Biochem. Mol. Aspects Sel. Cancer*, 1991, 1, 25–73; Ahmad, et al., *Molecular Pharmacology*, 1993, 43, 858–862); PKC inhibitors are known to be effective in preventing tumor growth in animals (Meyer, T., et al., *Int. J. Cancer*, 1989, 43, 851–856; Akinagaka, S., et al., *Cancer Res.*, 1991, 51, 4888–4892). PKC β-1 and β-2 expression in differentiated HD3 colon carcinoma cells blocked their differentiation, enabling them to proliferate in response to basic FGF (Fibroblast Growth Factor) like undifferentiated cells, increasing their growth rate and activating several MBP (Myelin-Basic Protein) kinases, including p57 MAP (Mitogen-Activated Protein) kinase (Sauma, S., et al., *Cell Growth Differ.*, 1996, 7, 5, 587–94). PKC α inhibitors, having an additive therapeutic effect in combination with other anti-cancer agents, inhibited the growth of lymphocytic leukemia cells (Konig, A., et al., *Blood*, 1997, 90, 10, Suppl. 1 Pt. 2). PKC inhibitors enhanced MMC (Mitomycin-C) induced apoptosis in a time-dependent fashion in a gastric cancer cell-line, potentially indicating use as agents for chemotherapy-induced apoptosis (Danso, D., et al., *Proc. Am. Assoc. Cancer Res.*, 1997, 38, 88 Meet., 92). Therefore, PKC inhibitors may be indicated for use in ameliorating cell and tumor growth, in treating or ameliorating cancers (such as leukemia or colon cancer) and as adjuncts to chemotherapy.

PKC α (by enhancing cell migration) may mediate some proangiogenic effects of PKC activation while PKC δ may direct antiangiogenic effects of overall PKC activation (by inhibiting cell growth and proliferation) in capillary endothelial cells, thus regulating endothelial proliferation and angiogenesis (Harrington, E. O., et al., *J. Biol. Chem.*, 1997, 272, 11, 7390–7397). PKC inhibitors inhibit cell growth and induce apoptosis in human glioblastoma cell lines, inhibit the growth of human astrocytoma xenografts and act as radiation sensitizers in glioblastoma cell lines (Begemann, M., et al., *Anticancer Res.* (*Greece*), 1998 (July–August), 18, 4A, 2275–82). PKC inhibitors, in combination with other anti-cancer agents, are radiation and chemosensitizers useful in cancer therapy (Teicher, B. A., et al., *Proc. Am. Assoc. Cancer Res.*, 1998, 39, 89 Meet., 384). PKC β inhibitors (by blocking the MAP kinase signal transduction pathways for VEGF (Vascular Endothelial Growth Factor) and bFGF (basic Fibrinogen Growth Factor) in endothelial cells), in a combination regimen with other anti-cancer agents, have an anti-angiogenic and antitumor effect in a human T98G glioblastoma multiforme xenograft model (Teicher, B. A., et al., *Clinical Cancer Research*, 2001 (March), 7, 634–640). Accordingly, PKC inhibitors may be indicated for use in ameliorating angiogenesis and in treating or ameliorating cancers (such as breast, brain, kidney, bladder, ovarian or colon cancers) and as adjuncts to chemotherapy and radiation therapy.

Central Nervous System Disorders

PKC activity plays a central role in the functioning of the central nervous system (CNS) (Huang, K. P., *Trends Neurosci.*, 1989, 12, 425–432) and PKC is implicated in Alzheimer's disease (Shimohama, S., et al., *Neurology*, 1993, 43, 1407–1413) and inhibitors have been shown to prevent the damage seen in focal and central ischemic brain injury and brain edema (Hara, H., et al., *J. Cereb. Blood Flow Metab.*, 1990, 10, 646–653; Shibata, S., et al., *Brain Res.*, 1992, 594, 290–294). Accordingly, PKC inhibitors may be indicated for use in treating Alzheimer's disease and in treating neurotraumatic and ischemia-related diseases.

The long-term increase in PKC γ (as a component of the phosphoinositide $2^{nd}$ messenger system) and muscarinic acetylcholine receptor expression in an amygdala-kindled rat model has been associated with epilepsy, serving as a basis for the rat's permanent state of hyperexcitability (Beldhuis, H. J. A., et al., *Neuroscience*, 1993, 55, 4, 965–73). Therefore, PKC inhibitors may be indicated for use in treating epilepsy.

The subcellular changes in content of the PKC γ and PKC β-II isoenzymes for animals in an in-vivo thermal hyperalgesia model suggests that peripheral nerve injury contributes to the development of persistent pain (Miletic, V., et al., *Neurosci. Lett.*, 2000, 288, 3, 199–202). Mice lacking PKC γ display normal responses to acute pain stimuli, but almost completely fail to develop a neuropathic pain syndrome after partial sciatic nerve section (Chen, C., et al., *Science (Wash., D.C.)*, 1997, 278, 5336, 279–283). PKC modulation may thus be indicated for use in treating chronic pain and neuropathic pain.

PKC has demonstrated a role in the pathology of conditions such as, but not limited to, cardiovascular diseases, diabetes, diabetes-associated disorders, inflammatory diseases, immunological disorders, dermatological disorders, oncological disorders and central nervous system disorders.

Glycogen Synthase Kinase-3

Glycogen synthase kinase-3 (GSK-3) is a serine/threonine protein kinase composed of two isoforms (α and β) which are encoded by distinct genes. GSK-3 is one of several protein kinases which phosphorylate glycogen synthase (GS) (Embi, et al., *Eur. J. Biochem*, 1980, 107, 519–527). The α and β isoforms have a monomeric structure of 49 and 47 kD respectively and are both found in mammalian cells. Both isoforms phosphorylate muscle glycogen synthase (Cross, et al., *Biochemical Journal*, 1994, 303, 21–26) and these two isoforms show good homology between species (human and rabbit GSK-3α are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake and in this tissue glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Larner J., *Biochim. Biophys. Acta*, 1960, 39, 171–173, Parker P. J., et al., *Eur. J. Biochem.*, 1983, 130, 227–234, and Cohen P., *Biochem. Soc. Trans.*, 1993, 21, 555–567). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A. K. and Pandey S. K., *Mol. and Cellular Biochem.*, 1998, 182, 135–141).

Studies suggest that an increase in GSK-3 activity might be important in Type II diabetic muscle (Chen, et al., *Diabetes*, 1994, 43, 1234–1241). Overexpression of GSK-3β and constitutively active GSK-3β (S9A, S9e) mutants in HEK-293 cells resulted in suppression of glycogen synthase activity (Eldar-Finkelman, et al., *PNAS*, 1996, 93, 10228–10233) and overexpression of GSK-3β in CHO cells, expressing both insulin receptor and insulin receptor substrate 1 (IRS-1) resulted in impairment of insulin action (Eldar-Finkelman and Krebs, *PNAS*, 1997, 94, 9660–9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662–1666).

Dermatological Disorders

The finding that transient β-catenin stabilization may play a role in hair development (Gat, et al., *Cell*, 1998, 95, 605–614) suggests that GSK-3 inhibitors could also be used in the treatment of baldness.

Inflammatory Diseases

Studies on fibroblasts from the GSK-3β knockout mouse indicate that inhibition of GSK-3 may be useful in treating inflammatory disorders or diseases through the negative regulation of NFkB activity (Hoeflich K. P., et al., *Nature*, 2000, 406, 86–90).

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.*, 1998, 273, 19929–19932). Lithium, a low mM inhibitor of GSK-3, has been shown to protect cerebellar granule neurons from death (D'Mello, et al., *Exp. Cell Res.*, 1994, 211, 332–338) and chronic lithium treatment has demonstrable efficacy in the middle cerebral artery occlusion model of stroke in rodents (Nonaka and Chuang, *Neuroreport*, 1998, 9(9), 2081–2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.*, 1997, 272(40), 25326–32). β-catenin is phosphorylated by GSK-3 as part of a tripartite axin protein complex resulting in β-catenin degradation (Ikeda, et al., *EMBO J.*, 1998, 17, 1371–1384). Inhibition of GSK-3 activity is involved in the stabilization of catenin hence promotes β-catenin-LEF-1/TCF transcriptional activity (Eastman, Grosschedl, *Curr. Opin. Cell Biol.*, 1999, 11, 233). Studies have also suggested that GSK-3 inhibitors may also be of value in treatment of schizophrenia (Cotter D., et al. *Neuroreport*, 1998, 9, 1379–1383; Lijam N., et al., *Cell*, 1997, 90, 895–905) and manic depression (Manji, et al., *J. Clin. Psychiatry*, 1999, 60, (Suppl 2) 27–39 for review).

Accordingly, compounds found useful as GSK-3 inhibitors could have further therapeutic utility in the treatment of diabetes, dermatological disorders, inflammatory diseases and central nervous system disorders.

Aspects of the present invention include a method for treating or ameliorating a kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Aspects of the present invention include the use of a compound of Formula (I) for the preparation of a medicament for treating or ameliorating a kinase or dual-kinase mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Aspects of the method of the present invention include a compound or pharmaceutical composition thereof advantageously co-administered in combination with other agents for treating or ameliorating a kinase or dual-kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones) or biguanides or a glucosidase inhibitors.

The combination product comprises co-administration of a compound of Formula (I) or pharmaceutical composition thereof and an additional agent for treating or ameliorating a kinase or dual-kinase mediated disorder, the sequential administration of a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the PKC and GSK isoforms and their important roles in physiology provide incentive to produce highly selective PKC and GSK inhibitors. Given the evidence demonstrating linkage of certain isoforms to disease states, it is reasonable to assume that inhibitory compounds that are selective to one or two PKC isoforms or to a GSK isoform relative to the other PKC and GSK isoforms and other protein kinases are superior therapeutic agents. Such compounds should demonstrate greater efficacy and lower toxicity by virtue of their specificity. Accordingly, it will be appreciated by one skilled in the art that a compound of Formula (I) is therapeutically effective for certain kinase or dual-kinase mediated disorders based on the modulation of the disorder by selective kinase or dual-kinase inhibition. The usefulness of a compound of Formula (I) as a selective kinase or dual-kinase inhibitor can be determined according to the methods disclosed herein and the scope of such use includes use in one or more kinase or dual-kinase mediated disorders.

Therefore, the term "kinase or dual-kinase mediated disorders" as used herein, includes, and is not limited to, cardiovascular diseases, diabetes, diabetes-associated disorders, inflammatory diseases, immunological disorders, dermatological disorders, oncological disorders and CNS disorders.

Cardiovascular diseases include, and are not limited to, acute stroke, heart failure, cardiovascular ischemia, thrombosis, atherosclerosis, hypertension, restenosis, retinopathy of prematurity or age-related macular degeneration. Diabetes includes insulin dependent diabetes or Type II non-insulin dependent diabetes mellitus. Diabetes-associated disorders include, and are not limited to, impaired glucose tolerance, diabetic retinopathy, proliferative retinopathy, retinal vein occlusion, macular edema, cardiomyopathy, nephropathy or neuropathy. Inflammatory diseases include, and are not limited to, vascular permeability, inflammation, asthma, rheumatoid arthritis or osteoarthritis. Immunological disorders include, and are not limited to, transplant tissue rejection, HIV-1 or immunological disorders treated or ameliorated by PKC modulation. Dermatological disorders include, and are not limited to, psoriasis, hair loss or baldness. Oncological disorders include, and are not limited to, cancer or tumor growth (such as breast, brain, kidney, bladder, ovarian or colon cancer or leukemia), proliferative angiopathy and angiogenesis; and, includes use for compounds of Formula (I) as an adjunct to chemotherapy and radiation therapy. CNS disorders include, and are not limited to, chronic pain, neuropathic pain, epilepsy, chronic neurodegenerative conditions (such as dementia or Alzheimer's disease), mood disorders (such as schizophrenia), manic depression or neurotraumatic, cognitive decline and ischemia-related diseases {as a result of head trauma (from acute ischemic stroke, injury or surgery) or transient ischemic stroke (from coronary bypass surgery or other transient ischemic conditions)}.

A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets*, Second Edition, Revised and Expanded, Volumes 1–3, edited by Lieberman, et al.; *Pharmaceutical Dosage Forms: Parenteral Medications*, Volumes 1–2, edited by Avis, et al.; and *Pharmaceutical Dosage Forms: Disperse Systems*, Volumes 1–2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.001 mg to about 300 mg (preferably, from about 0.01 mg to about 100 mg; and, more preferably, from about 0.1 mg to about 30 mg) and may be given at a dosage of from about 0.001 mg/kg/day to about 300 mg/kg/day (preferably, from about 0.01 mg/kg/day to about 100 mg/kg/day; and, more preferably, from about 0.1 mg/kg/day to about 30 mg/kg/day). Preferably, in the method for treating or ameliorating a kinase or dual-kinase mediated disorder described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose (i.e. TYLOSE™ available from Hoechst Celanese), polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W.R. Grace/Davison and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetyl-stearyl alcohol and the like), esters of fatty acids metallic soaps and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth and xanthan gum, cellulosics such as sodium carboxymethylcellulose, methylcellulose, hydroxymethylcellulose, hydroxyethylcellulose, hydroxypropyl cellulose and hydroxypropyl methylcellulose and combinations thereof, synthetic polymers such as polyvinyl pyrrolidone, carbomer (i.e. carboxypolymethylene) and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treating or ameliorating a kinase or dual-kinase mediated disorder is required for a subject in need thereof; in particular, whenever treating or ameliorating a kinase disorder mediated by selective inhibition of a kinase selected from protein kinase C or glycogen synthase kinase-3 is required; and, whenever treating or ameliorating a kinase disorder mediated by dual inhibition of at least two kinases selected from protein kinase C and glycogen synthase kinase-3 is required; and, more particularly, whenever treating or ameliorating a kinase disorder mediated by selective inhibition of a kinase selected from protein kinase C $\alpha$, protein kinase C $\beta$-II, protein kinase C $\gamma$ or glycogen synthase kinase-3$\beta$ is required; and, whenever treating or ameliorating a kinase disorder mediated by dual inhibition of at least two kinases selected from protein kinase C $\alpha$, protein kinase C β-II, protein kinase C γ or glycogen synthase kinase-3β is required.

The daily dose of a pharmaceutical composition of the present invention may be varied over a wide range from about 0.7 mg to about 21,000 mg per 70 kilogram (kg) adult human per day; preferably in the range of from about 7 mg to about 7,000 mg per adult human per day; and, more preferably, in the range of from about 7 mg to about 2,100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.001 mg/kg to about 300 mg/kg of body weight per day. Preferably, the range is from about 0.1 mg/kg to about 100 mg/kg of body weight per day; and, most preferably, from about 0.1 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art and will vary with the particular compound used, the mode of administration, the strength of the preparation and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:
ATP=adenosinetriphosphate
BSA=bovine serum albumin
DCM=dichloromethane
DMF=N,N-dimethylformamide
DMSO=dimethylsulfoxide
EGTA=ethylenebis(oxyethylenenitrilo)tetraacetic acid
h=hour
HEPES=4-(2-hydroxyethyl)-1-piperazine-ethanesulfonic acid
min=minute
rt=room temperature
TCA=trichloroacetic acid
THF=tetrahydrofuran
TFA=trifluoroacetic acid
TMSCHN$_2$=trimethylsilyldiazomethane General Synthetic Methods Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

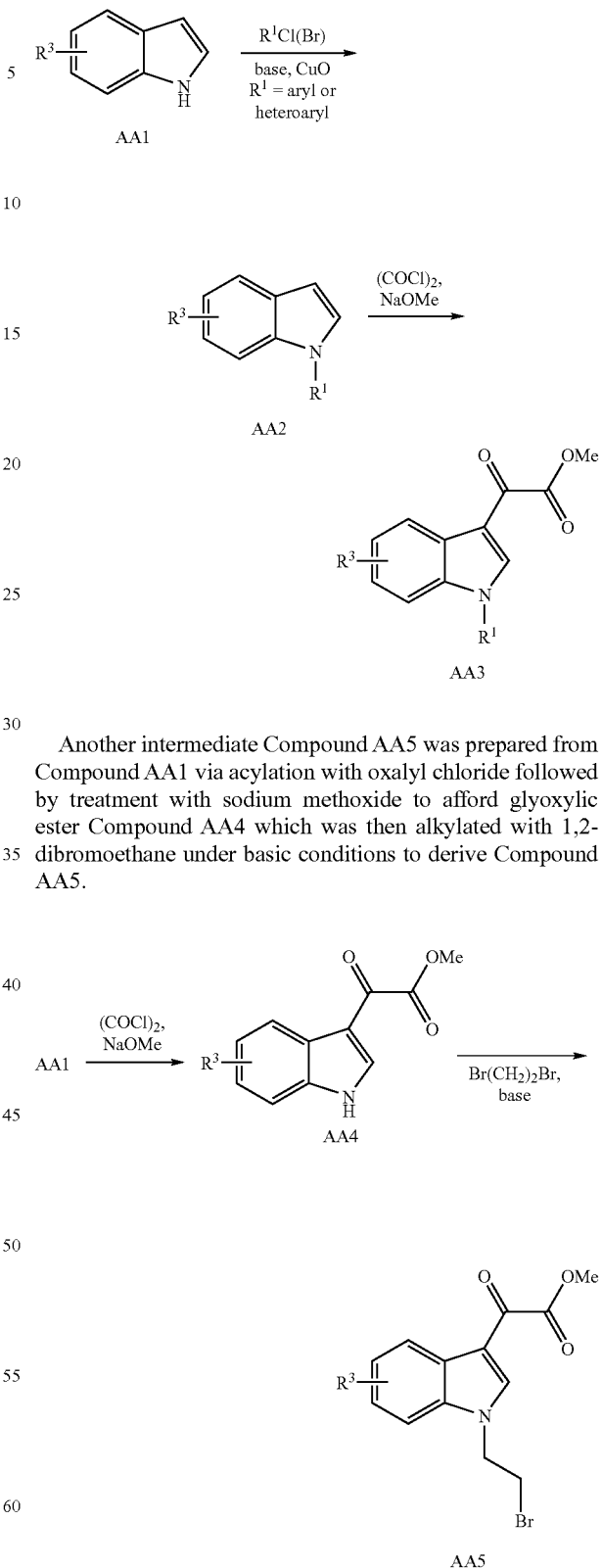

Another intermediate Compound AA5 was prepared from Compound AA1 via acylation with oxalyl chloride followed by treatment with sodium methoxide to afford glyoxylic ester Compound AA4 which was then alkylated with 1,2-dibromoethane under basic conditions to derive Compound AA5.

The intermediate Compound AA6 was prepared from Compound AA4 via alkylation with an appropriate alkylating agent under basic conditions.

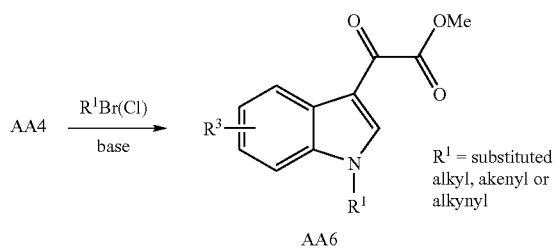

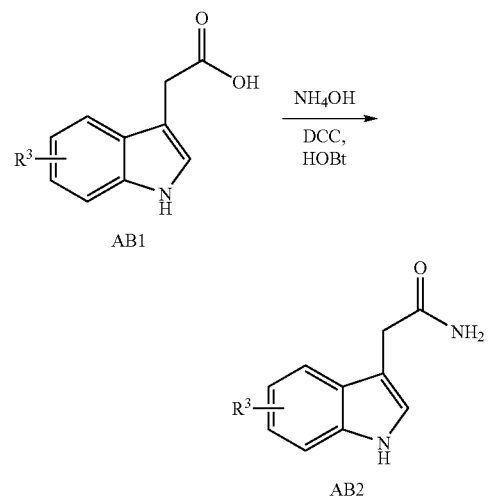

Target Compound AA8, may be prepared using Compound AA3, Compound AA5 or Compound AA6 in reaction with the amide Compound AA7.

The ester Compound AA3 (wherein $R^1$ is an aryl or heteroaryl) may be reacted with the amide Compound AA7 stirred in an aprotic solvent such as THF with ice bath cooling and a base, such as potassium tert-butoxide or sodium hydride, to give a target Compound AA8.

Alternatively, the ester Compound AA5 may be condensed with Compound AA7 under strong basic conditions, concomitantly causing the elimination of HBr, to give a target Compound AA8 (wherein $R^1$ is vinyl) as the product.

Further, the ester Compound AA6 may be reacted with Compound AA7 under basic conditions to give a substituted indole pyrroline Compound AA8 as the product.

The Compound AB2 was alkylated with a protected bromo-$R^1$ Compound AB3 in the presence of a base such as $Cs_2CO_3$ in DMF to give an $R^1$ substituted amide Compound AB4.

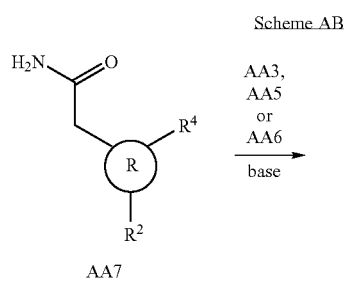

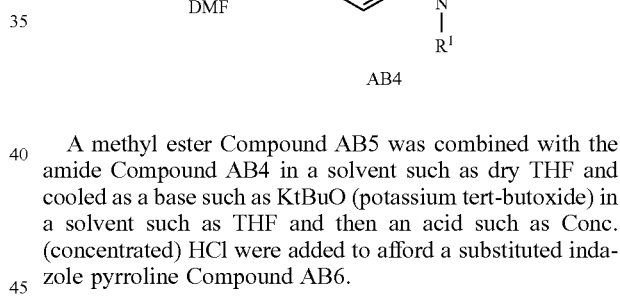

A methyl ester Compound AB5 was combined with the amide Compound AB4 in a solvent such as dry THF and cooled as a base such as KtBuO (potassium tert-butoxide) in a solvent such as THF and then an acid such as Conc. (concentrated) HCl were added to afford a substituted indazole pyrroline Compound AB6.

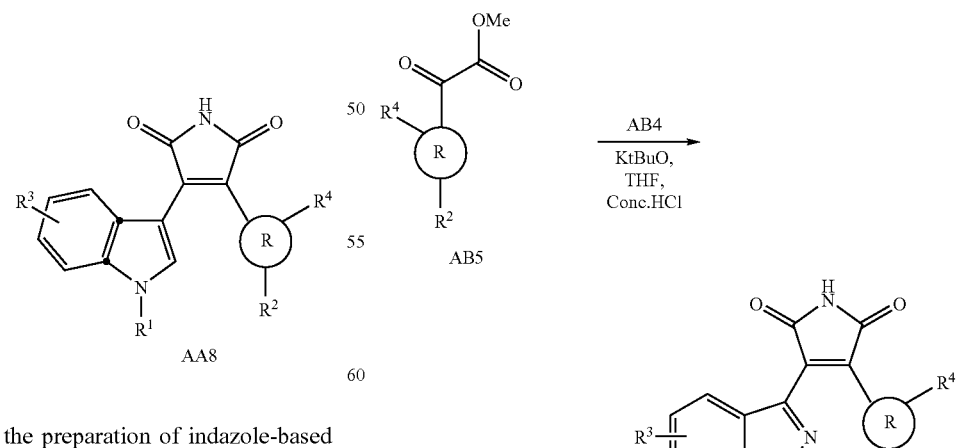

Scheme AB describes the preparation of indazole-based analogues, wherein the indazole acid Compound AB1 was converted to the amide Compound AB2 via coupling reaction with ammonium hydroxide in the presence of coupling reagents such as DCC/HOBt.

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a BrukerAC 300B (300 MHz proton) or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-µm silica gel plates. Preparative TLC was performed with Analtech 1000-µm silica gel GF plates. Flash column chromatography was conducted with flash column silica gel (40–63 µm) and column chromatography was conducted with standard silica gel. HPLC separations were carried out on three Waters PrepPak® Cartridges (25×100 mm, Bondapak® C18, 15–20 µm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

Representative Chemical Abstracts Service (CAS) Index-like names for the compounds of the present invention were derived using the ACD/LABS SOFTWARE™ Index Name Pro Version 4.5 nomenclature software program provided by Advanced Chemistry Development, Inc., Toronto, Ontario, Canada.

EXAMPLE 1

3-[2-[3-(dimethylamino)-2-hydroxypropoxy]phenyl]-4-(1-ethenyl-1H-indol-3-yl)-1H-pyrrole-2,5-dione (Compound 4)

A suspension of Compound 1a (10.0 g, 0.053 mole) in dichloromethane:methanol (6:1 ratio; 350 mL) was stirred and cooled in an ice bath while a solution of TMSCHN$_2$ (79 mL, 2.0 M) in hexane was added dropwise over a 1 hr period. The mixture was allowed to warm to rt and was stirred overnight. The resulting light yellow solid was filtered and washed with ether to yield Compound 1b (7.5 g, 70%). $^1$H NMR (DMSO-d$_6$) δ 12.5 (s, 1H), 8.45 (d, 1H), 8.2 (d, 1H), 7.55 (d, 1H), 7.3 (m, 2H), 3.95 (s, 3H).

Compound 1b (4.0 g, 0.0197 mole) and 1,2-dibromoethane (18.5 g, 0.0985 mole) were combined in anhydrous DMF (80 mL) and treated with cesium carbonate (12.8 g, 0.0394 mole). The mixture was stirred under an argon atmosphere at rt for 1 h, then the temperature was raised to 50° C. for 4 h. The mixture was stirred at rt overnight. The resulting white solids were removed by filtration, then partitioned between 600 mL of ether and 300 mL of water. The organic layer was washed with water (3×) and brine, then dried over anhydrous sodium sulfate. The solvent was removed in vacuo and the resulting oily residue triturated with hexane to give a crude solid product. The crude solid was recrystallized from ethyl acetate/hexane and flash chromatographed on silica eluted with ethyl acetate/hexane to give Compound 1c (5.5 g, 47%).

Isopropanol (7 mL), Compound 1d (0.800 g, 5.3 mm) and epichlorohydrin (4.12 mL, 52.7 mm) were added to a solution of sodium hydroxide (0.212 g, 5.3 mm) in water (1.4 mL). The reaction mixture was stirred at 70° C. for 2 hrs. The hot solution was filtered and the filtrate was evaporated in vacuo to give Compound 1e (1.35 g) as a semi-solid. ES-MS m/z 208 (MH$^+$). Compound 1e (0.400 g, 1.9 mm) and methanol (13 mL) were added to a solution of 2.0 M dimethylamine in methanol (9.5 mL, 19 mm). The mixture was stirred at 50° C. for 1.5 hrs, then cooled and filtered and the filtrate was evaporated in vacuo to give solid Compound 1f (0.450 g). ES-MS m/z 253 (MH$^+$). Compound 1f (0.200 g, 0.80 mm) and Compound 1c (0.3101 g, 1.0 mm) were dissolved in THF/DMF (34 mL/6 mL) followed by the addition of 60% NaH (0.0320 g, 0.80 mm). The mixture was stirred overnight, then at ambient temperature for 24 hrs. Additional 60% NaH (0.032 g. 0.80 mm) was added followed by stirring at ambient temperature for 1 hr and then at 50° C. for 1 hr. The mixture was cooled and stirred for 24 hrs at ambient temperature, then quenched with water and extracted with ethyl acetate. The organic layer was washed with water (1×45 mL) and brine (1×90 mL), then dried (Na$_2$SO$_4$) and evaporated in vacuo to give the crude product as a solid. The product was purified by column chromatography (silica gel, 93% DCM/5% MeOH/2% NH$_4$OH to 91% DCM/7% MeOH/2% NH$_4$OH) to afford Compound 4 (0.0082 g, 2%). $^1$HNMR (CD$_3$OD) δ 2.33 (s, 6H, CH$_3$) 2.56 (m, 2H), 3.36–3.54 (m, 2H, CH$_2$), 3.86–4.00 (m, 1H), 4.96 (d, 1H), 5.44 (d, 1H), 6.47 (d, 1H), 6.72 (t, 1H), 6.91–7.57 (m, 7H), 8.28 (s, 1H). ES-MS m/z 432 (MH$^+$).

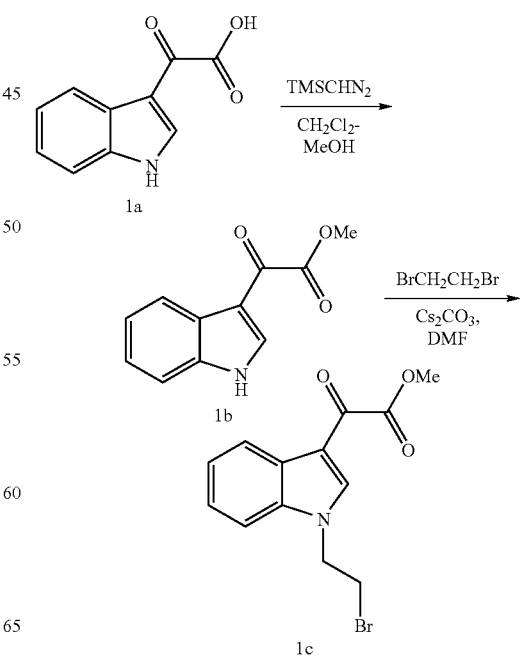

37
-continued

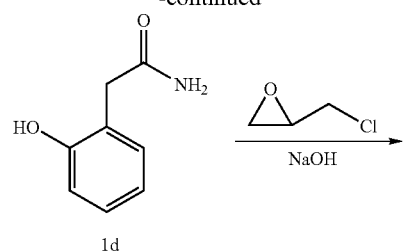

1d

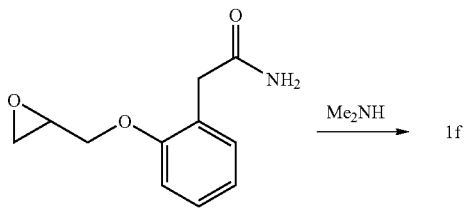

1e

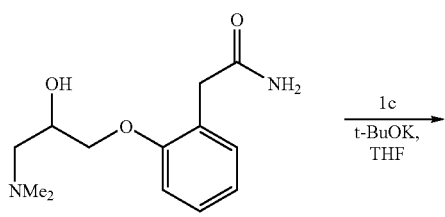

1f

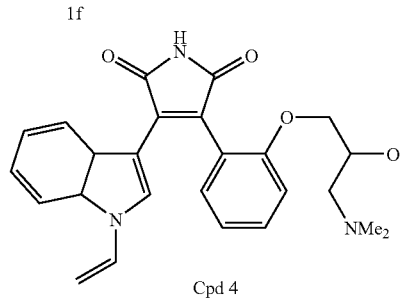

Cpd 4

Using the procedure of Example 1 and the appropriate reagents and starting materials known to those skilled in the art, other compounds of the present invention may be prepared including, but not limited to:

| Cpd | Name | MS m/z (MH+) |
|---|---|---|
| 1 | 3-(1-ethenyl-1H-indol-3-yl)-4-[4-[2-hydroxy-3-(1-piperidinyl)propoxy]phenyl]-1H-pyrrole-2,5-dione | 472 |
| 2 | 3-[3-[3-(dimethylamino)-2-hydroxypropoxy]phenyl]-4-(1-ethenyl-1H-indol-3-yl)-1H-pyrrole-2,5-dione | 432 |
| 3 | 3-[4-[3-(dimethylamino)-2-hydroxypropoxyphenyl]-4-(1-ethenyl-1H-indol-3-yl)-1H-pyrrole-2,5-dione | 432 |
| 5 | 3-(1-ethenyl-1H-indol-3-yl)-4-(2-hydroxy-1-naphthalenyl)-1H-pyrrole-2,5-dione | 381 |
| 6 | 3-[2-[3-(dimethylamino)-2-hydroxypropoxy]-1-naphthalenyl]-4-(1-ethenyl-1H-indol-3-yl)-1H-pyrrole-2,5-dione | 482 |
| 15 | 3-[3-[3-(dimethylamino)-2-hydroxypropoxy]-1-naphthalenyl]-4-(1H-indol-3-yl)-1H-pyrrole-2,5-dione | 456 |
| 19 | 3-[4-[3-(dimethylamino)-2-hydroxypropoxy]phenyl]-4-[1-[3-(dimethylamino)propyl]-1H-indol-3-yl]-1H-pyrrole-2,5-dione | 491 |
| 20 | 3-[2-[3-(dimethylamino)-2-hydroxypropoxy]phenyl]-4-[1-[3-(dimethylamino)propyl]-1H-indol-3-yl]-1H-pyrrole-2,5-dione | 491 |

38
-continued

| Cpd | Name | MS m/z (MH+) |
|---|---|---|
| 21 | 3-[2-[3-(dimethylamino)-2-hydroxypropoxy]phenyl]-4-[1-(2-hydroxyethyl)-1H-indol-3-yl]-1H-pyrrole-2,5-dione | 450 |

EXAMPLE 2

3-[1-[2-(2-butynylmethylamino)ethyl]-1H-indol-3-yl]-4-(1-naphthalenyl)-1H-pyrrole-2,5-dione (Compound 17)

3-[1-[2-(3-butynylmethylamino)ethyl]-1H-indol-3-yl]-4-(1-naphthalenyl)-1H-pyrrole-2,5-dione (Compound 18)

3-Butynyl p-tosylate Compound 2a (0.90 g, 4.0 mmol) and 2-methylaminoethanol (0.30 g, 4.0 mmol) were dissolved in DMF (2 mL) and sodium bicarbonate (0.34 g, 4.0 mmol) was added. The mixture was heated to 75° C. under argon for 2 h then cooled to rt and partitioned between DCM (30 mL) and saturated sodium bicarbonate (15 mL). The organic layer was washed once with sodium bicarbonate (15 mL), once with brine (10 mL), then dried ($Na_2SO_4$) and evaporated in vacuo to give Compound 2b as a colorless oil (0.98 g). Compound 2b was added to Compound 1b (0.43 g, 2.1 mmol) followed by triphenyl phosphine (0.73 g, 2.8 mmol) in THF (15 mL) and diethylazodicarboxylate (0.49 g, 2.8 mmol) and the mixture was stirred at ambient temperature for 1 h. The product was evaporated in vacuo to an oil, which was purified via flash column chromatography (ethyl acetate) to give Compound 2c (0.37 g, 56%) as a tan solid. ES-MS m/z 313 (MH+). A portion of the indole Compound 2c (34 mg, 0.11 mmol) and 1-naphthalene acetamide (Compound 2d, 18 mg, 0.11 mmol) in THF (1 mL) were treated with 1M potassium t-butoxide in THF (0.33 mL, 0.33 mmol) while being cooled in an ice bath. The mixture was stirred at ambient temperature for 3 h, then treated with 12 N HCl (0.15 mL), stirred for 10 min and evaporated in vacuo to give an oil. The oil was partitioned between chloroform and saturated sodium bicarbonate. The organic layer was washed again with saturated sodium bicarbonate, once with brine, then dried ($Na_2SO_4$) and evaporated in vacuo to give a mixture of Compound 17 and Compound 18 (50 mg) as an orange oil. The material was purified by preparative TLC to separate Compound 17 and Compound 18. Compound 17: $^1$H NMR ($CDCl_3$) δ 1.81 (s, 3H), 2.31 (s, 3H), 2.81 (m, 2H), 3.30 (bd s, 2H), 4.22 (m, 2H), 6.18 (d, J=8.0 Hz, 1H), 6.52 (m, 1H), 7.0 (m, 1H), 7.15–8.0 (m, 8H), 8.07 (s, 1H); ES-MS m/z 448 (MH+). Compound 18: $^1$H NMR ($CDCl_3$) δ 1.97 (m, 1H), 2.24 (m, 2H), 2.29 (s, 3H), 2.61 (t, J=7.3 Hz, 2H), 2.77 (m, 2H), 4.19 (m, 2H), 6.18 (d, J=8.2 Hz, 1H), 6.51 (m, 1H), 7.0 (m, 1H), 7.20–7.93 (m, 8H), 8.04 (s, 1H),; ES-MS m/z 448 (MH+).

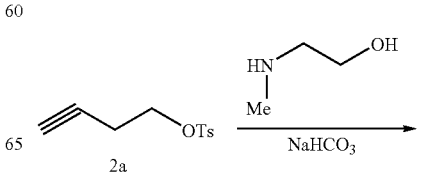

2a

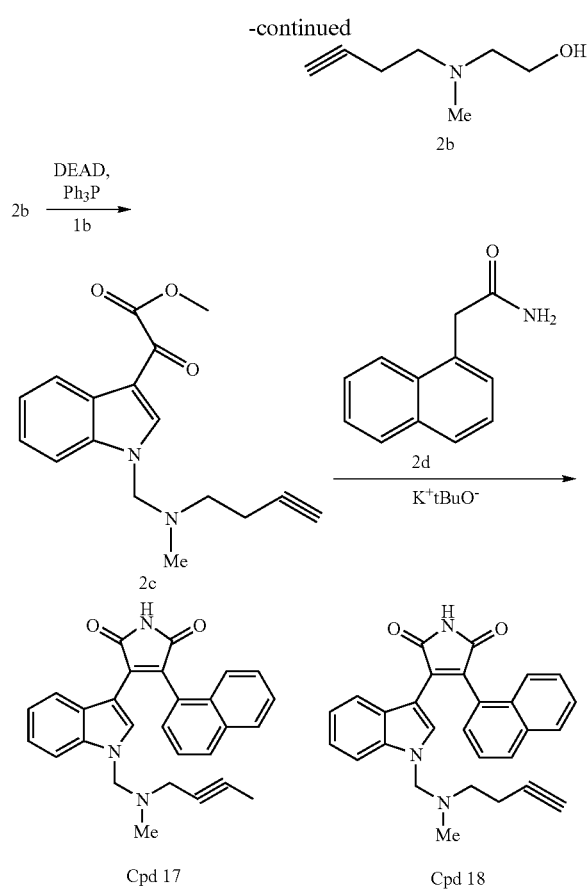

Using the procedure of Example 2 and the appropriate reagents and starting materials known to those skilled in the art, other compounds of the present invention may be prepared including, but not limited to:

| Cpd | Name | MS m/z (MH+) |
|---|---|---|
| 22 | 3-(3-bromophenyl)-4-[1-[3-(3-butynylmethylamino) propyl]-1H-indol-3-yl]-1H-pyrrole-2,5-dione | 476 |
| 23 | 3-[1-[3-(3-butynylmethylamino)propyl]-1H-indol-3-yl]- 4-(3-iodophenyl)-1H-pyrrole-2,5-dione | 524 |
| 55 | 3-(2-Methoxyphenyl)-4-[1-(tetrahydropyran-4-yl)-1H- indol-3-yl]-1H-pyrrole-2,5-dione | 403 |

EXAMPLE 3

3-[1-[2-(2-butynylmethylamino)ethyl]-1H-indol-3-yl]-4-(5-chlorobenzo[b]thien-3-yl)-1H-pyrrole-2,5-dione (Compound 34)

3-[1-[2-(3-butynylmethylamino)ethyl]-1H-indol-3-yl]-4-(5-chlorobenzo[b]thien-3-yl)-1H-pyrrole-2,5-dione (Compound 35)

Using the procedure described in Example 2, indole Compound 2c (68 mg, 0.22 mmol) was combined with 5-Chloro-benzothiazol-3-yl acetamide (Compound 4b, 45 mg, 0.20 mmol) in THF (2 mL) and treated with 1.0 M potassium t-butoxide in THF (0.66 mL, 0.66 mmol). Upon work-up, an orange solid was recovered (130 mg) and purified by preparative TLC to give Compound 34: $^1$H NMR (CDCl$_3$) δ 1.84 (s, 3H), 2.37 (s, 3H), 2.88 (dd, J=7.0/7.1 Hz, 2H), 3.34 (bd s, 2H), 4.28 (dd, J=7.1/7.1 Hz, 2H), 6.43 (d, J=8.1 Hz, 1H), 6.64 (m, 1H), 7.06 (m, 1H), 7.0–7.73 (m, 4H), 7.82 (s, 1H), 8.03 (s, 1H); ES-MS m/z 488 (MH+), and Compound 35: $^1$H NMR (CDCl$_3$) δ 1.99 (m, 1H), 2.33 (m, 2H), 2.35 (s, 3H), 2.67 (dd, J=7.2/7.2 Hz, 2H), 2.84 (m, 2H), 4.27 (dd, J=6.7/6.7 Hz, 2H), 6.43 (d, J=8.0 Hz, 1H), 6.64 (m, 1H), 7.0–7.50 (m, 4H), 7.72 (d, J=8.6 Hz, 1H), 7.81 (s, 1H), 8.07 (s, 1H); ES-MS m/z 488 (MH+).

EXAMPLE 4

3-(5-chlorobenzo[b]thien-3-yl)-4-[1-[3-(dimethylamino)propyl]-1H-indol-3-yl]-1H-pyrrole-2,5-dione (Compound 31)

HOBT (2.94 g, 21.8 mm) and DCC (4.29 g, 20.8 mm) were added to a solution of Compound 4a (4.50 g, 19.8 mm) in DCM (80 mL) and DMF (20 mL). The mixture was stirred at ambient temperature for 30 min, then 28% NH$_3$ (2.00 mL, 29.7 mm) was added and the reaction was stirred at ambient temperature for 24 hrs. The mixture was filtered and the filtered solid was washed with DCM (2×). The filtrate was diluted with ethyl acetate (225 mL) and washed with saturated sodium bicarbonate (2×45 mL), then dried (NaSO$_4$) to afford a white solid Compound 4b (1.13 g). $^1$HNMR (DMSO) 63.65 (s, CH$_2$), 7.02 (s, NH$_2$), 7.62 (s, H-2 and H-7), 7.90–7.91 (m, H-6), 8.00 (d, H-4). ES-MS m/z 432 (MH+).

Compound 1b (2.50 g, 12.3 mm) was dissolved in dry DMF (50 mL) followed by the addition of 3-dimethylaminopropyl chloride hydrochloride (2.34 g, 14.8 mm) and cesium carbonate (10.00 g, 30.7 mm). The mixture was stirred at 60° C. for 24 hrs. Additional 3-dimethylaminopropyl chloride hydrochloride (0.5848 g, 3.7 mm) was added and the reaction was stirred at 60° C. C for 4 hrs. The mixture was filtered and the filtrate was diluted with ethyl acetate, washed with water (4×) and brine (1×), then dried (Na$_2$SO$_4$) and evaporated in vacuo. The crude product was chromatographed (silica gel 97% DCM/3% MeOH to 95% DCM/5% MeOH) to afford Compound 4c (1.35 g). $^1$HNMR (DMSO) δ 1.88–2.00 (m, 2H, CH$_2$), 2.12 (s, 8H, CH$_2$ and CH$_3$), 3.89 (s, 2H, CH$_3$), 4.34 (t, 2H), CH$_2$), 7.29–7.38 (m, 2H, H-5 and H-6), 7.67 (d, 1H, H-7), 8.17 (d, 1H, H-4) and 8.49 (s, 1H, H-2). ES-MS m/z 289 (MH+). Compound 4b (0.060 g, 0.26 mm) and Compound 4c (0.1124 g, 0.39 mm) were dissolved in dry THF (1 mL) followed by the addition of 60% NaH (0.104 g, 2.6 mm). The mixture was stirred at ambient temperature for 3 hrs and then the reaction was quenched with water and extracted with ethyl acetate. The organic layer was washed with water (1×15 mL) and brine (1×15 mL), then dried (Na$_2$SO$_4$), and evaporated in vacuo. The crude product was chromatographed (silica gel-97% DCM/1% MeOH/2% NH$_4$OH) to afford Compound 31 (0.0275 g, 23%). $^1$HNMR (CD$_3$OD) δ 0.3793–0.4566 (m, 2H, CH$_2$), 0.6618 (s, 6H, CH$_3$), 0.759 (t, 2H, CH$_2$), 2.71 (t, 2H, CH$_2$), 4.85–4.99 (m, 2H, aromatics), 5.42–5.61 (m, 3H, aromatics), 5.80 (d, 2H, aromatics), 6.19 (d, 1H, aromatics), 6.38 (d, 2H, aromatics). ES-MS m/z 464 (MH+).

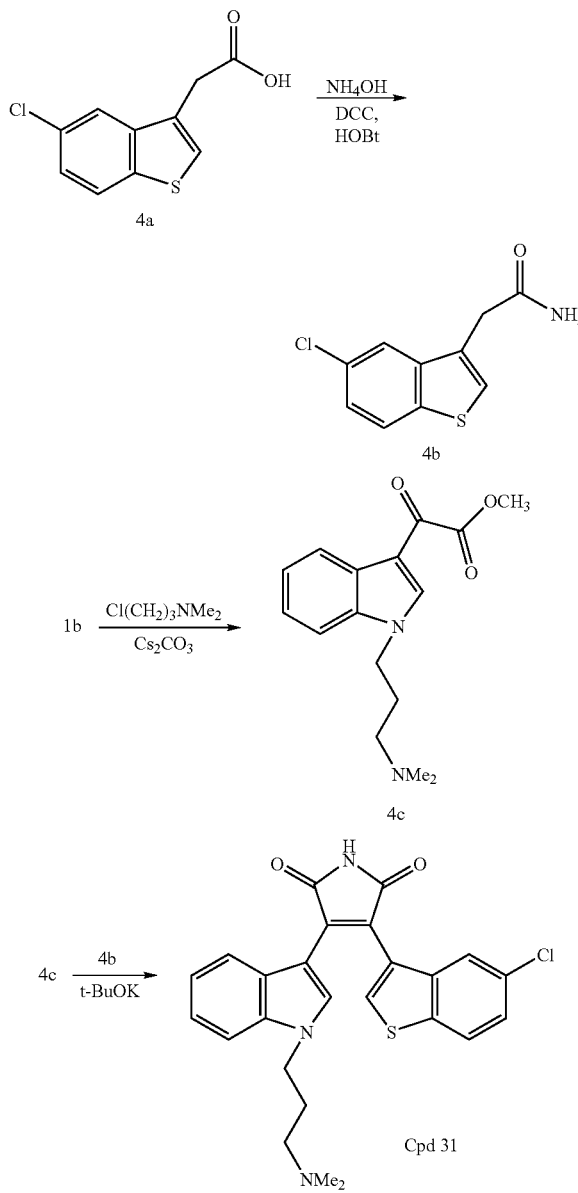

| Cpd | Name | MS m/z (MH+) |
|---|---|---|
| 14 | 3-(3-bromophenyl)-4-[1-[3-(methylamino)propyl]-1H-indol-3-yl]-1H-pyrrole-2,5-dione | 438 |
| 16 | 3-[1-[2-(diethylamino)ethyl]-1H-indol-3-yl]-4-(1-naphthalenyl)-1H-pyrrole-2,5-dione | 438 |
| 32 | 3-benzo[b]thien-3-yl-4-[1-(3-hydroxypropyl)-1H-indol-3-yl]-1H-pyrrole-2,5-dione | 430 |
| 36 | 3-(5-chlorobenzo[b]thien-3-yl)-4-[1-(2,2-diethoxyethyl)-1H-indol-3-yl]-1H-pyrrole-2,5-dione | 495 |
| 37 | 3-[4-(5-chlorobenzo[b]thien-3-yl)-2,5-dihydro-2,5-dioxo-1H-pyrrol-3-yl]-1H-indole-1-acetaldehyde | 421 |
| 38 | 3-(5-chlorobenzo[b]thien-3-yl)-4-[1-[2-(dimethylamino)ethyl]-1H-indol-3-yl]-1H-pyrrole-2,5-dione | 450 |
| 44 | 3-(5-chlorobenzo[b]thien-3-yl)-4-[1-[2-(diethylamino)ethyl]-1H-indol-3-yl]-1H-pyrrole-2,5-dione | 478 |
| 48 | 3-(5-chlorobenzo[b]thien-3-yl)-4-[1-(3-hydroxypropyl)-1H-indol-3-yl]-1H-pyrrole-2,5-dione | 437 |
| 49 | 3-(5-chlorobenzo[b]thien-3-yl)-4-[1-[3-(dimethylamino)propyl]-1H-indol-3-yl]-1H-pyrrole-2,5-dione | 498 |

EXAMPLE 5

3-(5-chlorobenzo[b]thien-3-yl)-4-[1-[2-(methyl-2-propynylamino)ethyl]-1H-indol-3-yl]-1H-pyrrole-2,5-dione (Compound 33)

Compound 1b (1.50 g, 7.4 mm) and 1,3-dibromopropane (3.75 mL, 37.0 mm) were dissolved in dry DMF (30 mL) followed by the addition of cesium carbonate (4.89 g, 15.0 mm). The mixture was stirred at 47° C. for 24 hrs, then cooled to rt and filtered. The filtrate was diluted with ethyl acetate, washed with water (4x) and brine (1x), then dried (Na$_2$SO$_4$) and evaporated in vacuo. The crude product was chromatographed (silica gel-10% EtoAc/90% Hex to 20% EtoAC/80% Hex) to afford Compound 5a (0.890 g). $^1$HNMR (CDCl$_3$) δ 2.39–2.47 (m, 2H, CH$_2$), 3.33 (t, 2H, CH$_2$), 3.96 (s, 3H, CH$_3$), 4.44 (t, 2H, CH$_2$), 7.35–7.46 (m, 3H, aromatics), 8.45–8.47 (m, 2H, aromatics). ES-MS m/z 324 (MH+).

Diisopropylethylamine (0.11 mL, 0.62 mm) and N-methyl propargylamine (0.026 mL, 0.31 mm) were added to a solution of Compound 5a (0.100 g, 0.310 mm) in THF (5 mL). The mixture was stirred at ambient temperature for 72 hrs. Additional N-methyl propargylamine (0.0043 g, 0.062 mm) was added and the mixture was stirred at 40° C. for 2 hrs, then cooled and evaporated in vacuo to give Compound 5b (0.1517 g). $^1$HNMR (CD$_3$OD) δ 2.02–2.07 (m, 2H, CH$_2$), 2.29 (s, 3H, CH$_3$), 2.42 (t, 2H, CH$_2$), 2.57–2.58 (m, 2H, CH), 3.17–3.29 (m, 2H, CH$_2$), 3.94 (s, 3H, CH$_3$), 4.39 (t, 2H, CH$_2$), 7.30–7.35 (m, 2H, H-5 and H-6), 7.57 (d, 1H, H-7), 8.26 (d, 1H, H-4), 8.47 (s, 1H, H-2). ES-MS m/z 313 (MH+).

Compound 4b (0.0937 g. 0.30 mm) and Compound 5b (0.040 g, 0.18 mm) in dry THF (3 mL) were cooled to 0° C. in an ice water bath. A solution of 60% NaH (0.044 g. 1.1 mm) in dry THF (2 mL) was added portionwise over 3 min. The mixture was stirred at 0° C. for 5 min and then was warmed to ambient temperature and stirred for 4 hrs. The reaction was quenched with water and extracted with ethyl acetate. The organic layer was washed with brine (8 mL), then dried (Na$_2$SO$_4$) and evaporated in vacuo to an orange solid. The crude product was chromatographed (silica gel-DCM to 95% DCM/3% MeOH) to afford Compound 33 (0.0115, 13%). $^1$HNMR (CD$_3$OD) δ 1.97–2.02 (m, 2H, CH$_2$), 2.32 (s, 3H, CH$_3$), 2.44 (t, 2H, CH$_2$), 2.62 (s, 1H, CH), Using the procedure of Example 4 and the appropriate reagents and starting materials known to those skilled in the art, other compounds of the present invention may be prepared including, but not limited to:

| Cpd | Name | MS m/z (MH+) |
|---|---|---|
| 7 | 3-[1-(2,2-diethoxyethyl)-1H-indol-3-yl]-4-(2-methoxyphenyl)-1H-pyrrole-2,5-dione | 435 |
| 8 | 3-[2,5-dihydro-4-(2-methoxyphenyl)-2,5-dioxo-1H-pyrrol-3-yl]-1H-indole-1-acetaldehyde | 361 |
| 9 | 3-[1-[2-[(2-hydroxyethyl)methylamino]ethyl]-1H-indol-3-yl]-4-(2-methoxyphenyl)-1H-pyrrole-2,5-dione | 420 |
| 12 | 3-[1-[3-(dimethylamino)propyl]-1H-indol-3-yl]-4-(1-naphthalenyl)-1H-pyrrole-2,5-dione | 424 |
| 13 | 3-(3-bromophenyl)-4-[1-(5-hexynyl)-1H-indol-3-yl]-1H-pyrrole-2,5-dione | 447 |

3.30–3.37 (m, 2H, CH$_2$), 4.31 (t, 2H, CH$_2$), 6.45–6.58 (m, 2H, aromatics, 6.98–7.39 (m, 4H, aromatics), 7.78–8.02 (m, 3H, aromatics). ES-MS m/z 488 (MH$^+$).

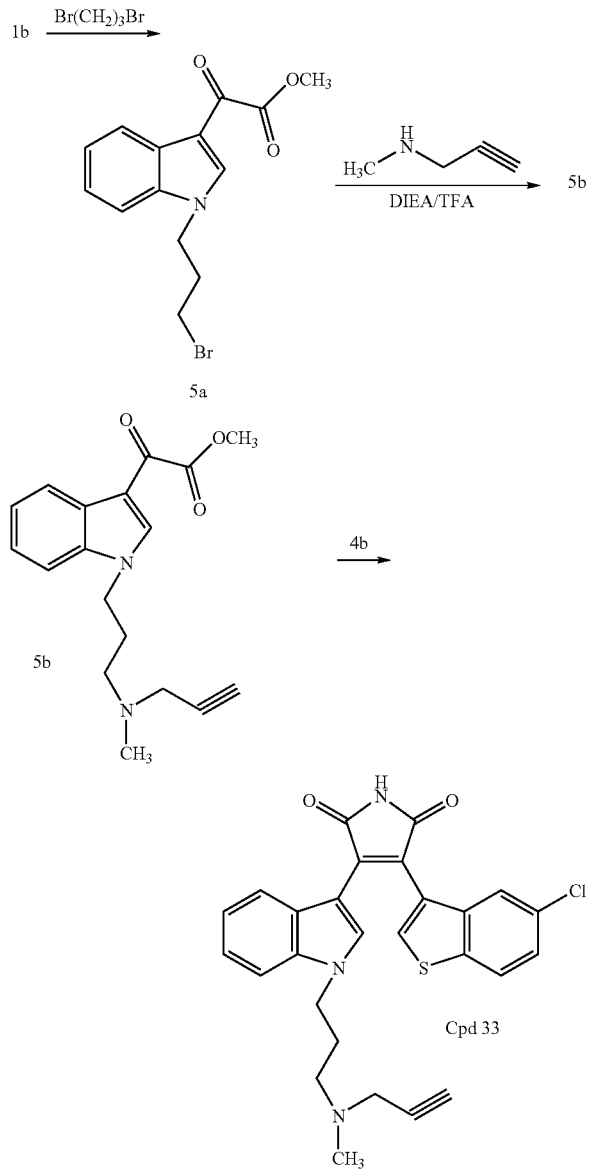

Using the procedure of Example 5 and the appropriate reagents and starting materials known to those skilled in the art, other compounds of the present invention may be prepared including, but not limited to:

| Cpd | Name | MS m/z (MH$^+$) |
|---|---|---|
| 11 | 3-(3-bromophenyl)-4-[1-[3-(methyl-2-propynylamino)propyl]-1H-indol-3-yl]-1H-pyrrole-2,5-dione | 476 |
| 39 | 3-(5-chlorobenzo[b]thien-3-yl)-4-[1-[2-[[2-(dimethylamino)ethyl]methylamino]ethyl]-1H-indol-3-yl]-1H-pyrrole-2,5-dione | 507 |
| 40 | 3-(5-chlorobenzo[b]thien-3-yl)-4-[1-[3-(4-methyl-1-piperazinyl)propyl]-1H-indol-3-yl]-1H-pyrrole-2,5-dione | 519 |
| 41 | 3-(5-chlorobenzo[b]thien-3-yl)-4-(1-[2-[(2-hydroxyethyl)methylamino]ethyl]-1H-indol-3-yl]-1H-pyrrole-2,5-dione | 480 |
| 42 | 3-(5-chlorobenzo[b]thien-3-yl)-4-[1-[2-(4-morpholinyl)ethyl]-1H-indol-3-yl]-1H-pyrrole-2,5-dione | 492 |
| 43 | 3-(5-chlorobenzo[b]thien-3-yl)-4-[1-[2-(1-pyrrolidinyl)ethyl]-1H-indol-3-yl]-1H-pyrrole-2,5-dione | 476 |
| 45 | 3-(5-chlorobenzo[b]thien-3-yl)-4-[1-[2-[(2-furanylmethyl)methylamino]ethyl]-1H-indol-3-yl]-1H-pyrrole-2,5-dione | 516 |
| 46 | 3-(5-chlorobenzo[b]thien-3-yl)-4-[1-[2-(3-thiazolidinyl)ethyl]-1H-indol-3-yl]-1H-pyrrole-2,5-dione | 494 |
| 47 | 3-(5-chlorobenzo[b]thien-3-yl)-4-[1-[3-(methyl-2-propenylamino)propyl]-1H-indol-3-yl]-1H-pyrrole-2,5-dione | 490 |
| 50 | 3-(2,5-dichlorobenzo[b]thien-3-yl)-4-[1-[3-(methyl-2-propenylamino)propyl]-1H-indol-3-yl]-1H-pyrrole-2,5-dione | 524 |

EXAMPLE 6

3-(2-methoxyphenyl)-4-[1-(5-pyrimidinyl)-1H-indol-3-yl]-1H-pyrrole-2,5-dione (Compound 26)

Bromopyrimidine Compound 6a (10.46 g, 65.7 mmol) and indole Compound 6b (7 g, 59.8 mmol) were dissolved in DMF (150 mL). Potassium carbonate (8.26 g, 59.8 mmol) and CuO (475 mg, 6 mmol) were added and the mixture was refluxed under argon for 18 h. The solvent was evaporated and partitioned between chloroform (500 mL) and water (200 mL). The organic layer was washed with water (3×50 mL) and brine (2×50 mL), then dried (Na$_2$SO$_4$) and evaporated in vacuo to a brown oil. The oil was filtered through a small layer of silica and washed several times with chloroform. The organic solvents were combined and evaporated to give a crude product Compound 6c (11.9 g, containing approximately 14% of starting material Compound 6b).

The crude Compound 6c (8.07 g, 0.041 mole) in methylene chloride (150 mL) was cooled in an ice bath and treated dropwise with oxalyl chloride (10.5 g, 0.083 mole) while stirring under argon. The mixture was warmed to rt and then heated to 30° C. for 20 h. The resulting yellow slurry was then cooled to −65° C. and MeOH (20 mL) was added dropwise. The cold mixture was allowed to warm to rt and was stirred at rt overnight. The product was filtered and washed with MeOH to yield Compound 6d (8.0 g, 69%) as a light yellow solid. $^1$H NMR (CDCl$_3$) δ 9.37 (s, 1H), 9.04 (s, 2H), 8.62 (s, 1H), 8.55 (m, 1H), 7.46 (m, 3H), 3.99 (s, 3H). ES-MS m/z 282 (MH$^+$).

The methyl ester Compound 6d (0.5 g, 1.78 mmol) and amide Compound 6e (0.2 g, 1.27 mmol) were combined in dry THF (8 mL) under argon and cooled in an ice bath as 1M potassium t-butoxide in THF (6 mL, 6 mmol) was added with stirring over a 10 min period. After 40 min, the reaction was quenched in an ice bath while 12 N HCl (2 mL, 24 mmol) was slowly added. The mixture was stirred for 15 min at rt, made slightly basic by the addition of 3N NaOH and extracted with EtOAc. The organic layers were combined and washed with saturated NaHCO$_3$ and brine, then dried (Na$_2$SO$_4$) and evaporated in vacuo to give a crude solid. The solid was then purified by flash column chromatography (97:3:0.3; DCM:MeOH:NH$_4$OH) to afford Compound 26 (102 mg, 20%) as a yellow flaky solid. $^1$H NMR (CDCl$_3$) δ 9.29 (s, 1H), 9.03 (s, 2H), 8.09 (s, 1H), 7.40 (m, 3H), 7.21

(m, 1H), 7.03 (t, J=7.5 Hz, 1H), 6.88 (m, 2H), 6.60 (d, J=8.1 Hz, 1H), 3.37 (s, 3H). ES-MS m/z 397 (MH+).

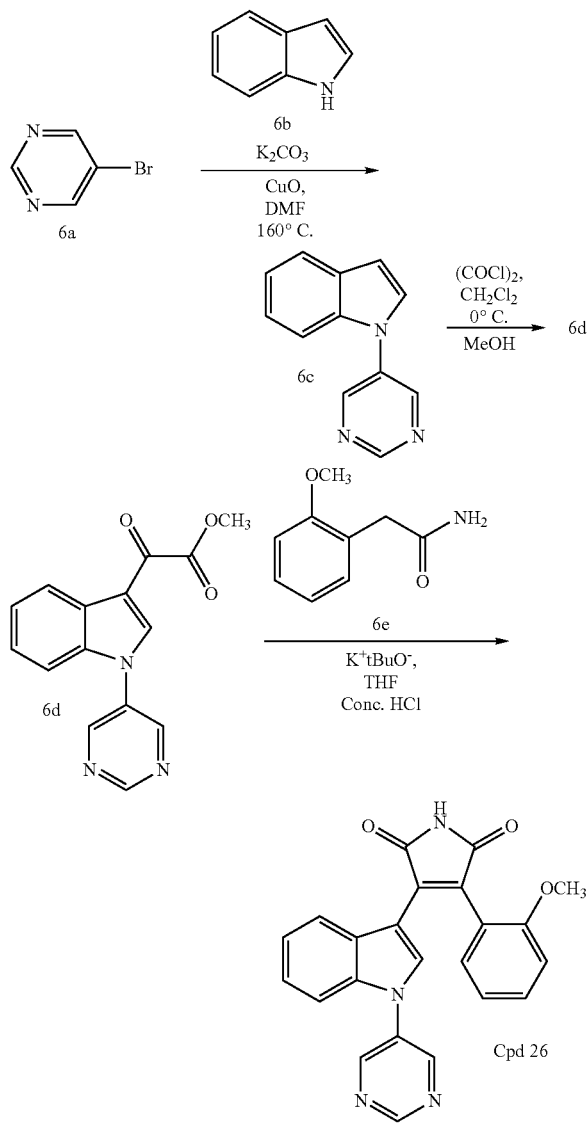

EXAMPLE 7

3-(2-methoxyphenyl)-4-[1-(3-pyridinyl)-1H-indol-3-yl]-1H-pyrrole-2,5-dione (Compound 27)

Indole Compound 6b (2.34 g, 20 mmol) and 3-bromopyridine (3.16 g, 20 mmol) were dissolved in DMF (10 mL) and potassium carbonate (2.76 g, 20 mmol). CuO (130 mg, 1.6 mmol) was added and the reaction was refluxed under argon for 16 h. The mixture was cooled to rt and partitioned between DCM (100 mL) and water (100 mL). The organic layer was washed with water (3×50 mL) and brine (2×50 mL), then dried (Na$_2$SO$_4$) and evaporated in vacuo to a brown oil. The product was purified via flash column chromatography (ethyl acetate:hexane; 1:1) to give Compound 7a (3.16 g, 81%) as a colorless oil. The indole Compound 7a (0.78 g, 4.0 mmol) in DCM (12 mL) was treated with oxalyl chloride (0.52 g, 4.1 mmol) with ice bath cooling and then stirred at ambient temperature for 16 h. The solution was cooled to −65° C. and sodium methoxide (0.46 g, 8.0 mmol) in methanol (10 mL) was added slowly; the reaction was stirred at ambient temperature for 1 h and then evaporated in vacuo to a solid. The solid was extracted with chloroform (25 mL), filtered and the filtrate dried (K$_2$CO$_3$) and evaporated in vacuo to provide a methyl ester Compound 7b (0.73 g, 65%) as a grey solid. $^1$H NMR (CDCl$_3$) δ 8.88 (d, J=2.3 Hz, 1H), 8.77 (dd, J=4.7, 1.3 Hz, 1H), 8.60 (s, 1H), 8.54 (d, J=7.1 Hz, 1H), 7.90 (m, 1H), 7.56 (m, 1H), 7.43 (m, 3H), 3.98 (s, 3H). ES-MS m/z 281 (MH+).

The Compound 7b (0.2 g, 0.71 mmol) and amide Compound 6e (84 mg, 0.51 mmol) were combined in dry THF (5 mL) under argon and cooled in an ice bath as 1M potassium t-butoxide in THF (2.5 mL, 2.5 mmol) was added with stirring over a 5 min period. After 40 min, the reaction was quenched in an ice bath while 12 N HCl (2 mL, 24 mmol) was slowly added. The mixture was stirred for 15 min at rt, made slightly basic by the addition of 3N NaOH and extracted with EtOAc. The organic layers were combined and washed with saturated NaHCO$_3$ and brine, then dried (Na$_2$SO$_4$) and evaporated in vacuo to give a crude solid (0.25 g); The solid was then purified by flash column chromatography (97:3:0.3; DCM:MeOH:NH$_4$OH) to afford Compound 27 (45 mg, 23%) as a yellow flaky solid. Compound 27 was dissolved in excess dilute HCl, then frozen and lyophilized to give the hydrochloride salt. $^1$H NMR (DMSO) δ 8.87 (s, 1H), 8.69 (m, 1H), 8.14 (s, 1H), 8.11 (m, 1H), 7.67 (m, 1H), 7.49 (d, J=8.3 Hz, 1H), 7.41 (m, 1H), 7.32 (m, 1H), 7.16 (t, J=7.7 Hz, 1H), 6.99 (m, 2H), 6.81 (t, J=7.6 Hz, 1H), 6.55 (d, J=8.0 Hz, 1H), 3.33 (s, 3H). ES-MS m/z 396(MH+). Anal. Calcd. for C$_{24}$H$_{17}$N$_3$O$_3$·0.24HCl·0.07H2O: C, 71.11; H, 4.33; Cl, 2.10; N, 10.37; KF, 0.32. Found: C, 70.98; H, 4.12; N, 10.09; Cl, 1.78; KF, 0.1.

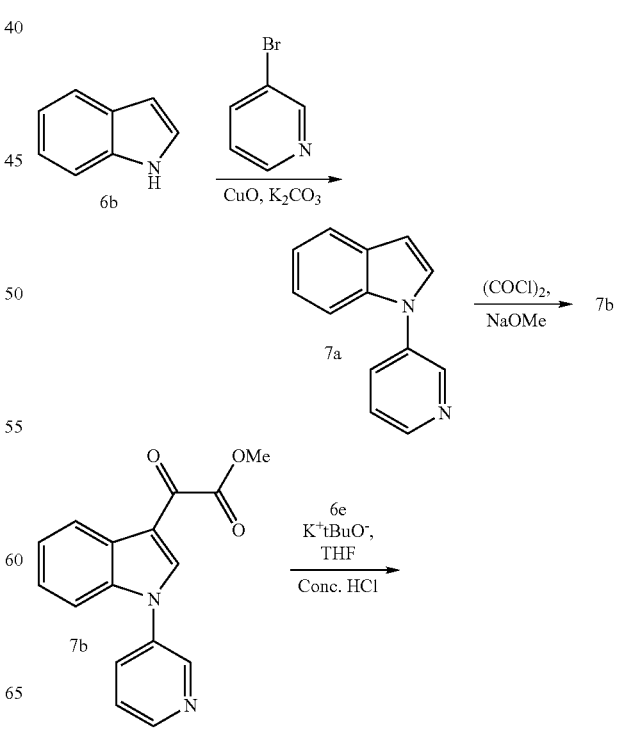

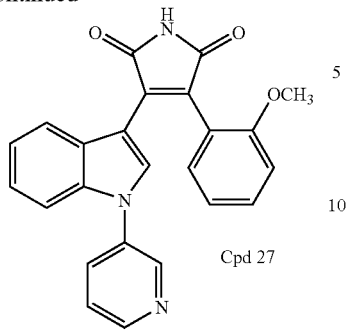

Cpd 27

Using the procedure of Example 7 and the appropriate reagents and starting materials known to those skilled in the art, other compounds of the present invention may be prepared including, but not limited to:

| Cpd | Name | MS m/z (MH+) |
|---|---|---|
| 28 | 3-(2-hydroxyphenyl)-4-[1-(3-pyridinyl)-1H-indol-3-yl]-1H-pyrrole-2,5-dione | 382 |
| 29 | 3-(4-hydroxyphenyl)-4-[1-(3-pyridinyl)-1H-indol-3-yl]-1H-pyrrole-2,5-dione | 382 |
| 51 | 3-[1-(5-bromo-2-pyridinyl)-1H-indol-3-yl]-4-(2,5-dichlorobenzo[b]thien-3-yl)-1H-pyrrole-2,5-dione | 534 |
| 52 | 3-[1-(3-pyridinyl)-1H-indol-3-yl]-4-(2-thienyl)-1H-pyrrole-2,5-dione | 372 |

EXAMPLE 8

3-(1-naphthalenyl)-4-[1-(5-pyrimidinyl)-1H-indol-3-yl]-1H-pyrrole-2,5-dione (Compound 30)

The methyl ester Compound 6d (0.2 g, 0.71 mmol) and amide Compound 8a (94 mg, 0.51 mmol) were combined in dry THF (5 mL) under argon and cooled in an ice bath as 1M potassium t-butoxide in THF (2.5 mL, 2.5 mmol) was added with stirring over a 5 min period. After 40 min, the reaction was quenched in an ice bath while 12 N HCl (2 mL, 24 mmol) was slowly added. The mixture was stirred for 15 min at rt, made slightly basic by the addition of 3N NaOH and extracted with EtOAc. The organic layers were combined and washed with saturated NaHCO$_3$ and brine, then dried (Na$_2$SO$_4$) and evaporated in vacuo to give a crude solid (0.25 g). The solid was then purified by flash column chromatography (97:3:0.3; DCM:MeOH:NH$_4$OH) to afford Compound 30 (30 mg, 15%) as a yellow flaky solid. Compound 30 was dissolved in excess dilute HCl, then frozen and lyophilized to give the hydrochloride salt. $^1$H NMR (CD$_3$OD) δ 9.22 (s, 1H), 9.06 (s, 2H), 8.21 (s, 1H), 7.99 (m, 1H), 7.90 (m, 1H), 7.77 (m, 1H), 7.53 (m, 2H), 7.39 (m, 3H), 7.05 (t, J=7.8 Hz, 1H), 6.53 (t, J=7.9 Hz, 1H), 6.31 (d, J=8.3 Hz, 1H). ES-MS m/z 417(MH+).

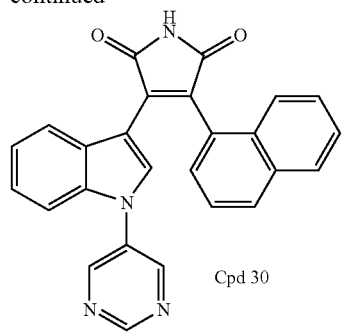

Cpd 30

EXAMPLE 9

3-[2-bromo-5-[3-(dimethylamino)propyl]phenyl]-4-(1H-indol-3-yl)-1H-pyrrole-2,5-dione (Compound 24)

Potassium carbonate (2.42 g, 17.5 mmol) and 3-dimethylaminopropyl chloride hydrochloride (1.03 g, 6.51 mmol) were added to phenol Compound 9a (0.92 g, 4.34 mmol) in DMF (20 mL) and heated in an oilbath at 60 C for 3 h. The mixture was cooled and partitioned between DCM (75 mL) and water (25 mL); the DCM was washed twice with water and once with brine, then dried (K$_2$CO$_3$) and evaporated in vacuo to an oil Compound 9b (1.08 g). $^1$H NMR (CDCl$_3$) δ 1.95 (m, 2H), 2.30 (s, 3H), 2.45 (m, 2H), 3.80 (s, 2H), 4.0 (m, 2H), 6.78 (bd d, J=8.0 Hz, 1H), 7.05 (bd s, 1H), 7.45 (d, J=8.0 Hz, 1H). ES-MS m/z 297 (MH+). This was dissolved in t-butanol (30 mL) and potassium hydroxide (1.02 g, 17.5 mmol) was added and the reaction refluxed for 45 min. The reaction was cooled and evaporated in vacuo to a brown oil Compound 9c (0.35 g); ES-MS m/z 315 (MH+). A portion of the amide Compound 9c (350 mg, 1.11 mmol) and the ester Compound 1b (250 mg, 1.22 mmol) in THF (20 mL) were stirred at rt as 60% NaH (266 mg, 6.66 mmol) was added. After 5 h, the reaction was quenched with 12 N HCl (4.0 mL, 48 mmol), stirred for 10 min and then partitioned between EA and saturated sodium bicarbonate. The organic layer was washed once with sodium bicarbonate and twice with brine, then dried (Na$_2$SO$_4$) and evaporated in vacuo to give the crude product of Compound 24 (250 mg) as a yellow oil. The product was purified by preparative TLC to give Compound 24. $^1$H NMR (CDCl$_3$) δ 1.90 (m, 2H), 2.30 (s, 3H), 2.45 (m, 2H), 3.95 (m, 2H), 6.65 (d, J=8.0 Hz, 1H), 6.80 (m, 1H), 6.85 (s, 1H), 7.10–7.60 (m, 4H), 8.05 (s, 1H), 8.80 (s, 1H); ES-MS m/z 468 (MH+).

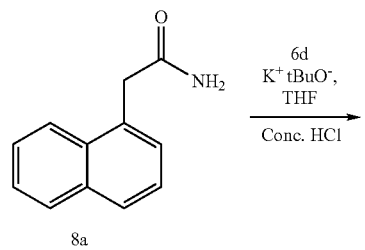

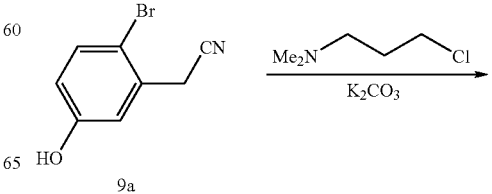

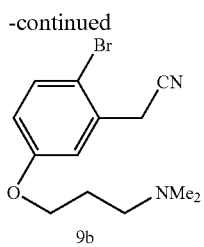

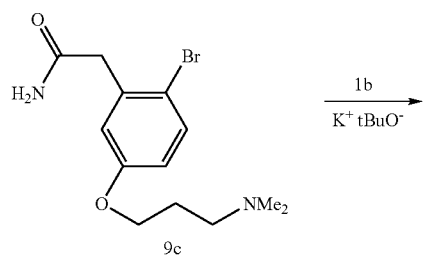

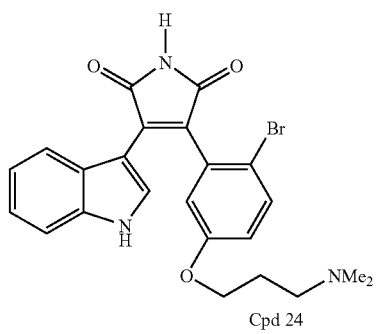

The organic extract was dried (Na$_2$SO$_4$) and evaporated in vacuo to a solid (6.25 g), which was triturated with diethyl ether (100 mL) and filtered to afford a Compound 10b (3.52 g, 67%) as a white solid. Compound 10b (5 g, 28.6 mmol) was combined with a silyl-protected 3-bromo-1-propanol Compound 10c (8.33 g, 32.9 mmol) in the presence of Cs$_2$CO$_3$ (12.11 g, 37 mmol) in DMF (50 mL) at 68° C. for 3 h. The mixture was cooled to rt, water was added and then the mixture was extracted with EtOAc several times. The organic layers were combined and washed with brine, then dried (Na$_2$SO$_4$) and evaporated in vacuo to provide an oil. The oil was purified by flash column chromatography (95:5:0.5; DCM:MeOH:NH$_4$OH) to give an amide Compound 10d (9.9 g, 100%). $^1$H NMR (CDCl$_3$) δ 7.65 (m, 1H), 7.38 (m, 2H), 7.13 (m, 1H), 6.53 (bd s, 1H), 5.44 (bd s, 1H), 4.44 (t, J=6.82 Hz, 2H), 3.93 (s, 2H), 3.56 (t, J=5.73 Hz, 2H), 2.08 (m, 2H), 0.89 (s, 9H), 0.01 (s, 6H). ES-MS m/z 348 (MH$^+$).

The methyl ester Compound 10e (0.1 g, 0.62 mmol) and amide Compound 10d (0.15 g, 0.44 mmol) were combined in dry THF (3 mL) under argon and cooled in an ice bath as 1M potassium t-butoxide in THF (2.2 mL, 2.2 mmol) was added while stirring the mixture over a 15 min period. After 40 min, the reaction was quenched in an ice bath while 12 N HCl (2 mL) was slowly added. The mixture was stirred for 15 min at room temperature, made slightly basic by the addition of 3N NaOH and extracted with EtOAc. The organic layers were combined and washed with saturated NaHCO$_3$ and brine, then dried (Na$_2$SO$_4$) and evaporated in vacuo to give a crude solid. The solid was purified by flash column chromatography (95:5:0.5; DCM:MeOH:NH$_4$OH) to afford Compound 53 (60 mg, 40%) as an orange solid. $^1$H NMR (DMSO) δ 7.70 (d, J=8.5 Hz, 1H), 7.54 (m, 2H), 7.40 (m, 5H), 7.07 (m, 1H), 4.59 (t, J=4.9 Hz, 1H), 4.49 (t, J=6.7 Hz, 2H), 3.38 (m, 2H), 1.95 (m, 2H). ES-MS m/z 348 (MH$^+$)

Using the procedure of Example 9 and the appropriate reagents and starting materials known to those skilled in the art, other compounds of the present invention may be prepared including, but not limited to:

| Cpd | Name | ES-MS m/z (MH$^+$) |
|---|---|---|
| 25 | 3-(2-bromo-5-[3-(dimethylamino)propyl]phenyl]-4-(1-phenyl-1H-indol-3-yl)-1H-pyrrole-2,5-dione | 544 |

EXAMPLE 10

3-[1-(3-hydroxypropyl)-1H-indazol-3-yl]-4-phenyl-1H-pyrrole-2,5-dione (Compound 53)

Indazole acid Compound 10a (5.28 g, 30 mmol) was dissolved in DCM (120 mL) and DMF (30 mL) under argon. HOBT (4.45 g, 33 mmol) and DCC (6.51 g, 32 mmol) were added and the mixture was stirred at ambient temperature for 1 h. Ammonium hydroxide (28%, 2.7 g, 44 mmol) was added over 5 min and the mixture was then stirred at ambient temperature for 16 h. A white solid was filtered off, diluted with DCM (150 mL) and filtered again. The DCM solution was extracted four times with 5% NaHCO$_3$ (150 mL). The combined aqueous solution was treated with sodium chloride (190 g) and extracted with ethyl acetate (6×300 mL).

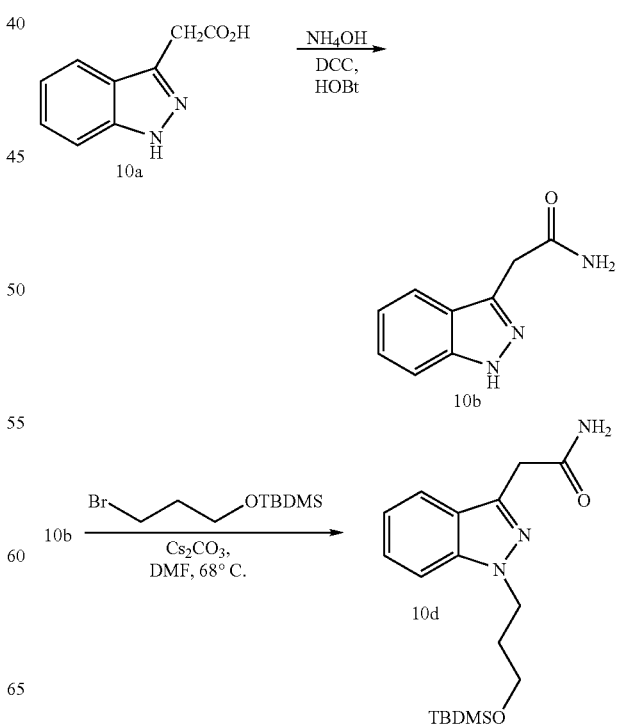

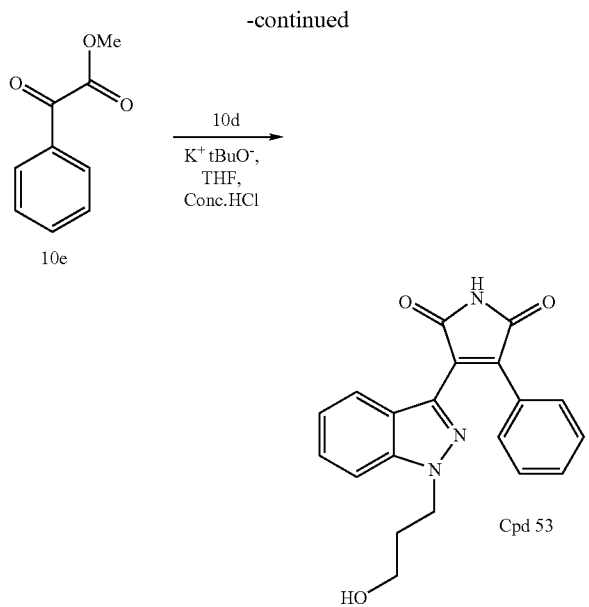

Cpd 53

Using the procedure of Example 10 and the appropriate reagents and starting materials known to those skilled in the art, other compounds of the present invention may be prepared including, but not limited to:

| Cpd | Name | ES-MS m/z (MH+) |
|---|---|---|
| 54 | 3-[1-(3-hydroxypropyl)-1H-indazol-3-yl]-4-(2-methoxyphenyl)-1H-pyrrole-2,5-dione | 378 |

EXAMPLE 11

5-{5-Chloro-3-[4-(2-methoxyphenyl)-2,5-dioxo-2,5-dihydro-1H-pyrrol-3-yl]-indol-1-yl}-nicotinic acid (Compound 56)

5-{5-Chloro-3-[4-(2-methoxyphenyl)-2,5-dioxo-2,5-dihydro-1H-pyrrol-3-yl]-indol-1-yl}-nicotinic acid methyl ester (Compound 57)

5-Chloroindole 11a (2.00 g, 13.2 mmol) and methyl-5-bromonicotinate 11b (2.85 g, 13.2 mmol) were dissolved in DMF (8 mL) and potassium carbonate (1.82 g, 13.2 mmol) and CuO (87.4 mg, 1.1 mmol) were added in and the reaction was refluxed under nitrogen for 16 h. The reaction was cooled to room temperature and partitioned between ethyl acetate (100 mL) and water (100 mL). The organic layer was washed 3 times with water (33 mL), twice with brine (33 mL), dried (Na$_2$SO$_4$) and evaporated in vacuo to a brown solid. This was purified via flash column chromatography (DCM:MeOH:AcOH 50:50:0.5) to give a brown solid. The solid was dissolved in DCM and filtered. The filtrate was conc. and dried to give 11c (1.74 g, 48%). $^1$H NMR (DMSO-d$_6$) δ 9.08 (s, 2H), 8.38 (s, 1H), 7.91 (d, J=3.3 Hz, 1H), 7.76 (d, J=1.9 Hz, 1H), 7.60 (d, J=8.8 Hz, 1H), 7.25 (dd, J=2.0, 8.8 Hz, 1H), 6.78 (d, J=3.1 Hz, 1H). ES-MS m/z 271 (M−).

A suspension of Compound 11c (1.00 g, 3.7 mmol) in dichloromethane:methanol (6:1, 20 mL) was stirred and cooled in an ice bath while 5.5 mL of a 2.0 M solution of TMSCHN$_2$ in hexane was added dropwise over 10 min. The mixture was allowed to warm up to rt and stirred at rt overnight. The reaction mixture was evaporated in vacuo and purified via flash column chromatography (ethyl acetate:hexane, 30:70) to give 11d (0.48 g, 45%). $^1$H NMR (CDCl$_3$) δ 9.21 (d, J=1.8 Hz, 1H), 8.98 (d, J=2.6 Hz, 1H), 8.41 (t, 1H), 7.67 (d, J=1.9 Hz, 1H), 7.43 (d, J=8.8 Hz, 1H), 7.37 (d, J=3.3 Hz, 1H), 7.21 (m, 1H), 6.71 (d, J=2.9 Hz, 1H), 4.01 (s, 3H). ES-MS m/z 287 (MH+).

A solution of Compound 11d (0.21 g, 0.74 mmol) in dichloromethane (3 mL) was treated with oxalyl chloride (97 mg, 0.76 mmol) with ice bath cooling and then stirred at ambient temperature overnight. Additional oxalyl chloride (97 mg, 0.76 mmol) was added and reaction stirred at ambient temperature overnight. The reaction mixture was heated to 30° C. for 5 h and was then cooled to −65° C. and sodium methoxide (81 mg, 1.5 mmol) in methanol (3 mL) was added in slowly, and the reaction was allowed to come to rt. The reaction mixture was evaporated in vacuo and purified via flash column chromatography (ethyl acetate:hexane 40:60) to give 11e (120 mg, 44%). $^1$H NMR (CDCl$_3$) δ 9.36 (s, 1H), 9.03 (d, J=2.5 Hz, 1H), 8.64 (s, 1H), 8.54 (d, J=1.1 Hz, 1H), 8.48 (t, 1H), 7.36 (s, 2H), 4.03 (s, 3H), 3.98 (s, 3H). ES-MS m/z 373 (MH+).

The ester 11e (480 mg, 1.3 mmol) and amide 11f (150 mg, 0.91 mmol) were combined in dry THF (7 mL) under nitrogen and cooled to 0° C. as 1M potassium t-butoxide in THF (3.6 mL, 3.6 mmol) was added with stirring over the next 10 min. The reaction was warmed to ambient temperature and stirred at room temperature for 3 h. The reaction mixture was cooled to 0° C., quenched with con. HCl (4.5 ml) and warmed to room temperature and stirred for 1 hr. The organic solution was diluted with ethyl acetate (200 ml) and washed with water (10 ml), dried (Na$_2$SO$_4$) and evaporated in vacuo. The crude material was purified via flash column chromatography (DCM:MeOH:NH$_4$OH, 99:1:2; then DCM:MeOH:HOAc, 90:10:0.5) to give Compounds 57 (108 mg, 24%) and 56 (280 mg, 65%). For Compound 56: $^1$H NMR (DMSO-d$_6$) δ 9.09 (s, 1H), 8.91 (s, 1H), 8.31–8.25 (m, 1H), 7.49–7.19 (m, 7H), 7.04 (t, 2H), 3.30 (s, 3H). ES-MS m/z 474 (MH+). For Compound 57: $^1$H NMR (CDCl$_3$) δ 9.29 (d, J=1.7 Hz, 1H), 9.01 (d, J=2.6 Hz, 1H), 8.45 (t, 1H), 8.16 (s, 1H), 7.51–7.32 (m, 3H), 7.16–7.09 (m, 2H), 6.90 (d, J=8.4 Hz, 1H), 6.43 (d, J=1.9 Hz, 1H), 4.48 (s, 3H), 4.03 (s, 3H). ES-MS m/z 488 (MH+).

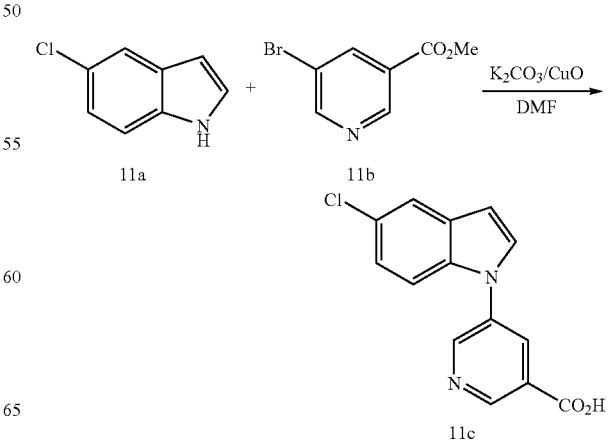

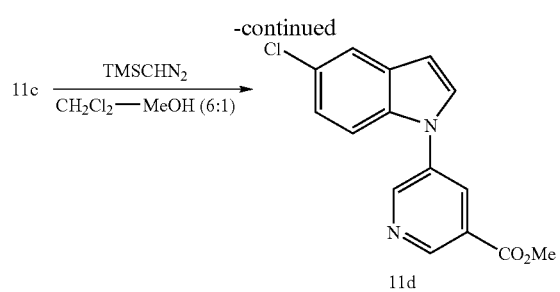

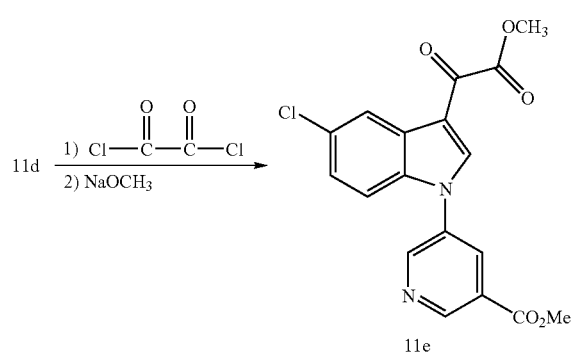

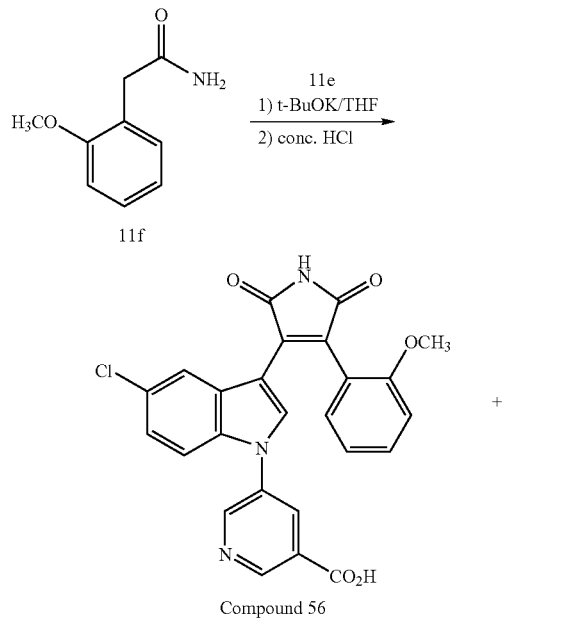

EXAMPLE 12

5-{5-Chloro-3-[4-(2-methoxyphenyl)-2,5-dioxo-2,5-dihydro-1H-pyrrol-3-yl]-indol-1-yl}-nicotinamide (Compound 58)

To a stirring solution of Compound 56 (80 mg, 0.17 mmol) in DCM (2 mL) and DMF (0.5 mL) was added HOBT (25.7 mg, 0.19 mmol) and DCC (37 mg, 0.18 mmol). The reaction was stirred at room temperature for 30 min, then 28% aqueous $NH_3$ (15 mg, 0.36 mmol) was added. The reaction stirred at room temperature overnight. The reaction mixture was filtered and the filtered solid was washed with DCM (2 mL). The filtrate was diluted with ethyl acetate (6 mL), washed twice with $NaHCO_3$ (2 mL), dried ($Na_2SO_4$) and evaporated in vacuo. The crude product was purified via flash column chromatography (DCM:MeOH:$NH_4OH$ 93:5:2) to give Compound 58 (36.7 mg, 46%). Compound 58 was dissolved in methanol and treated with 1N HCl/$CH_3CN$ (2:1) and lyophilized to give the HCl salt. $^1$HNMR (DMSO-$d_6$) δ 11.2 (s, 1H), 9.11 (s, 1H), 9.03 (s, 1H), 8.45 (s, 1H), 8.32 (d, J=12.0, 2H), 7.80 (s, 1H), 7.58–7.47 (m, 3H), 7.34–7.01 (m, 3H), 6.42 (s, 1H), 3.34 (s, 3H). ES-MS m/z 473 (MH$^+$).

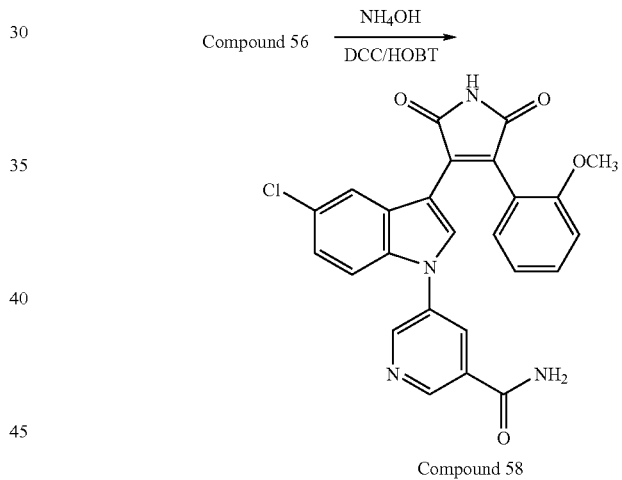

EXAMPLE 13

As a specific example of an oral composition, 100 mg of Compound 26 is formulated with sufficient finely divided lactose to provide a total amount of 580 to 590 mg to fill a size O hard gel capsule.

BIOLOGICAL EXPERIMENTAL EXAMPLES

The utility of the compounds to treat kinase or dual-kinase mediated disorders (in particular, kinases selected from protein kinase C and glycogen synthase kinase-3; and, more particularly, kinases selected from protein kinase C α, protein kinase C β-II, protein kinase C γ or glycogen synthase kinase-3β) was determined using the following procedures.

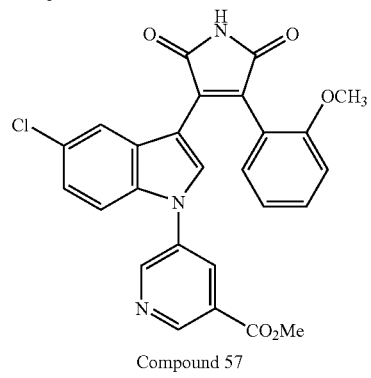

EXAMPLE 1

Protein Kinase C Histone-Based Assay

Compounds were evaluated for PKC selectivity using histone III as the substrate. The PKC isoforms α, β-II or γ were added to a reaction mixture that contained 20 mM HEPES, (pH 7.4), 940 µM $CaCl_2$, 10 mM $MgCl_2$, 1 mM EGTA. 100 µg/mL phosphatidylserine, 20 µg/mL diacylglycerol, 30 µM ATP, 1 µCi ($^{33}$P)ATP and 200 µg/mL histone III. The reaction was incubated for 10 min at 30° C. Reactions were terminated by TCA precipitation and spotting on Whatman P81 filters. Filters were washed in 75 mM phosphoric acid and the radioactivity quantified by liquid scintillation counting.

Table 1 shows the biological activity in the histone based assay as $IC_{50}$ values (µM) for representative compounds of the present invention.

TABLE 1

PKC Activity ($IC_{50}$ µM, Histone Based Assay)

| Cpd | Beta II | Alpha | Gamma |
|---|---|---|---|
| 7 | 68% @ 1 µM | 39% @ 10 µM | 54% @ 10 µM |
| 9 | 40% @ 1 µM | 27% @ 10 µM | 15% @ 10 µM |
| 21 | 0.051 | 0.117 | 0.477 |
| 26 | 0.607 | 2.07 | 29% @ 10 µM |
| 27 | 0.527 | 66% @ 10 µM | — |
| 31 | 0.081 | 0.083 | — |
| 55 | 0.107 | 0.412 | 0.282 |
| 56 | 0.042 | 0.592 | 0.832 |
| 58 | 0.032 | 0.816 | 1.272 |

The assay used to generate the data in this table has approximately ± 30 percent margin of error.

EXAMPLE 2

Glycogen Synthase Kinase-3 Assay

Compounds were tested for the ability to inhibit recombinant rabbit GSK-3β using the following protocol. The test compound was added to a reaction mixture containing Protein phosphatase inhibitor-2 (PPI-2) (Calbiochem) (45 ng), rabbit GSK-3β (New England Biolabs) (0.75 units) and $^{33}$P-ATP (1 µCi) in 50 mM Tris-HCl (pH 8.0), 10 mM $MgCl_2$, 0.1% BSA, 1 mM DTT and 100 µM Sodium Vanadate. The mixture was reacted for 90 minutes at 30° C. to allow phosphorylation of the PPI-2 protein and then the protein in the reaction was precipitated using 10% TCA. The precipitated protein was collected on filter plates (Multi-Screen-DV/Millipore), which were subsequently washed. Finally, the radioactivity was quantified using a TopCount Scintillation Counter (Packard). GSK-3 inhibitory compounds resulted in less phosphorylated PPI-2 and thus a lower radioactive signal in the precipitated protein. Staurosporine or Valproate, known inhibitors of GSK-3β, were used as a positive control for screening.

Table 2 shows the biological activity in the GSK-3β assay as $IC_{50}$ values (µM) for representative compounds of the present invention.

TABLE 2

GSK-3β Assay Activity ($IC_{50}$ µM)

| Cpd | GSK-3β |
|---|---|
| 2 | 72% @ 200 nM |
| 7 | 0.390 |

TABLE 2-continued

GSK-3β Assay Activity ($IC_{50}$ µM)

| Cpd | GSK-3β |
|---|---|
| 8 | 0.039 |
| 9 | 0.027 |
| 12 | 64% @ 200 nM |
| 22 | 62% @ 200 nM |
| 23 | 67% @ 200 nM |
| 25 | 0.110 |
| 26 | 0.008 |
| 27 | 0.026 |
| 28 | 0.068 |
| 29 | 0.096 |
| 41 | 81% @ 200 nM |
| 46 | 45% @ 200 nM |
| 55 | 0.025 |
| 56 | 0.051 |
| 57 | 0.040 |
| 58 | 0.018 |

The results from the foregoing indicate that a compound of the present invention would be expected to be useful in treating or ameliorating a kinase or dual-kinase mediated disorder.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

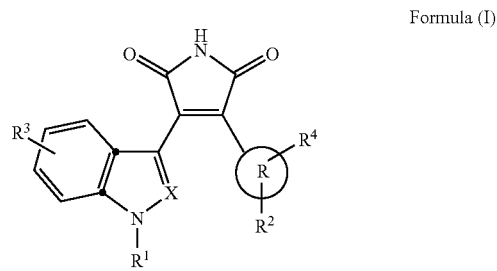

Formula (I)

wherein

R is selected from the group consisting of phenyl and naphthyl;

$R^1$ is -heteroaryl-$R^6$; wherein a heteroaryl ring carbon atom forms the point of attachment to the indole nitrogen atom;

$R^5$ is 1 to 2 substituents independently selected from the group consisting of hydrogen, —O—$(C_{1-8})$alkyl, —O—$(C_{1-8})$alkyl-OH, —O—$(C_{1-8})$alkyl-O—$(C_{1-8})$alkyl, —O—$(C_{1-8})$alkyl-$NH_2$, —O—$(C_{1-8})$alkyl-NH$(C_{1-8}$alkyl), —O—$(C_{1-8})$alkyl-N$(C_{1-8}$alkyl$)_2$, —O—$(C_{1-8})$alkyl-S—$(C_{1-8})$alkyl, —O—$(C_{1-8})$alkyl-$SO_2$—

($C_{1-8}$)alkyl, —O—($C_{1-8}$)alkyl-$SO_2$—$NH_2$, —O—($C_{1-8}$) alkyl-$SO_2$—NH($C_{1-8}$alkyl), —O—($C_{1-8}$)alkyl-$SO_2$—N($C_{1-8}$alkyl)$_2$, —O—C(O)H, —O—C(O)—($C_{1-8}$) alkyl, —O—C(O)—$NH_2$, —O—C(O)—NH($C_{1-8}$ alkyl), —O—C(O)—N($C_{1-8}$ alkyl)$_2$, —O—($C_{1-8}$)alkyl-C(O)H, —O—($C_{1-8}$)alkyl-C(O)—O—($C_{1-8}$)alkyl, —O—($C_{1-8}$)alkyl-C(O))$_2$H, —O—($C_{1-8}$)alkyl-C(O)—O—($C_{1-8}$)alkyl, —O—($C_{1-8}$) alkyl-C(O)-$NH_2$, —O—($C_{1-8}$)alkyl-C(O)—NH($C_{1-8}$ alkyl), —O—($C_{1-8}$)alkyl-C(O)—N($C_{1-8}$alkyl)$_2$, —C(O)H, —C(O)—($C_{1-8}$)alkyl, —$CO_2$H, —C(O)—O—($C_{1-8}$)alkyl, —C(O)—$NH_2$, —C(NH)—$NH_2$, —C(O)—NH($C_{1-8}$alkyl), —C(O)—N($C_{1-8}$ alkyl)$_2$, —SH, —S—($C_{1-8}$)alkyl, —S—($C_{1-8}$)alkyl-S—($C_{1-8}$)alkyl, —S—($C_{1-8}$)alkyl-O—($C_{1-8}$)alkyl, —S—($C_{1-8}$)alkyl-O—($C_{1-8}$)alkyl-OH, —S—($C_{1-8}$)alkyl-O—($C_{1-8}$)alkyl-$NH_2$, —S—($C_{1-8}$)alkyl-O—($C_{1-8}$) alkyl-NH($C_{1-8}$ alkyl), —S—($C_{1-8}$)alkyl-O—($C_{1-8}$)alkyl-N($C_{1-8}$ alkyl)$_2$, —S—($C_{1-8}$)alkyl-NH($C_{1-8}$alkyl), —$SO_2$—($C_{1-8}$)alkyl, —$SO_2$—$NH_2$, —$SO_2$—NH($C_{1-8}$alkyl), —$SO_2$—N($C_{1-8}$alkyl)$_2$, —N—$R^7$, —($C_{1-4}$)alkyl-N—$R^7$, cyano, (halo)$_{1-3}$, hydroxy, nitro, oxo, -cycloalkyl-$R^6$, —($C_{1-4}$)alkyl-cycloalkyl-$R^6$, -heterocyclyl-$R^6$, —($C_{1-4}$)alkyl-heterocyclyl-$R^6$, -aryl-$R^6$, —($C_{1-4}$)alkyl-aryl-$R^6$, -heteroaryl-$R^6$ and —($C_{1-4}$)alkyl-heterocyclyl-$R^6$;

$R^6$ is 1 to 4 substituents attached to a carbon or nitrogen atom independently selected from the group consisting of hydrogen, —$C_{1-8}$alkyl, —($C_{1-8}$)alkyl-(halo)$_{1-3}$ and —($C_{1-8}$)alkyl-OH; with the proviso that, when R is attached to a carbon atom, $R^6$ is further selected from the group consisting of —$C_{1-8}$alkoxy, —C(O)$NH_2$, —$NH_2$, —NH($C_{1-8}$alkyl), —N($C_{1-8}$alkyl)$_2$, cyano, halo, —($C_{1-8}$)alkoxy-(halo)$_{1-3}$, hydroxy and nitro;

$R^7$ is 2 substituents independently selected from the group consisting of hydrogen, —$C_{1-8}$alkyl, —$C_{2-8}$alkenyl, —$C_{2-8}$alkynyl, —($C_{1-8}$)alkyl-OH, —($C_{1-8}$)alkyl-O—($C_{1-8}$)alkyl, —($C_{1-8}$)alkyl-$NH_2$, —($C_{1-8}$)alkyl-NH($C_{1-8}$ alkyl), —($C_{1-8}$)alkyl-N($C_{1-8}$alkyl)$_2$, —($C_{1-8}$)alkyl-S—($C_{1-8}$)alkyl, —C(O)—($C_{1-8}$)alkyl, —C(O)—O—($C_{1-8}$) alkyl, —C(O)—$NH_2$, —C(O)—NH($C_{1-8}$alkyl), —C(O)—N($C_{1-8}$alkyl)$_2$, —$SO_2$—($C_{1-8}$)alkyl, —$SO_2$—$NH_2$, —$SO_2$—NH($C_{1-8}$alkyl), —$SO_2$—N($C_{1-8}$ alkyl)$_2$, —C(N)—$NH_2$, -cycloalkyl-$R^8$, —($C_{1-8}$)alkyl-heterocyclyl-$R^8$, -aryl-$R^8$, —($C_{1-8}$)alkyl-aryl-$R^8$ and —($C_{1-8}$)alkyl-heteroaryl-$R^8$;

$R^8$ is 1 to 4 substituents attached to a carbon or nitrogen atom independently selected from the group consisting of hydrogen, —$C_{1-8}$alkyl, —($C_{1-8}$)alkyl-(halo)$_{1-3}$ or —($C_{1-8}$)alkyl-OH; with the proviso that, when $R^8$ is attached to a carbon atom, $R^8$ is further selected from —$C_{1-8}$alkoxy, —$NH_2$, —NH($C_{1-8}$alkyl), —N($C_{1-8}$ alkyl)$_2$, cyano, halo, —($C_{1-8}$)alkoxy-(halo)$_{1-3}$, hydroxy and nitro;

$R^2$ is one substituent attached to a carbon atom selected from the group consisting of hydrogen, —$C_{1-8}$alkyl-$R^5$, —$C_{2-8}$alkenyl-$R^5$, —$C_{2-8}$alkynyl-$R^5$, —C(O)H, —C(O)—($C_{1-8}$)alkyl-$R^9$, —C(O)—$NH_2$, —C(O)—NH($C_{1-8}$alkyl-$R^9$), —C(O)—N($C_{1-8}$alkyl-$R^9$)$_2$, —C(O)—NH(aryl-$R^8$), —C(O)-cycloalkyl-$R^8$, —C(O)-heterocyclyl-$R^8$, —C(O)-aryl-$R^8$, —C(O)-heteroaryl-$R^8$, —$CO_2$H, —C(O)—O—($C_{1-8}$)alkyl-$R^9$, —C(O)—O-aryl-$R^8$, —$SO_2$—($C_{1-8}$)alkyl-$R^9$, —$SO_2$-aryl-$R^8$, -cycloalkyl-$R^6$, -aryl-$R^6$ or —($C_{1-8}$)alkyl-N—$R^7$, —$C_{1-8}$alkoxy-$R^5$, —N—$R^7$, cyano, halogen, hydroxy, nitro, oxo (wherein oxo is attached to a saturated carbon atom), -heterocyclyl-$R^6$ and -heteroaryl-$R^6$;

$R^9$ is 1 to 2 substituents independently selected from the group consisting of hydrogen, —$C_{1-8}$alkoxy, —$NH_2$, —NH($C_{1-8}$alkyl), —N($C_{1-8}$alkyl)$_2$, cyano, (halo)$_{1-3}$, hydroxy and nitro;

$R^3$ is 1 to 4 substituents attached to a carbon atom independently selected from the group consisting of hydrogen, —$C_{1-8}$alkyl-$R^{10}$, —$C_{2-8}$alkenyl-$R^{10}$, —$C_{2-8}$ alkynyl-$R^{10}$, —$C_{1-8}$alkoxy-$R^{10}$, —C(O)H, —C(O)—($C_{1-8}$)alkyl-$R^9$, —C(O)—$NH_2$, —C(O)—NH($C_{1-8}$ alkyl-$R^9$), —C(O)—N($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O—($C_{1-8}$)alkyl-$R^9$, —C(O)—O-aryl-$R^8$, —$SO_2$—($C_{1-8}$)alkyl-$R^9$, —$SO_2$-aryl-$R^8$, —N—$R^7$, —($C_{1-8}$)alkyl-N—$R^7$, cyano, halogen, hydroxy, nitro, -cycloalkyl-$R^8$, -heterocyclyl-$R^8$, -aryl-$R^8$ and -heteroaryl-$R^8$;

$R^4$ is 1 to 4 substituents attached to a carbon atom independently selected from the group consisting of hydrogen, —$C_{1-8}$alkyl-$R^{10}$, —$C_{2-8}$alkenyl-$R^{10}$, —$C_{2-8}$ alkynyl-$R^{10}$, —$C_{1-8}$alkoxy-$R^{10}$, —C(O)H, —C(O)—($C_{1-8}$)alkyl-$R^9$, —C(O)—$NH_2$, —C(O)—NH($C_{1-8}$ alkyl-$R^9$), —C(O)—N($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O—($C_{1-8}$)alkyl-$R^9$, —C(O)—O-aryl-$R^8$, —SH, —S—($C_{1-8}$)alkyl-$R^{10}$, —$SO_2$—($C_{1-8}$)alkyl-$R^9$, —$SO_2$-aryl-$R^8$, —$SO_2$—$NH_2$, —$SO_2$—NH($C_{1-8}$alkyl-$R^9$), —$SO_2$—N($C_{1-8}$alkyl-$R^9$)$_2$, —N—$R^7$, —($C_{1-8}$) alkyl-N—$R^7$, cyano, halogen, hydroxy, nitro, -cycloalkyl-$R^8$, -heterocyclyl-$R^8$, -aryl-$R^8$ and -heteroaryl-$R^8$;

$R^{10}$ is 1 to 2 substituents independently selected from the group consisting of hydrogen, —$NH_2$, —NH($C_{1-8}$ alkyl), —N($C_{1-8}$alkyl)$_2$, cyano, (halo)$_{1-3}$, hydroxy, nitro and oxo;

X is $CR^{11}$;

$R^{11}$ is hydrogen;

and pharmaceutically acceptable salts thereof.

2. The compound of claim 1 wherein $R^1$ is selected from the group consisting of -pyridinyl-$R^6$, -pyrimidinyl-$R^6$, -quinolinyl-$R^6$ and -benzothienyl-$R^6$; wherein a pyridinyl, pyrimidinyl, quinolinyl or benzothienyl ring carbon atom forms the point of attachment to the indole nitrogen atom.

3. The compound of claim 1 wherein $R^5$ is 1 to 2 substituents independently selected from the group consisting of hydrogen, —O—($C_{1-4}$)alkyl, —O—($C_{1-4}$)alkyl-OH, —O—($C_{1-4}$)alkyl-O—($C_{1-4}$)alkyl, —O—($C_{1-4}$)alkyl-$NH_2$, —O—($C_{1-4}$)alkyl-NH($C_{1-4}$alkyl), —O—($C_{1-4}$)alkyl-N($C_{1-4}$ alkyl)$_2$, —O—($C_{1-4}$)alkyl-S—($C_{1-4}$)alkyl, —O—($C_{1-4}$) alkyl-$SO_2$—($C_{1-4}$)alkyl, —O—($C_{1-4}$)alkyl-$SO_2$—$NH_2$, —O—($C_{1-4}$)alkyl-$SO_2$—NH($C_{1-4}$alkyl), —O—($C_{1-4}$)alkyl-$SO_2$—N($C_{1-4}$alkyl)$_2$, —O—C(O)H, —O—C(O)—($C_{1-4}$) alkyl, —O—C(O)—$NH_2$, —O—C(O)—NH($C_{1-4}$alkyl), —O—C(O)—N($C_{1-4}$alkyl)$_2$, —O—($C_{1-4}$)alkyl-C(O)H, —O—($C_{1-4}$)alkyl-C(O)—($C_{1-4}$)alkyl, —O—($C_{1-4}$)alkyl-$CO_2$H, —O—($C_{1-4}$)alkyl-C(O)—O—($C_{1-4}$)alkyl, —O—($C_{1-4}$)alkyl-C(O)—$NH_2$, —O—($C_{1-4}$)alkyl-C(O)—NH($C_{1-4}$ alkyl), —O—($C_{1-4}$)alkyl-C(O)—N($C_{1-4}$alkyl)$_2$, —C(O)H, —C(O)—($C_{1-4}$)alkyl, —$CO_2$H, —C(O)—O—($C_{1-4}$)alkyl, —C(O)—$NH_2$, —C(NH)—$NH_2$, —C(O)—NH($C_{1-4}$alkyl), —C(O)—N($C_{1-4}$alkyl)$_2$, —SH, —S—($C_{1-4}$)alkyl, —S—($C_{1-4}$)alkyl-S—($C_{1-4}$)alkyl, —S—($C_{1-4}$)alkyl-O—($C_{1-4}$)alkyl, —S—($C_{1-4}$)alkyl-O—($C_{1-4}$)alkyl-OH, —S—($C_{1-4}$)

alkyl-O—($C_{1-4}$)alkyl-NH$_2$, —S—($C_{14}$)alkyl-O—($C_{1-4}$)alkyl-NH($C_{1-4}$alkyl), —S—($C_{1-4}$)alkyl-O—($C_{1-4}$)alkyl-N($C_{1-4}$alkyl)$_2$, —S—($C_{1-4}$)alkyl-NH($C_{1-4}$alkyl), —SO$_2$—($C_{1-4}$)alkyl, —SO$_2$—NH$_2$, —SO$_2$—NH($C_{1-4}$-alkyl), —SO$_2$—N($C_{1-4}$alkyl)$_2$, —N—R$^7$, —($C_{1-4}$)alkyl-N—R$^7$, cyano, (halo)$_{1-3}$, hydroxy, nitro, oxo, -cycloalkyl-R$^6$, —($C_{1-4}$) alkyl-cycloalkyl-R$^6$, -heterocyclyl-R$^6$, —($C_{1-4}$) alkyl-heterocyclyl-R$^6$, -aryl-R$^6$, —($C_{1-4}$)alkyl-aryl-R$^6$, -heteroaryl-R$^6$ and —($C_{1-4}$)alkyl-heteroaryl-R$^6$.

4. The compound of claim 1 wherein R$^5$ is 1 to 2 substituents independently selected from the group consisting of hydrogen, —O—($C_{1-4}$)alkyl, —C(O)H, —N—R$^7$, —($C_{1-4}$)alkyl-N—R$^7$, hydroxy, -heterocyclyl-R$^6$ and —($C_{1-4}$) alkyl-heterocyclyl-R$^6$.

5. The compound of claim 1 wherein R$^5$ is 1 to 2 substituents independently selected from the group consisting of hydrogen, —O—($C_{1-4}$)alkyl, —C(O)H, —N—R$^7$, —($C_{1-4}$)alkyl-N—R$^7$, hydroxy, -pyrrolidinyl-R$^6$, -morpholinyl-R$^6$, -thiazolidinyl-R$^6$, —($C_{1-4}$)alkyl-piperidinyl-R$^6$ and -piperazinyl-R$^6$.

6. The compound of claim 1 wherein R$^6$ is 1 to 4 substituents attached to a carbon or nitrogen atom independently selected from the group consisting of hydrogen, —C$_{1-4}$alkyl, —(C$_{1-4}$)alkyl-(halo)$_{1-3}$ or —(C$_{1-4}$)alkyl-OH;
with the proviso that, when R$^6$ is attached to a carbon atom, R$^6$ is further selected from —C$_{1-4}$alkoxy, —C(O)NH$_2$, —NH$_2$, —NH(C$_{1-4}$alkyl), —N(C$_{1-4}$alkyl)$_2$, cyano, halo, —(C$_{1-4}$)alkoxy-(halo)$_{1-3}$, hydroxy and nitro.

7. The compound of claim 1 wherein R$^6$ is 1 to 4 substituents attached to a carbon or nitrogen atom independently selected from the group consisting of hydrogen and —C$_{1-4}$alkyl; with the proviso that, when R$^6$ is attached to a carbon atom, R$^6$ is further selected from halo.

8. The compound of claim 1 wherein R$^7$ is 2 substituents independently selected from the group consisting of hydrogen, —C$_{1-6}$alkyl, —C$_{2-6}$alkenyl, —C$_{2-6}$alkynyl, —(C$_{1-4}$)alkyl-OH, —(C$_{1-4}$)alkyl-O—(C$_{1-4}$)alkyl, —(C$_{1-4}$)alkyl-NH$_2$, —(C$_{1-4}$)alkyl-NH(C$_{1-6}$alkyl), —(C$_{1-4}$)alkyl-N(C$_{1-6}$alkyl)$_2$, —(C$_{1-4}$)alkyl-S—(C$_{1-4}$)alkyl, —C(O)—(C$_{1-4}$)alkyl, —C(O)—O—(C$_{1-4}$)alkyl, —C(O)—NH$_2$, —C(O)—NH(C$_{1-6}$alkyl), —C(O)—N(C$_{1-6}$alkyl)$_2$, —SO$_2$—(C$_{1-4}$)alkyl, —SO$_2$—NH$_2$, —SO$_2$—NH(C$_{1-6}$alkyl), —SO$_2$—N(C$_{1-6}$alkyl)$_2$, —C(N)—NH$_2$, -cycloalkyl-R$^8$, —(C$_{1-4}$)alkyl-heterocyclyl-R$^8$, -aryl-R$^8$, —(C$_{1-4}$)alkyl-aryl-R$^8$ and —(C$_{1-4}$)alkyl-heteroaryl-R$^8$.

9. The compound of claim 1 wherein R$^7$ is 2 substituents independently selected from the group consisting of hydrogen, —C$_{1-6}$alkyl, —C$_{2-6}$alkenyl, —C$_{2-6}$alkynyl, —(C$_{1-4}$)alkyl-OH, —(C$_{1-4}$)alkyl-N(C$_{1-6}$alkyl)$_2$ and —(C$_{1-4}$)alkyl-heteroaryl-R$^8$.

10. The compound of claim 1 wherein R$^7$ is 2 substituents independently selected from the group consisting of hydrogen, —C$_{1-6}$alkyl, —C$_{2-6}$alkenyl, —C$_{2-6}$alkynyl, —(C$_{1-4}$)alkyl-OH, —(C$_{1-4}$)alkyl-N(C$_{1-6}$alkyl)$_2$ and —(C$_{1-4}$)alkyl-furyl-R$^8$.

11. The compound of claim 1 wherein R$^8$ is 1 to 4 substituents attached to a carbon or nitrogen atom independently selected from the group consisting of hydrogen, —C$_{1-4}$alkyl, —(C$_{1-4}$)alkyl-(halo)$_{1-3}$ and —(C$_{1-4}$)alkyl-OH;
with the proviso that, when R$^8$ is attached to a carbon atom, R$^8$ is further selected from the group consisting of —C$_{1-4}$alkoxy, —NH$_2$, —NH(C$_{1-4}$alkyl), —N(C$_{1-4}$alkyl)$_2$, cyano, halo, —(C$_{1-4}$)alkoxy-(halo)$_{1-3}$, hydroxy and nitro.

12. The compound of claim 1 wherein R$^8$ is 1 to 4 substituents attached to a carbon or nitrogen atom independently selected from the group consisting of hydrogen and —C$_{1-4}$alkyl.

13. The compound of claim 1 wherein R$^2$ is one substituent attached to a carbon selected from the group consisting of hydrogen, —C$_{1-4}$alkyl-R$^5$, —C$_{2-4}$alkenyl-R$^5$, —C$_{2-4}$alkynyl-R$^5$, —C(O)H, —C(O)—(C$_{1-4}$)alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)—NH(aryl-R$^8$), —C(O)-cycloalkyl-R$^8$, —C(O)-heterocyclyl-R$^8$, —C(O)-aryl-R$^8$, —C(O)-heteroaryl-R$^8$, —CO$_2$H, —C(O)—O—(C$_{1-4}$)alkyl-R$^9$, —C(O)—O-aryl-R$^8$, —SO$_2$—(C$_{1-4}$)alkyl-R$^9$, —SO$_2$-aryl-R$^8$, -cycloalkyl-R$^6$, -aryl-R$^6$, —(C$_{1-4}$)alkyl-N—R$^7$, —C$_{1-4}$alkoxy-R$^5$, —N—R$^7$, cyano, halogen, hydroxy, nitro, oxo (wherein oxo is attached to a saturated carbon atom), -heterocyclyl-R$^6$ and -heteroaryl-R$^6$.

14. The compound of claim 1 wherein R$^2$ is one substituent attached to a carbon atom selected from the group consisting of hydrogen, —C$_{1-4}$alkyl-R$^5$, —C$_{1-4}$alkoxy-R$^5$, halogen and hydroxy.

15. The compound of claim 1 wherein R$^2$ is one substituent attached to a carbon atom selected from the group consisting of hydrogen, —C$_{1-4}$alkyl-R$^5$, —C$_{1-4}$alkoxy-R$^5$, bromine, iodine and hydroxy.

16. The compound of claim 1 wherein R$^9$ is 1 to 2 substituents independently selected from the group consisting of hydrogen, —C$_{1-4}$alkoxy, —NH$_2$, —NH(C$_{1-4}$alkyl), —N(C$_{1-4}$alkyl)$_2$, cyano, (halo)$_{1-3}$, hydroxy and nitro.

17. The compound of claim 1 wherein R$^9$ is hydrogen.

18. The compound of claim 1 wherein R$^3$ is 1 to 4 substituents attached to a carbon atom independently selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$^{10}$, —C(O)H, —C(O)—(C$_{1-4}$alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^9$, —C(NH)—NH$_2$, —CO$_2$H, —C(O)—O—(C$_{1-4}$)alkyl-R$^9$, —C(O)—O-aryl-R$^8$, —SO$_2$—(C$_{1-4}$)alkyl-R$^8$, —SO$_2$-aryl-R$^8$, —N—R$^7$, —(C$_{1-4}$alkyl-N—R$^7$, cyano, halogen, hydroxy, nitro, -cycloalkyl-R$^8$, -heterocyclyl-R$^8$, -aryl-R$^8$ and -heteroaryl-R$^8$.

19. The compound of claim 1 wherein R$^3$ is 1 to 4 substituents attached to a carbon atom independently selected from the group consisting of hydrogen and halogen.

20. The compound of claim 1 wherein R$^3$ is hydrogen.

21. The compound of claim 1 wherein R$^4$ is 1 to 4 substituents attached to a carbon atom independently selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$_{10}$, —C(O)H, —C(O)—(C$_{1-4}$alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-4}$)alkyl-R$^9$, —C(O)—O-aryl-R$^8$, —SH, —S—(C$_{1-4}$)alkyl-R$^{10}$, —SO$_2$—(C$_{1-4}$)alkyl-R$^9$, —SO$_2$-aryl-R$^8$, —SO$_2$—NH$_2$, —SO$_2$—NH(C$_{1-4}$alkyl-R$^9$), —SO$_2$—N(C$_{1-4}$alkyl-R$^9$)$_2$, —N—R$^7$, —(C$_{1-4}$alkyl-N—R$^7$, cyano, halogen, hydroxy, nitro, -cycloalkyl-R$^8$, -heterocyclyl-R$^8$, -aryl-R$^8$ and -heteroaryl-R$^8$.

22. The compound of claim 1 wherein R$^4$ is 1 to 4 substituents attached to a carbon atom independently selected from the group consisting of hydrogen, —C$^{1-4}$alkyl-R$^{10}$ and halogen.

23. The compound of claim 1 wherein $R^4$ is 1 to 4 substituents attached to a carbon atom independently selected from the group consisting of hydrogen, —$C_{1-4}$alkyl-$R^{10}$ and chlorine.

24. The compound of claim 1 wherein $R^{10}$ is 1 to 2 substituents independently selected from the group consisting of hydrogen, —$NH_2$, —$NH(C_{1-4}alkyl)$, —$N(C_{1-4}alkyl)_2$, cyano, $(halo)_{1-3}$, hydroxy, nitro and oxo.

25. The compound of claim 1 wherein $R^{10}$ is hydrogen.

26. The compound of claim 1 wherein $R^{11}$ is selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, -aryl-$R^8$, -heteroaryl-$R^8$ and halogen.

27. The compound of claim 1 wherein $R^{11}$ is hydrogen.

28. The compound of claim 1 wherein the compound of Formula (I) is selected from Formula (Ia):

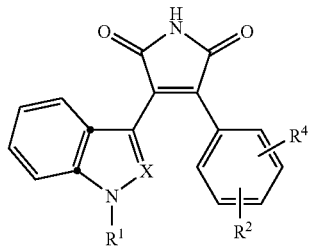

Formula (Ia)

wherein $R^1$, $R^2$, $R^4$ and X are dependently selected from the group consisting of

| $R^1$ | $R^2$ | $R^3$ | $R^4$ | X |
|---|---|---|---|---|
| 5-pyrimidinyl | 2-(—$OCH_3$) | H | H | CH; |
| 3-pyridinyl | 2-(—$OCH_3$) | H | H | CH; |
| 3-pyridinyl | 2-OH | H | H | CH; |
| 3-pyridinyl | 4-OH | H | H | CH; |

-continued

| $R^1$ | $R^2$ | $R^3$ | $R^4$ | X |
|---|---|---|---|---|
| 5-carboxypyridin-3-yl | 2-O—$CH_3$ | 5-Cl | H | CH; |
| 5-methoxycarbonylpyridin-3-yl | 2-O—$CH_3$ | 5-Cl | H | CH; |
| 5-carbamoylpyridin-3-yl | 2-O—$CH_3$ | 5-Cl | H; | CH; | and pharmaceutically acceptable salts thereof.

29. The compound of claim 1 wherein the compound of Formula (I) is selected from Formula (Ib):

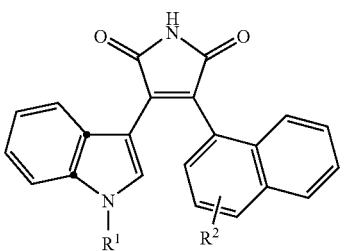

Formula (Ib)

wherein $R^1$ and $R^2$ are dependently selected from the group consisting of

| $R^1$ | $R^2$ |
|---|---|
| 5-pyrimidinyl | H; | and pharmaceutically acceptable salts thereof.

30. A composition comprising a compound of claim 1 and a pharmaceutically acceptable carrier.

31. A method for preparing a composition comprising mixing a compound of claim 1 and a pharmaceutically acceptable carrier.

* * * * *